United States Patent [19]
Burke et al.

[11] Patent Number: 5,171,568
[45] Date of Patent: Dec. 15, 1992

[54] RECOMBINANT HERPES SIMPLEX GB-GD VACCINE

[75] Inventors: Rae L. Burke, San Francisco; Carol Pachl, Oakland; Pablo D. T. Valenzuela, San Francisco, all of Calif.

[73] Assignee: Chiron Corporation, Emeryville, Calif.

[21] Appl. No.: 416,425

[22] Filed: Oct. 2, 1989

Related U.S. Application Data

[63] Continuation of Ser. No. 079,605, Jul. 29, 1987, abandoned, which is a continuation-in-part of Ser. No. 921,213, Oct. 20, 1986, abandoned, which is a continuation-in-part of Ser. No. 597,784, Apr. 8, 1984, abandoned, and a continuation-in-part of Ser. No. 631,669, Jul. 17, 1984, Pat. No. 4,618,578.

[51] Int. Cl.$^5$ .......................................... A61K 39/245
[52] U.S. Cl. ...................................... 424/89; 424/450; 435/235.1; 514/8
[58] Field of Search ............... 424/89, 450; 435/235.1; 514/8

[56] References Cited

U.S. PATENT DOCUMENTS

| | | | |
|---|---|---|---|
| 4,317,811 | 3/1982 | Bertland et al. | 424/89 |
| 4,323,559 | 4/1982 | Audibert et al. | 514/8 |
| 4,374,127 | 2/1983 | Larson et al. | 424/89 |
| 4,396,607 | 8/1983 | Lefrancier et al. | 514/8 |
| 4,406,890 | 9/1983 | Tarcsay et al. | 514/8 |
| 4,452,734 | 6/1984 | Larson et al. | 514/8 |
| 4,606,918 | 8/1986 | Allison et al. | 424/88 |
| 4,618,578 | 10/1986 | Burke et al. | 435/69.1 |
| 4,642,333 | 2/1987 | Person | 530/350 |
| 4,661,349 | 4/1987 | Kino et al. | 424/89 |
| 4,724,146 | 2/1988 | Kino et al. | 424/89 |
| 4,762,708 | 8/1988 | Cohen et al. | 424/89 |
| 4,818,694 | 4/1989 | Watson et al. | 435/69.4 |
| 4,855,224 | 8/1989 | Berman et al. | 435/5 |
| 4,891,315 | 1/1990 | Watson et al. | 435/69.3 |

FOREIGN PATENT DOCUMENTS

| | | |
|---|---|---|
| 0100521 | 2/1984 | European Pat. Off. |
| 0133063 | 2/1985 | European Pat. Off. |
| 0168662 | 1/1986 | European Pat. Off. |
| 0170169 | 2/1986 | European Pat. Off. |
| 8504587 | 10/1985 | PCT Int'l Appl. |
| 8704463 | 7/1987 | PCT Int'l Appl. |
| 8800971 | 2/1988 | PCT Int'l Appl. |

OTHER PUBLICATIONS

Mertz et al., *J. Infect. Dis.* (1990) 161:653–660.
Kutinova et al., *Vaccine* (1988) 6:223–228.
Skinner et al., *Med. Microbiol. Immunol.* (1987) 176:161–168.
Blacklaws et al., *Virology* (1990) 177:727–736.
Stanberry et al., *J. Infect. Dis.* (1987) 155(5):914–920.
Stanberry et al., *J. gen. Virol.* (1989) 70:3177–3185.
Weis et al., *Nature* (1983) 302:72–74.
Berman et al., *Science* (1983) 222:524–527.

(List continued on next page.)

Primary Examiner—Robert A. Wax
Assistant Examiner—R. Keith Baker
Attorney, Agent, or Firm—Barbara G. McClung; Roberta L. Robins

[57] ABSTRACT

Vaccines and therapeutic compositions and methods for their production and use against Herpes Simplex Virus (HSV) are provided employing recombinant HSV glycoproteins B and D.

The following *E. coli* HB 101 strains were deposited at the A.T.C.C., where the plasmid indicates the plasmid employed to transform the strain; pH203; pHS112; pHS114; pHS127A and pHS206 were deposited on Apr. 4, 1984, and assigned Accession Nos. 39649-39653, respectively; pYHS109 and pYHS118 were deposited on Jul. 11, 1984, and given Accession Nos. 39762 and 39763, respectively.

23 Claims, 23 Drawing Sheets

OTHER PUBLICATIONS

Laskey et al., *Biotechnology* (Jun. 1984) pp. 527–532.
De Luca et al., *Virology* (1982) 122:411–423.
Cappel et al., *J. Medical. Virol.* (1985) 16:137–145.
Pellett et al., *J. Virol.* (1985) 53(1):243–253.
Bzik et al., *Virology* (1984) 133:301–314.
Chan, *Immunology* (1983) 49:343–352.
Hilfenhaus et al., *Devel. Biol. Standard.* (1982) 52:321–331.
Roizman et al., *Devel. Biol. Standard.* (1982) 52:287–304.
Watson et al., *Science* (1982) 218:381–384.
Cohen et al., *J. Virol.* (1984) 49:102–108.
Dundarov et al., *Devel. Biol. Standard.* (1982) 52:351–357.
Skinner et al., *Devel. Biol. Standard.* (1982) 52:333–344.
Eberle et al., *J. Infect. Dis.* (1983) 148(3):436–444.
Marsden et al., *J. Virol.* (1978) 28(2):624–642.
Ruyechan et al., *J. Virol.* (1979) 29(2):677–697.
Skare et al., *Virology* (1977) 76:581–595.
Roizman et al., *Ann. Rev. Genetics* (1979) 13:25–57.
Berman et al., *Science* (1985) 227:1490–1492.

```
-308 TCGCGAGCTCATTATCGCCACCACACTCTTTGCGTCGGTCTACCGGTGCGGGGAGCTTGA
     TCGCGAGCTGATTATCGCCACCACACTCTTTGCCTCGGTCTACCGGTGCGGGGAGCTCGA

GTTGCGCCGCCCCGACTGCAGCCGCCCGACCTCCGAAGGTCTGTACCGCTACCCGCCGG
     GTTGCGCCGCCCGGACTGCAGCCGCCCGACCTCCGAAGGTCGTTACCGTTACCCGCCCG

-189 GCGTGTACCTCACGTACAACTCCGACTGTCCGCTGGTGGCCATCGTCGAGAGCGGCCCCG
     GCGTATATCTCACGTACGACTCCGACTGTCCGCTGGTGGCCATCGTCGAGAGCGCCCCCG

ACGGCTGCATCGGACCCCGCTCGGTCGTGGTTTACGACCGAGACGTTTTTTCCATCCTC
     ACGGCTGTATCGGCCCCCGGTCGGTCGTGGTCTACGACCGAGACGTTTTCTCGATCCTC

-70 TACTCGGTCCTGCAGCACCTCGCCCCCAGACTAGCGGGCGGCGGGAGCGACGCGCCCCCG
     TACTCGGTCCTCCAGCACCTCGCCCCCAGGCTACCTGACGGGGGGCACGACGGGCCCCCG

Met Arg Gly Gly Gly Leu Ile         Cys Ala Leu   10
     TAGGCCCGCC  ATG CGC GGG GGG GGC TTG ATT ::: ::: TGC GCG CTG
     TAGTCCCGCC  ATG CGC CAG GGC GCC CCC GCG CGG GGG TGC CGG TGG
                 Met Arg Gln Gly Ala Pro Ala Arg Gly Cys Arg Trp

Val Val Gly Ala Leu Val Ala Ala                     Val
 31 ::: GTC GTG GGG GCG CTG GTG GCC GCG ::: ::: ::: ::: ::: GTG
    TTC GTC GTA TGG GCG CTC TTG GGG TTG ACG CTG GGG GTC CTG GTG
    Phe Val Val Trp Ala Leu Leu Gly Leu Thr Leu Gly Val Leu Val

Ala Ser Ala Ala Pro Ala Ala Pro Ala Ala Pro Arg Ala Ser Gly   34
     GCG TCG GCG GCC CCG GCG GCC CCG GCG GCC CCC CGC GCC TCG GGC
     GCG TCG GCG GCT CCG AGT TCC CCC GGC ACG CCT ::: ::: ::: :::
     Ala Ser Ala Ala Pro Ser Ser Pro Gly Thr Pro

Gly Val     Ala Ala Thr Val Ala Ala Asn Gly Gly Pro Ala Ser
 103 GGC GTG ::: GCC GCG ACC GTC GCG GCG AAC GGG GGT CCC GCC TCC
     GGG GTC GCG GCC GCG ACC CAG GCG GCG AAC GGG GGC CCT GCC ACT
     Gly Val Ala Ala Ala Thr Gln Ala Ala Asn Gly Gly Pro Ala Thr

Arg Pro Pro Pro Val Pro Ser Pro Ala Thr Thr Lys Ala Arg Lys   63
     CGG CCG CCC CCC GTC CCG AGC CCC GCG ACC ACC AAG GCC CGG AAG
     CCG GCG CCG CCC GCC CTT GGC GCC GCC CCA ACG GGG GAC CCG AAA
     Pro Ala Pro Pro Ala Leu Gly Ala Ala Pro Thr Gly Asp Pro Lys

Arg Lys Thr Lys Lys Pro Pro Lys Arg Pro Glu Ala Thr Pro Pro
 190 CGG AAA ACC AAA AAG CCG CCC AAG CGG CCC GAG GCG ACC CCG CCC
     CCG AAG AAG AAC AAA AAA CCG AAA AAC CCA ::: ::: ACG CCG CCA
     Pro Lys Lys Asn Lys Lys Pro Lys Asn Pro         Thr Pro Pro

Pro Asp Ala         Asn Ala Thr Val Ala Ala Gly His Ala Thr   91
     CCC GAC GCC ::: ::: AAC GCG ACC GTC GCC GCC GGC CAC GCC ACG
     GCG CCC GCC GGC GAC AAC GCG ACC GTC GCC GCG GGC CAC GCC ACC
     Arg Pro Ala Gly Asp Asn Ala Thr Val Ala Ala Gly His Ala Thr

Leu Arg Ala His Leu Arg Glu Ile Lys Val Glu Asn Ala Asp Ala
 274 CTG CGC GCG CAC CTG CGG GAA ATC AAG GTC GAG AAC GCC GAT GCC
     CTG CGC GAG CAC CTG-CGG GAC ATC AAG GCG GAG AAC ACC GAT GCA
     Leu Arg Glu His Leu Arg Asp Ile Lys Ala Glu Asn Thr Asp Ala

Gln Phe Tyr Val Cys Pro Pro Pro Thr Gly Ala Thr Val Val Gln  121
     CAG TTT TAC GTG TGC CCG CCC CCG ACG GGC GCC ACG GTG GTG CAG
     AAC TTT TAC GTG TGC CCA CCC CCC ACG GGC GCC ACG GTG GTG CAG
     Asn Phe Tyr Val Cys Pro Pro Pro Thr Gly Ala Thr Val Val Gln
```

FIG. 4-1

```
        Phe Glu Gln Pro Arg Arg Cys Pro Thr Arg Pro Glu Gly Gln Asn
364     TTT GAG CAG CCG CGC CGC TGC CCG ACG CGC CCG GAG GGG CAG AAC
        TTC GAG CAG CCG CGC CGC TGC CCG ACC CGG CCC GAG GGT CAG AAC
        Phe Glu Gln Pro Arg Arg Cys Pro Thr Arg Pro Glu Gly Gln Asn

Tyr Thr Glu Gly Ile Ala Val Val Phe Lys Glu Asn Ile Ala Pro    151
        TAC ACG GAG GGC ATC GCG GTG GTC TTC AAG GAG AAC ATC GCC CCG
        TAC ACG GAG GGC ATC GCG GTG GTC TTC AAG GAG AAC ATC GCC CCG
        Tyr Thr Glu Gly Ile Ala Val Val Phe Lys Glu Asn Ile Ala Pro

Tyr Lys Phe Lys Ala Thr Met Tyr Tyr Lys Asp Val Thr Val Ser
454     TAC AAA TTC AAG GCC ACC ATG TAC TAC AAA GAC GTG ACC GTG TCG
        TAC AAG TTC AAG GCC ACC ATG TAC TAC AAA GAC GTC ACC GTT TCG
        Tyr Lys Phe Lys Ala Thr Met Tyr Tyr Lys Asp Val Thr Val Ser

Gln Val Trp Phe Gly His Arg Tyr Ser Gln Phe Met Gly Ile Phe    181
        CAG GTG TGG TTC GGC CAC CGC TAC TCC CAG TTT ATG GGG ATA TTC
        CAG GTG TGG TTC GGC CAC CGC TAC TCC CAG TTT ATG GGG ATC TTT
        Gln Val Trp Phe Gly His Arg Tyr Ser Gln Phe Met Gly Ile Phe

Glu Asp Arg Ala Pro Val Pro Phe Glu Glu Val Ile Asp Lys Ile
544     GAG GAC CGC GCC CCC GTT CCC TTC GAG GAG GTG ATC GAC AAG ATT
        GAG GAC CGC GCC CCC GTC CCC TTC GAG GAG GTG ATC GAC AAG ATC
        Glu Asp Arg Ala Pro Val Pro Phe Glu Glu Val Ile Asp Lys Ile

Asn Ala Lys Gly Val Cys Arg Ser Thr Ala Lys Tyr Val Arg Asn    211
        AAC GCC AAG GGG GTC TGC CGC TCC ACG GCC AAG TAC GTG CGG AAC
        AAC GCC AAG GGG GTC TGT CGG TCC ACG GCC AAG TAC GTG CGC AAC
        Asn Ala Lys Gly Val Cys Arg Ser Thr Ala Lys Tyr Val Arg Asn

Asn Met Glu Thr Thr Ala Phe His Arg Asp Asp His Glu Thr Asp
634     AAC ATG GAG ACC ACC GCG TTT CAC CGG GAC GAC CAC GAG ACC GAC
        AAC CTG GAG ACC ACC GCG TTT CAC CGG GAC GAC CAC GAG ACC GAC
        Asn Leu Glu Thr Thr Ala Phe His Arg Asp Asp His Glu Thr Asp

Met Glu Leu Lys Pro Ala Lys Val Ala Thr Arg Thr Ser Arg Gly    241
        ATG GAG CTC AAG CCG GCG AAG GTC GCC ACG CGC ACG AGC CGG GGG
        ATG GAG CTG AAA CCG GCC AAC GCC GCG ACC CGC ACG AGC CGG GGC
        Met Glu Leu Lys Pro Ala Asn Ala Ala Thr Arg Thr Ser Arg Gly

Trp His Thr Thr Asp Leu Lys Tyr Asn Pro Ser Arg Val Glu Ala
724     TGG CAC ACC ACC GAC CTC AAG TAC AAC CCC TCG CGG GTG GAG GCG
        TGG CAC ACC ACC GAC CTC AAG TAC AAC CCC TCG CGG GTG GAG GCG
        Trp His Thr Thr Asp Leu Lys Tyr Asn Pro Ser Arg Val Glu Ala

Phe His Arg Tyr Gly Thr Thr Val Asn Cys Ile Val Glu Glu Val    271
        TTC CAT CGG TAC GGC ACG ACG GTC AAC TGC ATC GTC GAG GAG GTG
        TTC CAC CGG TAC GGG ACG ACG GTA AAC TGC ATC GTC GAG GAG GTG
        Phe His Arg Tyr Gly Thr Thr Val Asn Cys Ile Val Glu Glu Val

Asp Ala Arg Ser Val Tyr Pro Tyr Asp Glu Phe Val Leu Ala Thr
814     GAC GCG CGG TCG GTG TAC CCG TAC GAT GAG TTT GTG TTG GCG ACG
        GAC GCG CGC TCG GTG TAC CCG TAC GAC GAG TTT GTG CTG GCG ACT
        Asp Ala Arg Ser Val Tyr Pro Tyr Asp Glu Phe Val Leu Ala Thr

Gly Asp Phe Val Tyr Met Ser Pro Phe Tyr Gly Tyr Arg Glu Gly    301
        GGC GAC TTT GTG TAC ATG TCC CCG TTT TAC GGC TAC CGG GAG GGG
        GGC GAC TTT GTG TAC ATG TCC CCG TTT TAC GGC TAC CGG GAG GGG
        Gly Asp Phe Val Tyr Met Ser Pro Phe Tyr Gly Tyr Arg Glu Gly
```

FIG.4-2

```
        Ser His Thr Glu His Thr Ser Tyr Ala Ala Asp Arg Phe Lys Gln
    904 TCG CAC ACC GAG CAC ACC AGC TAC GCC GCC GAC CGC TTC AAG CAG
        TCG CAC ACC GAA CAC ACC AGC TAC GCC GCC GAC CGC TTC AAG CAG
        Ser His Thr Glu His Thr Ser Tyr Ala Ala Asp Arg Phe Lys Gln

Val Asp Gly Phe Tyr Ala Arg Asp Leu Thr Thr Lys Ala Arg Ala  331
        GTC GAC GGC TTC TAC GCG CGC GAC CTC ACC ACG AAG GCC CGG GCC
        GTC GAC GGC TTC TAC GCG CGC GAC CTC ACC ACC AAG GCC CGG GCC
        Val Asp Gly Phe Tyr Ala Arg Asp Leu Thr Thr Lys Ala Arg Ala

Thr Ser Pro Thr Thr Arg Asn Leu Leu Thr Thr Pro Lys Phe Thr
    994 ACG TCG CCG ACG ACC CGC AAC TTG CTG ACG ACC CCC AAG TTT ACC
        ACG GCG CCG ACC ACC CGG AAC CTG CTC ACG ACC CCC AAG TTC ACC
        Thr Ala Pro Thr Thr Arg Asn Leu Leu Thr Thr Pro Lys Phe Thr

Val Ala Trp Asp Trp Val Pro Lys Arg Pro Ala Val Cys Thr Met  361
        GTG GCC TGG GAC TGG GTG CCG AAG CGA CCG GCG GTC TGC ACC ATG
        GTG GCC TGG GAC TGG GTG CCA AAG CGC CCG TCG GTC TGC ACC ATG
        Val Ala Trp Asp Trp Val Pro Lys Arg Pro Ser Val Cys Thr Met

Thr Lys Trp Gln Glu Val Asp Glu Met Leu Arg Ala Glu Tyr Gly
   1084 ACC AAG TGG CAG GAG GTG GAC GAG ATG CTC CGC GCC GAG TAC GGC
        ACC AAG TGG CAG GAG GTG GAC GAG ATG CTG CGC TCC GAG TAC GGC
        Thr Lys Trp Gln Glu Val Asp Glu Met Leu Arg Ser Glu Tyr Gly

Gly Ser Phe Arg Phe Ser Ser Asp Ala Ile Ser Thr Thr Phe Thr  391
        GGC TCC TTC CGC TTC TCC TCC GAC GCC ATC TCG ACC ACC TTC ACC
        GGC TCC TTC CGA TTC TCC TCC GAC GCC ATA TCC ACC ACC TTC ACC
        Gly Ser Phe Arg Phe Ser Ser Asp Ala Ile Ser Thr Thr Phe Thr

Thr Asn Leu Thr Gln Tyr Ser Leu Ser Arg Val Asp Leu Gly Asp
   1174 ACC AAC CTG ACC CAG TAC TCG CTC TCG CGC GTC GAC CTG GGC GAC
        ACC AAC CTG ACC GAG TAC CCG CTC TCG CGC GTT GAC CTG GGG GAC
        Thr Asn Leu Thr Glu Tyr Pro Leu Ser Arg Val Asp Leu Gly Asp

Cys Ile Gly Arg Asp Ala Arg Glu Ala Ile Asp Arg Met Phe Ala  421
        TGC ATT GGC CGG GAT GCC CGC GAG GCC ATC GAC CGC ATG TTT GCG
        TGC ATC GGC AAG GAC GCC CGC GAC GCC ATG GAC CGC ATC TTC GCC
        Cys Ile Gly Lys Asp Ala Arg Asp Ala Met Asp Arg Ile Phe Ala

Arg Lys Tyr Asn Ala Thr His Ile Lys Val Gly Gln Pro Gln Tyr
   1264 CGC AAG TAC AAC GCC ACG CAC ATC AAG GTG GGC CAG CCG CAG TAC
        CGC AGG TAC AAC GCG ACG CAC ATC AAG GTC GGC CAG CCG CAG TAC
        Arg Arg Tyr Asn Ala Thr His Ile Lys Val Gly Gln Pro Gln Tyr

Tyr Leu Ala Thr Gly Gly Phe Leu Ile Ala Tyr Gln Pro Leu Leu  451
        TAC CTG GCC ACG GGG GGC TTC CTC ATC GCG TAC CAG CCC CTC CTC
        TAC CTG GCC AAT GGG GGC TTT CTG ATC GCG TAC CAG CCC CTT CTC
        Tyr Leu Ala Asn Gly Gly Phe Leu Ile Ala Tyr Gln Pro Leu Leu

Ser Asn Thr Leu Ala Glu Leu Tyr Val Arg Glu Tyr Met Arg Glu
   1354 AGC AAC ACG CTC GCC GAG CTG TAC GTG CGG GAG TAC ATG CGG GAG
        AGC AAC ACG CTC GCG GAG CTG TAC GTG CGG GAA CAC CTC CGA GAG
        Ser Asn Thr Leu Ala Glu Leu Tyr Val Arg Glu His Leu Arg Glu

Gln Asp Arg Lys Pro Arg Asn Ala Thr Pro Ala Pro Leu Arg Glu  481
        CAG GAC CGC AAG CCC CGG AAT GCC ACG CCC GCG CCA CTG CGG GAG
        CAG AGC CGC AAG CCC CCA ACC CCC ACG CCC CCG CCC ::: :::
        Gln Ser Arg Lys Pro Pro Asn Pro Thr Pro Pro Pro
```

FIG. 4-3

```
        Ala Pro Ser Ala Asn Ala Ser Val Glu Arg Ile Lys Thr Thr Ser
1444    GCG CCC AGC GCC AAC GCG TCC GTG GAG CGC ATC AAG ACC ACC TCC
        GGG GCC AGC GCC AAC GCG TCC GTG GAG CGC ATC AAG ACC ACC TCC
        Gly Ala Ser Ala Asn Ala Ser Val Glu Arg Ile Lys Thr Thr Ser

Ser Ile Glu Phe Ala Arg Leu Gln Phe Thr Tyr Asn His Ile Gln     511
        TCG ATC GAG TTC GCC CGG CTG CAG TTT ACG TAT AAC CAC ATA CAG
        TCC ATC GAG TTC GCC CGG CTG CAG TTT ACG TAC AAC CAC ATA CAG
        Ser Ile Glu Phe Ala Arg Leu Gln Phe Thr Tyr Asn His Ile Gln

Arg His Val Asn Asp Met Leu Gly Arg Ile  Ala Val  Ala Trp Cys
1534    CGC CAC GTG AAC GAC ATG CTG GGG CGC ATC GCC GTC GCG TGG TGC
        CGC CAT GTC AAC GAT ATG TTG GGC CGC GTT GCC ATC GCG TGG TGC
        Arg His Val Asn Asp Met Leu Gly Arg Val  Ala Ile  Ala Trp Cys

Glu Leu Gln Asn His Glu Leu Thr Leu Trp Asn Glu Ala Arg Lys     541
        GAG CTG CAG AAC CAC GAG CTG ACT CTC TGG AAC GAG GCC CGC AAG
        GAG CTG CAG AAC CAC GAG CTG ACC CTG TGG ACC GAG GCC CGC AAG
        Glu Leu Gln Asn His Glu Leu Thr Leu Trp Asn Glu Ala Arg Lys

Leu Asn Pro Asn Ala Ile Ala Ser Ala Thr Val Gly Arg Arg Val
1624    CTC AAC CCC AAC GCC ATC GCC TCC GCC ACC GTC GGC CGG CGG GTG
        CTG AAC CCC AAC GCC ATC GCC TCG GCC ACC GTG GGC CGG CGG GTG
        Leu Asn Pro Asn Ala Ile Ala Ser Ala Thr Val Gly Arg Arg Val

Ser Ala Arg Met Leu Gly Asp Val Met Ala Val Ser Thr Cys Val     571
        AGC GCG CGC ATG CTC GGA GAC GTC ATG GCC GTC TCC ACG TGC GTG
        AGC GCG CGG ATG CTC GGC GAC GTG ATG GCC GTC TCC ACG TGC GTG
        Ser Ala Arg Met Leu Gly Asp Val Met Ala Val Ser Thr Cys Val

Pro Val Ala Pro  Asp Asn Val Ile Val Gln Asn Ser Met Arg Val
1714    CCC GTC GCC CCG GAC AAC GTG ATC GTG CAG AAC TCG ATG CGC GTC
        CCG GTC GCC GCG GAC AAC GTG ATC GTC CAA AAC TCG ATG CGC ATC
        Pro Val Ala Ala  Asp Asn Val Ile Val Gln Asn Ser Met Arg Ile

Ser Ser Arg Pro Gly Thr  Cys Tyr Ser Arg Pro Leu Val Ser Phe    601
        AGC TCG CGG CCG GGG ACG TGC TAC AGC CGC CCC CTG GTC AGC TTT
        AGC TCG CGG CCC GGG GCC TGC TAC AGC CGC CCC CTG GTC AGC TTT
        Ser Ser Arg Pro Gly Ala  Cys Tyr Ser Arg Pro Leu Val Ser Phe

Arg Tyr Glu Asp Gln Gly Pro Leu Ile  Glu Gly Gln Leu Gly Glu
1804    CGG TAC GAA GAC CAG GGC CCG CTG ATC GAG GGG CAG CTG GGC GAG
        CGG TAC GAA GAC CAG GGC CCG TTG GTC GAG GGG CAG CTG GGG GAG
        Arg Tyr Glu Asp Gln Gly Pro Leu Val  Glu Gly Gln Leu Gly Glu

Asn Asn Glu Leu Arg Leu Thr Arg Asp Ala Leu  Glu Pro Cys Thr    631
        AAC AAC GAG CTG CGC CTC ACC CGC GAC GCG CTC GAG CCG TGC ACC
        AAC AAC GAG CTG CGG CTG ACG CGC GAT GCG ATC GAG CCG TGC ACC
        Asn Asn Glu Leu Arg Leu Thr Arg Asp Ala Ile  Glu Pro Cys Thr

Val Gly His Arg Arg Tyr Phe Ile  Phe Gly Gly Gly Tyr Val Tyr
1894    GTG GGC CAC CGG CGC TAC TTC ATC TTC GGC GGG GGC TAC GTG TAC
        GTG GGA CAC CGG CGC TAC TTC ACC TTC GGT GGG GGC TAC GTG TAC
        Val Gly His Arg Arg Tyr Phe Thr  Phe Gly Gly Gly Tyr Val Tyr

Phe Glu Glu Tyr  Ala Tyr Ser His Gln Leu Ser Arg Ala Asp Val    661
        TTC GAG GAG TAC GCG TAC TCT CAC CAG CTG AGT CGC GCC GAC GTC
        TTC GAG GAG TCA GCG TAC TCC CAC CAG CTG AGC CGC GCC GAC ATC
        Phe Glu Glu Ser  Ala Tyr Ser His Gln Leu Ser Arg Ala Asp Ile
```

FIG.4-4

```
          Thr Thr Val Ser Thr Phe Ile Asp Leu Asn Ile Thr Met Leu Glu
     1984 ACC ACC GTC AGC ACC TTC ATC GAC CTG AAC ATC ACC ATG CTG GAG
          ACC ACC GTC AGC ACC TTC ATC GAC CTC AAC ATC ACC ATG CTG GAG
          Thr Thr Val Ser Thr Phe Ile Asp Leu Asn Ile Thr Met Leu Glu

Asp His Glu Phe Val Pro Leu Glu Val Tyr Thr Arg His Glu Ile  691
          GAC CAC GAG TTT GTG CCC CTG GAG GTC TAC ACG CGC CAC GAG ATC
          GAT CAC GAG TTT GTC CCC CTG GAG GTG TAC ACC CGC CAC GAG ATC
          Asp His Glu Phe Val Pro Leu Glu Val Tyr Thr Arg His Glu Ile

Lys Asp Ser Gly Leu Leu Asp Tyr Thr Glu Val Gln Arg Arg Asn
     2074 AAG GAC AGC GGC CTG CTG GAC TAC ACG GAG GTC CAG CGC CGC AAC
          AAG GAC AGC GGC CTG CTG GAC TAC ACG GAG GTC CAG CGC CGC AAC
          Lys Asp Ser Gly Leu Leu Asp Tyr Thr Glu Val Gln Arg Arg Asn

Gln Leu His Asp Leu Arg Phe Ala Asp Ile Asp Thr Val Ile Arg  721
          CAG CTG CAC GAC CTG CGC TTT GCC GAC ATC GAC ACG GTC ATC CGC
          CAG CTG CAC GAC CTG CGC TTC GCC GAC ATC GAC ACG GTC ATC CAC
          Gln Leu His Asp Leu Arg Phe Ala Asp Ile Asp Thr Val Ile His

Ala Asp Ala Asn Ala Ala Met Phe Ala Gly Leu Cys Ala Phe Phe
     2164 GCC GAC GCC AAC GCC GCC ATG TTC GCG GGG CTG TGC GCG TTC TTC
          GCC GAC GCC AAC GCC GCC ATG TTC GCG GGC CTG GGT GCG TTT TTC
          Ala Asp Ala Asn Ala Ala Met Phe Ala Gly Leu Gly Ala Phe Phe

Glu Gly Met Gly Asp Leu Gly Arg Ala Val Gly Lys Val Val Met  751
          GAG GGG ATG GGG GAC TTG GGG CGC GCG GTC GGC AAG GTA GTC ATG
          GAG GGG ATG GGC GAC CTG GGG CGC GCG GTC GGC AAG GTG GTG ATG
          Glu Gly Met Gly Asp Leu Gly Arg Ala Val Gly Lys Val Val Met

Gly Val Val Gly Gly Val Val Ser Ala Val Ser Gly Val Ser Ser
     2254 GGA GTA GTG GGG GGC GTG GTG TCG GCC GTC TCG GGC GTG TCC TCC
          GGC ATC GTG GGC GGC GTG GTA TCG GCC GTG TCG GGC GTG TCC TCC
          Gly Ile Val Gly Gly Val Val Ser Ala Val Ser Gly Val Ser Ser

Phe Met Ser Asn Pro Phe Gly Ala Leu Ala Val Gly Leu Leu Val
          TTT ATG TCC AAC CCC TTC GGG GCG CTT GCC GTG GGG CTG CTG GTC
          TTC ATG TCC AAC CCC TTT GGG GCG CTG GCC GTG GGT CTG TTG GTC
          Phe Met Ser Asn Pro Phe Gly Ala Leu Ala Val Gly Leu Leu Val

Leu Ala Gly Leu Val Ala Ala Phe Phe Ala Phe Arg Tyr Val Leu
     2344 CTG GCC GGC CTG GTC GCG GCC TTC TTC GCC TTC CGC TAC GTC CTG
          CTG GCC GGC CTG GCG GCG GCC TTC TTC GCC TTT CGC TAC GTC ATG
          Leu Ala Gly Leu Ala Ala Ala Phe Phe Ala Phe Arg Tyr Val Met

Gln Leu Gln Arg Asn Pro Met Lys Ala Leu Tyr Pro Leu Thr Thr  811
          CAA CTG CAA CGC AAT CCC ATG AAG GCC CTG TAT CCG CTC ACC ACC
          CGG CTG CAG AGC AAC CCC ATG AAG GCC CTG TAC CCG CTA ACC ACC
          Arg Leu Gln Ser Asn Pro Met Lys Ala Leu Tyr Pro Leu Thr Thr

Lys Glu Leu Lys Thr Ser Asp Pro Gly Gly Val Gly Gly Glu Gly
     2434 AAG GAA CTC AAG ACT TCC GAC CCC GGG GGC GTG GGC GGG GAG GGG
          AAG GAG CTC AAG AAC CCC ACC AAC CCG GAC GCG TCC GGG GAG GGC
          Lys Glu Leu Lys Asn Pro Thr Asn Pro Asp Ala Ser Gly Glu Gly

Glu Glu Gly Ala Glu Gly Gly Gly Phe Asp Glu Ala Lys Leu Ala  841
          GAG GAA GGC GCG GAG GGG GGC GGG TTT GAC GAG GCC AAG TTG GCC
          GAG GAG GGC ::: ::: ::: GGC GAC TTT GAC GAG GCC AAG CTA GCC
          Glu Glu Gly             Gly Asp Phe Asp Glu Ala Lys Leu Ala
```

FIG.4-5

```
        Glu Ala Arg Glu Met Ile Arg Tyr Met Ala Leu Val Ser Ala Met
   2524 GAG GCC CGA GAA ATG ATC CGA TAT ATG GCT TTG GTG TCG GCC ATG
        GAG GCC CGG GAG ATG ATA CGG TAC ATG GCC CTG GTG TCT GCC ATG
        Glu Ala Arg Glu Met Ile Arg Tyr Met Ala Leu Val Ser Ala Met

Glu Arg Thr Glu His Lys Ala Arg Lys Lys Gly Thr Ser Ala Leu    871
        GAG CGC ACG GAA CAC AAG GCC AGA AAG AAG GGC ACG AGC GCC CTG
        GAG CGC ACG GAA CAC AAG GCC AAG AAG AAG GGC ACG AGC GCG CTG
        Glu Arg Thr Glu His Lys Ala Lys Lys Lys Gly Thr Ser Ala Leu

Leu Ser Ser Lys Val Thr Asn Met Val Leu Arg Lys Arg Asn Lys
   2614 CTC AGC TCC AAG GTC ACC AAC ATG GTT CTG GCC AAG CGC AAC AAA
        CTC AGC GCC AAG GTC ACC GAC ATG GTC ATG CGC AAG CGC CGC AAC
        Leu Ser Ala Lys Val Thr Asp Met Val Met Arg Lys Arg Arg Asn

Ala Arg Tyr Ser Pro Leu His Asn Glu Asp Glu Ala Gly Asp Glu   901
        GCC AGG TAC TCT CCG CTC CAC AAC GAG GAC GAG GCC GGA GAC GAA
        ACC AAC TAC ACC CAA GTT CCC AAC AAA GAC GGT GAC GCC GAC GAG
        Thr Asn Tyr Thr Gln Val Pro Asn Lys Asp Gly Asp Ala Asp Glu

Asp Glu Leu OC
   2704 GAC GAG CTC TAA GGGAGGGGAGGGGAGCTGGGCTTGTGTATAAATAAAAAGACACC
        GAC GAC CTG TGA CGGGGGGTTTGTTGTAAATAAAAACCACGGGTGTTAAACCGCAT
        Asp Asp Leu OP

904
        GATGTTCAAAAATACACATGACTTCTGGTATTGTTTTGCCTTGGTTTTTATTTGGGGGG
        GTGCATCTTTTGGTGTGTTTGTTTGGTACGCCTTTTGTGTGTGTGGGAAGAAAGAAAAG

2819 GGGGCGTGTGACTAGAAAAACAAATGCAGACATGTGCTAACGGGAAAACCAACCCCAAAC
        GGAACACATAAACTCCCCCGGGTGTCCGCGGCCTGTTTCCTCTTTCCTTTCCCGTGACAA

CAACCCCAAACCAACCCCGTCTCCCTGCGACCGGTCGCTTTCCACACCCCCTCCCCGTG
        AACGGACCCCCTTGGTCAGTGCCGATTCCCCCCCACGCCTTCCTCCACGTCGAAGGCTT

2938 GTAGTCTTCCGGGCCTTCCGTCGCGTGTGGGGGCCATCGGTTCGGCTCCTAGCCCCCCCC
        TTGCATTGTAAAGCTACCCGCCTACCCGCGCCTCCCAATAAAAAAAAAGAACATACACCA

CCCTCACCCCTCCGACCTAATTTTTGTGTCATTCGGCCCACTTTCCCCCCCACTCCACC
        ATGGGTCTTATTTGGTATTACCTGGTTTATTTAAAAAGATATACAGTAAGACATCCCAT

3057 CCCCCCCTCTCAAACAAAAACACAAGCACACGAAGTGGGTATACTTTTGTCCGGTTGTTT
        GGTACCAAAGACCGGGGCGAATCAGCGGGCCCCCATCATCTGAGAGACGAACAAATCGGC

GTTTATTTAAAATATATGAAAACACACACCCCCCCCAAGTCCGGATCC
        GGCGCGGGCCGTGTCAACGTCCACGTGTGCTGCGCTGCTGGCGTTGAC
```

FIG.4-6

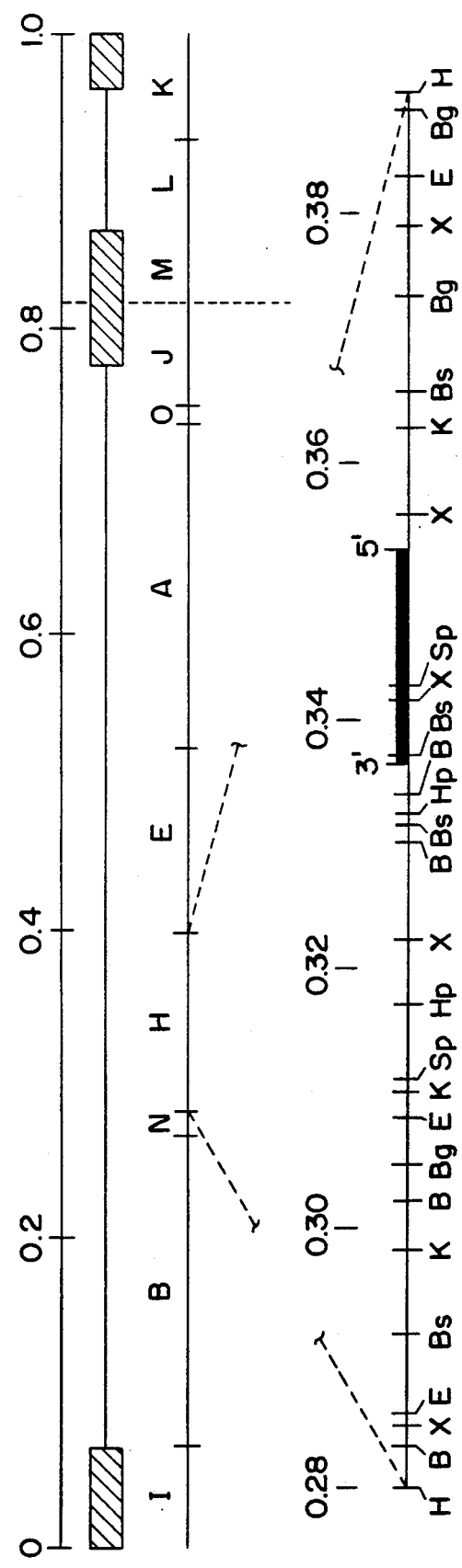
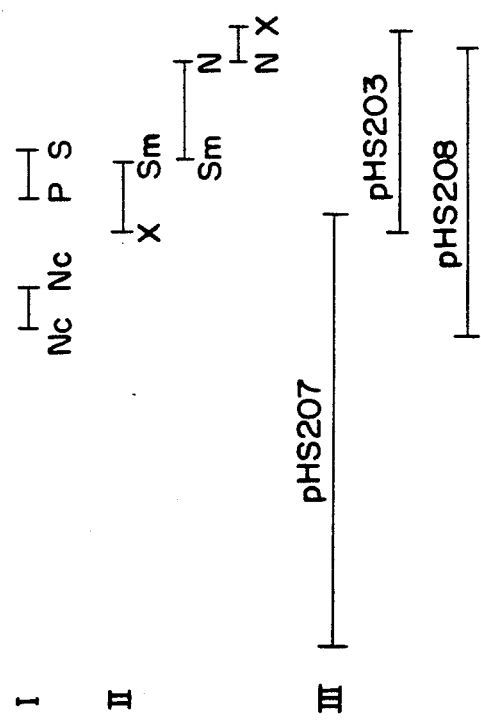
FIG. 7A
FIG. 7B

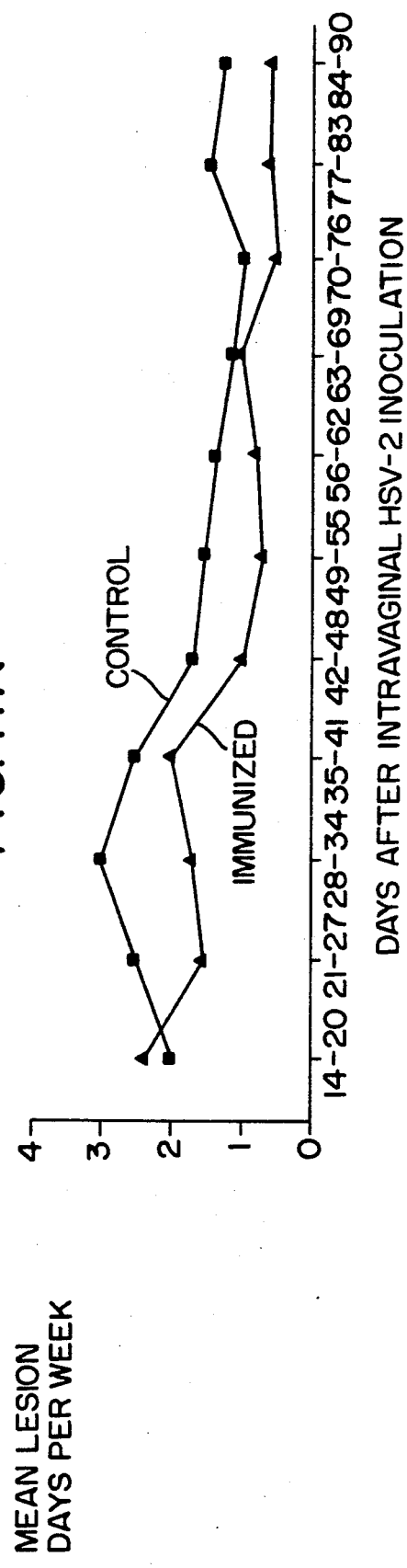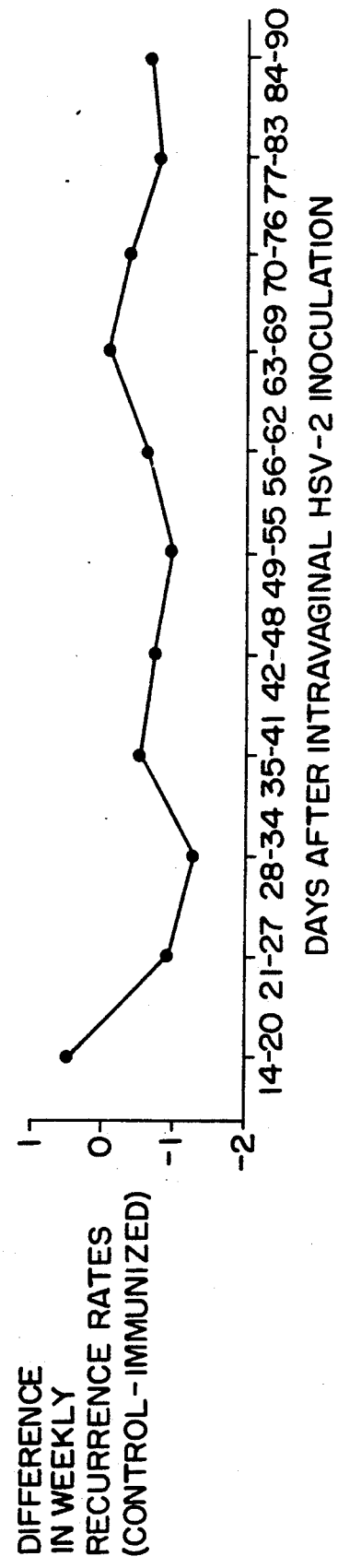

RECOMBINANT HERPES SIMPLEX GB-GD VACCINE

This application is a continuation of Ser. No. 07/079,605, filed July 29, 1987, now abandoned, which is a continuation-in-part application of Ser. No. 06/921,213, filed Oct. 20, 1986, now abandoned, which is a continuation-in-part application of Ser. No. 06/597,784, filed April 8, 1984, now abandoned, and Ser. No. 06/631,669, filed July 17, 1984, now U.S. Pat. No. 4,618,578.

BACKGROUND OF THE INVENTION

Field of the Invention

The herpes viruses include the herpes simplex viruses, comprising two closely related variants designated types 1 (HSV-1) and 2 (HSV-2). These types cross react strongly but can be distinguished by neutralization titrations. HSV-1 and HSV-2 are responsible for a variety of human diseases, such as skin infections, genital herpes, viral encephalitis and the like.

The herpes simplex virus is a double stranded DNA virus having a genome of about 150 to 160 kbp packaged within an icosahedral nucleocapsid enveloped in a membrane. The membrane includes a number of virus-specific glycoproteins, the most abundant of which are gB, gC, gD and gE, where gB and gD are cross-reactive between types 1 and 2.

It is a matter of great medical and scientific interest to provide safe and effective vaccines for humans against both HSV-1 and HSV-2 and, where infection has occurred, therapies for treatment of the disease.

One promising approach has been the use of isolated glycoproteins, which have been shown to provide projection when injected into mice subsequently challenged with live virus. However, the availability of the Herpes Simplex glycoproteins has heretofore been primarily dependent upon the growth of the virus and the isolation of the membranous proteins. The problems of commercial production of the glycoproteins associated with the handling of a dangerous pathogen, the maintenance of the virus in cell culture, the isolation of the glycoproteins free of the viral genome or portions thereof, have substantially precluded the use of the glycoproteins as vaccines. It would therefore be desirable to provide vaccines employing glycoproteins produced by methods other than by growth of the virus and isolation of the membranes proteins.

There is also substantial interest in developing methods for prophylactically treating herpes infections. Since viral infections are normally resistant to treatment with antibiotics, other techniques which do not have significant side effects are of great interest.

DESCRIPTION OF THE RELEVANT LITERATURE

Eberle and Mou, *J. of Infectious Diseases* (1983) 148:436-444, report the relative titers of antibodies to individual polypeptide antigens of HSV-1 in human sera. Marsden et al., *J. of Virology* (1978) 28:624-642, report the location of a gene for a 117 kilodalton (kd) glycoprotein to lie within 0.35-0.40 map units on the genetic map of HSV by intertypic recombination between HSV-1 and HSV-2. Ruyechan et al., ibid. (1979) 29:677-697, also report the mapping of glycoprotein B gene to lie between 0.30-0.42 map units. Skare and Summers, *Virology* (1977) 76:581-595, report endonuclease cleavage sites for EcoRI, XbaI and HindIII on HSV-1 DNA. Roizman, *Ann. Rev. Genetics* (1979) 13:25-57. reports the organization of the HSV genomes. DeLuca et al., *Virology* (1982) 122:411, map several phenotypic mutants thought to lie in the gB1 structural gene between 0.345 to 0.368 map units.

Subunit vaccines extracted from chick embryo cells infected with HSV-1 or HSV-2 are described in U.S. Pat. Nos. 4,317,811 and 4,374,127. See also, Hilfenhaus et al., *Develop. Biol. Standard* (1982) 52:321-331, where the preparation of a subunit vaccine from a particular HSV-1 strain (BW3) is described. Roizman et al., ibid, (1982) 52:287-304, describe the preparation of nonvirulent HSV-1 x HSV-2 recombinants and deletion mutants which are shown to be effective in immunizing mice. Watson et al., *Science* (1982) 218:381-384, describe the cloning and low level expression of the HSV-1 gD gene in *E. coli*, as well as expression of a cloned fragment by injection into the nuclei of frog oocytes. They also present the nucleotide sequence for the gD gene. Weis et al., *Nature* (1983) 302:72-74, report higher level expression of gD in *E. coli*. This polypeptide elicits neutralizinp antibodies in rabbits. Berman et al., *Science* (1983) 222: 524-527, report the expression of glycoprotein D in mammalian cell culture. Lasky et al., *Biotechnology* (June 1984) 527-532, report the use of this glycoprotein D for the immunization of mice. Cohen et al., *J. Virol.* (1984) 49:102-108, report the localization and chemical synthesis of a particular antigenic determinant of gD, contained within residues 8-23 of the mature protein.

"Therapeutic" use of preparations of membrane proteins from HSV-infected cells for post-infection vaccine in humans are reported by Dundarov, S. et al., *Dev. Biol. Standard* (1982) 52:351-357; and Skinner, G. R. B. et al., ibid. (1982) 52:333-34.

SUMMARY OF THE INVENTION

Novel vaccines and therapeutic compositions against Herpes Simplex Virus Types 1 and 2 and methods for their production and use are provided. These vaccines and therapeutics employ a combination of virus specific polypeptides produced by recombinant DNA technology. Particularly, HSV gB and gD were produced in modified mammalian and yeast hosts and employed in combination as vaccines. They may be used for the prophylaxis and treatment of herpes simplex viral infections in animals, including humans.

Accordingly, one aspect of the invention is a vaccine which contains an immunogenically active HSV gB polypeptide in combination with an immunogenically active HSV gD polypeptide. These immunogenically active polypeptides are prepared by expressing recombinant DNA constructs in eukaryotic host cells. The polypeptides are present in an amount which is effective to produce an immune response in a mammal.

Another aspect of the invention is a method for preparing a vaccine against herpes simplex virus. This method consists of synthesizing immunogenically active HSV gB and gD polypeptides in eukaryotic hosts via the expression of recombinant DNA constructs, isolating the polypeptides, and formulating them in immunogenic amounts with a pharmacologically acceptable carrier.

Another aspect of the invention is a method for immunizing a mammal against herpes virus, wherein the mammal is vaccinated with the above described vaccine. The vaccination may occur before primary infection, in which case it acts to prevent primary infection, or after primary infection, in which case it acts to prevent or alleviate recurrent symptoms of the infection.

Yet another aspect of the invention is a method for producing an immunogenically active HSV gD2 polypeptide. This method consists of growing mammalian cells which have been modified to include a DNA construct capable of expression in mammalian cells. The DNA construct contains an oligonucleotide encoding an immunogenically active gD2 polypeptide; the oligonucleotide is flanked by transcriptional and translational regulatory sequences, wherein at least one of the regulatory sequences is not of HSV origin. The DNA construct is joined to a system for its replication in the host mammalian cells. The polypeptide produced by the mammalian cells is harvested and isolated.

BRIEF DESCRIPTION OF THE DRAWINGS

FIG. 4 shows the DNA amino acid sequences of gB1 and gB2.

FIG. 7 is a physical map of HSV-2, indicating coding regions for gB2.

FIG. 17A shows the effect of immunization with herpes virus glycoproteins on the rate of recurrent herpetic infections.

FIG. 17B shows the difference in weekly recurrence rates between control and immunized guinea pigs.

DESCRIPTION OF THE SPECIFIC EMBODIMENTS

Vaccines

Figure 1:
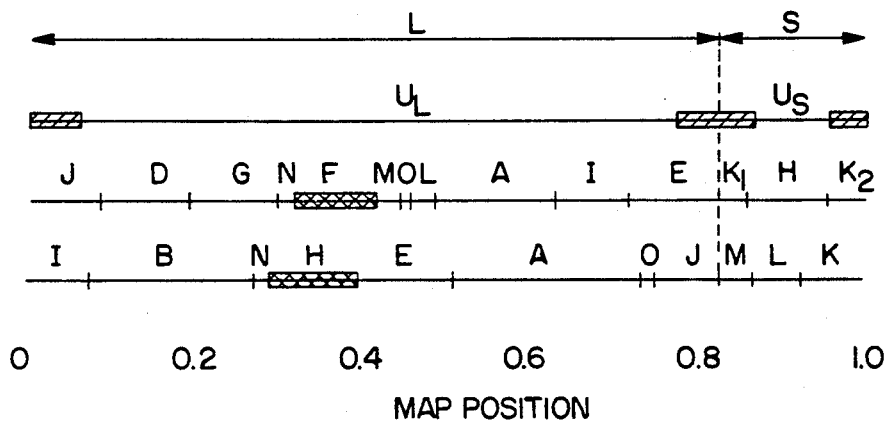
FIG. 1 shows physical maps of HSV-1 and HSV-2, an EcoRI cleavage map for the prototype isomer arrangement, and a HindIII restriction map of HSV-2.

The vaccines of the invention employ recombinant HSV glycoproteins B and D of both types 1 and 2. Mature (full length) gB and gD proteins may be used as well as fragments, precursors and analogs that are immunologically equivalent (i.e., provide protection against infection) to the mature proteins. As used in the claims, the terms "glycoprotein B polypeptide" and "glycoprotein D polypeptide" are intended to include such fragments, precursors, and analogs. The recombinant gB and gD polypeptides are produced in eukaryotic cells preferably yeast or mammalian cells, most preferably mammalian cells. Fragments will be at least about 15 amino acids and preferably at least about 30 amino acids in length. The vaccines may comprise a mixture of type 1 polypeptides, a mixture of type 2 polypeptides or a mixture of both type 1 and type 2 polypeptides.

The mixtures of gB and gD polypeptides may be used neat, but normally will be used in conjunction with a physiologically and pharmacologically acceptable medium, generally water, saline, phosphate buffered saline, sugar, etc., and may be employed with a physiologically acceptable adjuvant, e.g., aluminum hydroxide, muramyl dipeptide derivatives and the like. As shown in Example 6.4, a variety of adjuvants may be efficacious. The choice of an adjuvant will depend at least in part on the stability of the vaccine containing the adjuvant, the route of administration, the efficacy of the adjuvant for the species of the individual being vaccinated, and, in humans whether or not the adjuvant has been approved for human use by the Federal Drug Administration. The vaccine may be delivered in liposomes and/or in conjunction with a immunomodulators such as interleukin 2. The vaccines may be administered by any convenient parenteral route, e.g., intravenously, intraarterially, subcutaneously, intradermally, intramuscularly or intraperitoneally. It may be advantageous to administer split doses of vaccines which may be administered by the same or different routes. The vaccines may be administered prior to, and/or subsequent to an initial infection with herpes simplex virus.

Glycoproteins B and D may be used without modification. However, when smaller related polypeptides are used, such as fragments or the like, and their molecular weight is less than about 5000 daltons, e.g., 1500 to 5000 daltons, modification may be required to elicit the desired immune response. The smaller haptens should be conjugated to an appropriate immunogenic carrier such as tetanus toxoid or the like.

It is also possible to link short DNA fragments encoding the gB or gD polypeptides to genes expressing proteins from other pathogenic organisms or viruses. In this way, the resulting fused proteins may provide immunity for more than one disease.

The total amount of recombinant gB and gD polypeptides employed per dose will usually be about 10 μg to 2 mg/kg, more usually about 50 μg to 1 mg/kg and particularly about 100 to 500 μg/kg of host body weight. The ratio of gB to gD in the vaccine will usually be about 0.1:1 to 10:1, more usually about 0.5:1 to 10:1 and preferably about 0.5:1 to 5:1. The dose may be administered repeatedly at daily to weekly intervals, and usually two to four week intervals, usually not more than about two to ten times.

Recombinant Glycoprotein B

The preparation of recombinant gB polypeptides is described in detail in parent application Ser. No. 597,784, the disclosure of which is incorporated herein by reference. A brief description of the materials and methods used to make recombinant gB polypeptides follows.

FIG. 4 in the Experimental section provides the nucleotide sequence for gB1 strain Patton, as well as the amino acid sequence coded by the nucleotide sequence. FIG. 4 also shows the substantial homology between gB1 and gB2. The nucleotide sequence may be varied in numerous ways. Various fragments may be employed having independent functions, which may be joined to proteins other than the mature gB. In addition, the various codons may be modified so as the encode for the same amino acids, but provide more efficient expression in accordance with the nature of the host. For example, the codons may be modifed in accordance with the frequency of occurrence of a particular codon in one or more proteins or groups of proteins, e.g., glycolytic proteins, which contribute to a high proportion of the total proteins of a particular host, e.g., yeast. In some instances one or more codons may be modified to code for a different amino acid, substituting one amino acid for another amino acid, where the effect of the change is not detrimental to the immunogenicity of the protein or to other biological factors of interest. It may be desirable in some instances to add amino acids to the N-terminus or C-terminus, where such additional amino acids may provide for a desired result. This can be readily achieved by providing for additional codons at the 5'- or 3'-termini of the sequence encoding the mature gB1 or its precursor. In addition, while the amino acid sequence of gB2 may differ from that of gB1 by as much as 20 number percent, other strains of HSV-1 or of HSV-2 will have gB glycoproteins the same as or similar to gB1 strain Patton or gB2 strain 333, respectively, usually differing by fewer than 5 number percent, more usually differing by fewer than 2 number percent, and frequently differing by fewer than 0.5 number percent amino acids from the amino acid sequence of gB1 strain Patton or gB2 strain 333.

The gB1 sequence, particularly gB1 strain Patton, may be divided into four domains beginning at the N-terminus of the protein: first hydrophobic region extending from amino acid 1 to about amino acid 30: a region of variable polarity extending from the first hydrophobic region to about amino acid 726; a second hydrophobic region extending from said variable polarity region to about amino acid 795, and a second variable polarity region extending to the C-terminus at amino acid 904.

Since gB is a membrane glycoprotein, based on analogy with other glycoproteins, the first hydrophobic region may be considered the signal leader sequence directing secretion and/or membrane location. The first sequence of variable polarity would then be external to the membrane and serve as the recognition sequence, to the extent that gB serves as a receptor for another protein or as an immunogen in a vaccine. The second hydrophobic sequence may serve as a transmembrane integrator sequence (often termed the "anchor"), which can be joined to other amino acid sequences to bind them to a membrane. The second variable polarity amino acid sequence would be expected to be in the cytoplasm and, to the extent that a receptor is external to the transmembrane integrator sequence, may serve to modulate one or more cytoplasmic processes.

The polynucleotide sequence encoding for the precursor to gB or functional fragments thereof may be cloned and expressed by inserting the polynucleotide sequence into an appropriate expression vector and introducing the resulting expression product construct into a compatible host. The coding fragments will be less than about 0.1 map unit, usually less than about 0.05 map unit where 1.0, map unit is the size of the entire HSV genome. The expression vector may be a low or high multicopy vector which exists extrachromosomally or integrated into the genome of the host cell and may provide for secretion or excretion of the polypeptide of interest or retention of the polypeptide of interest in the cytoplasm or in the membrane. A large number of expression vectors have been published in the literature and are generally available for use in eukaryotic hosts, including yeast, e.g., *S. cerevisiae,* and a wide variety of immortalized mammalian cells, such as mouse cells, monkey cells, hamster cells, e.g., 3T3, Vero, Chinese Hamster Ovary cells (CHO), etc or primary cell lines. Depending upon the host, where secretion is desired, either the native or unnatural secretory leader sequence may be employed. The processing signals for cleavage of the secretory leader may be the natural signals or the signals associated with the unnatural secretory leader or both in tandem.

Figure 2:
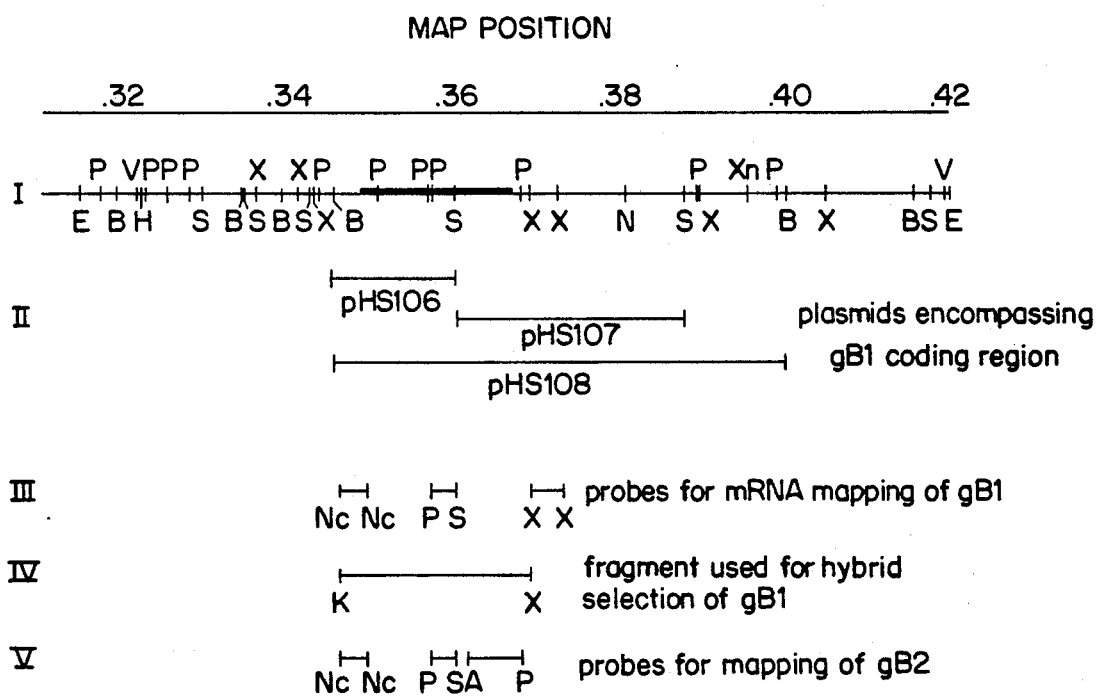
FIG. 2 shows a restriction map of the region of HSV-1 map which encodes gB1.

In order to obtain the polynucleotide sequence encoding for gB1-Patton, the location of the gB1 coding sequences on the EcoRI restriction fragment F was mapped. Three subfragments of the F fragment were isolated and subcloned into pBR322 (FIG. 2). DNA fragments from these subclones were then used to probe Northern blots of Poly A+ mRNA isolated from HSV-1 infected cells. Fragments which hybridized to mRNA of the size expected for gB were presumed to lie within the gB coding region. The direction of transcription of gB was also elicited by determining which strand of the DNA probes hybridized with the mRNA. To verify the identity of the gB sequence, DNA fragments were used to hybrid-select HSV-1 mRNA, which was then translated in vitro and the resulting proteins analyzed for gB using a gB specific antibody.

The gB1 coding fragment may now be manipulated in a variety of ways, including restriction mapping and sequencing, so as to establish the restriction sites and the open reading frame regions for expression. The DNA sequence may then be restricted to provide for a sequence encoding the entire gB precursor or fragments thereof. These sequences may then be inserted into an appropriate expression vector having appropriately positioned transcriptional and, as appropriate, translational signals. This can be achieved by filling in overhangs and providing for blunt-end ligation, by employing adapters, or the like.

It is of particular interest to introduce the gene in tandem with a gene capable of amplification. Convenient genes include the dihydrofolate reductase (dhfr) gene, which can be amplified by employing methotrexate, where the dhfr gene and flanking regions are reiterated; and metallothioneins which can be amplified with heavy metals, e.g., copper, or the like. The expression product construct can be introduced into an appropriate host by any convenient means, including transformation, transfection, calcium phosphate precipitation, etc.

The host cells may then be stressed with the appropriate biocide at levels which select for amplification of the particular gene. The cells may then be cultured and grown to provide efficient production of the desired polypeptide.

Following the procedure described above, the polynucleotide sequence coding for gB2 from a HSV-2 strain 333, both precursor and mature, may also be isolated, cloned, and manipulated to provide a construct which may result in expression in one or more hosts. In view of the availability of fragments coding for gB1-Patton, these fragments may be used as probes for either localization of gB2 encoding DNA segments to specific HSV-2 restriction fragment clone(s) or isolation of gB2 mRNA from infected host cells. Conveniently, a plurality of probes may be employed coding for different regions of the gB1 gene. One selects for either positive DNA fragment(s) or abundant mRNA having approximately the right size which hybridizes to the probe(s). The mRNA may then be reverse transcribed to provide cDNA and/or may be used for hybridization to fragments of the HSV-2 genome to confirm their gB2 encoding function. Where necessary, more than one cloned fragment comprising portions of the gB2 structural gene may be manipulated and joined to provide the entire coding region and flanking region(s), as appropriate. The coding region may then be introduced into an expression vector.

Recombinant Glycoprotein D

The preparation of recombinant gD1 is described in detail in parent application Ser. No. 631,669, the disclosure of which is incorporated herein by reference. A brief description of the materials and methods used to make recombinant gD polypeptides follows. A detailed description of the preparation of recombinant gD2 is presented in the Experimental section below.

Polypeptides which are immunologically cross-reactive with naturally occurring glycoprotein D are produced in eukaryotic hosts, e.g., yeast and mammalian cells, such as CHO cells by recombinant DNA methodology. Production in eukaryotes provides the advantages associated with eukaryotic hosts, e.g., post-translational modification and/or secretion. The gD polypeptides may be produced from relatively short synthetic DNA fragments encoding for at least about 9 amino acids to provide haptens useful for eliciting an immune response specific for gD.

The gD DNA fragments may be of natural or synthetic origins. The natural gD gene of HSV-1 is located on the viral genome between the short internal repeat ($IR_S$) sequence and short terminal repeat ($TR_S$) sequence at the 3'-end thereof. Coding for the mature protein is found on an approximately 1.6 kbp fragment located on a 2.9 kbp SacI restriction fragment of the genome. The entire coding region for the mature protein is located within a HindIII-NruI fragment of the 2.9 kbp SacI fragment. The naturally occurring gD gene may be employed with or without modification. Regions of the gene may be deleted and/or joined to other DNA fragments as desired. The gD DNA fragments may be inserted in expression vectors and expressed using similar materials and procedures as are described above for the expression of gB DNA. The preparation, cloning and expression of particular fragments of the naturally occurring gD gene are described in detail in the Experimental section hereinafter.

The following examples are offered by way of illustration and not by way of limitation. In the examples: Section 1 describes general procedures used to make the recombinant proteins; Section 2 describes the preparation of recombinant gB1; Section 3 describes the preparation of recombinant gB2; Section 4 describes the preparation of recombinant gD1; Section 5 describes the preparation of recombinant gD2: and Section 6 describes vaccine studies using mixtures of gB and gD polypeptides.

EXAMPLES

1. Materials and Methods

The HSV-1 strain Patton and HSV-2 strain 333 viable stocks are available from Dr. Richard Hyman, Hershey Medical Center, Hershey, Pa. These viruses can be propagated in Vero cells available from Dr. Evelyn Linnette, Viro Labs, Emeryville, Calif., or from the American Type Tissue Culture Laboratory, the propagation being performed in accordance with standard procedures. A library of HSV-1 Patton EcoRI DNA fragments (Kudler et al., *Virology* (1983) 124: 86–99) cloned in the EcoRI site of the plasmid pACYC184 (Chang and Cohen, *J. Bacteriology* (1978) 134:1141) can be obtained from Dr. Hyman or be independently prepared in accordance with conventional techniques. Two HSV-2 333 clones can also be obtained from Dr. Hyman, namely the HindIII fragments H and L inserted into the HindIII site of pBR322 (Sutcliffe, *Nucleic Acids Research* (1978) 5:2721).

The dhfr deficient CHO cell line was obtained from Dr. Y. W. Kan (University of California at San Francisco). This cell line was originally described by Urlaub and Chasin, *Proc. Natl. Acad. Sci. USA (*1980) 77:4216–4220. For nonselective conditions, these cells were grown in Ham's F-12 medium (available from Gibco, cat. no. 176) supplemented with 10% fetal calf serum, 100 U/ml penicillin, 100 μg/ml streptomycin and 150 μg/ml L-proline. Selective media was DME supplemented with 10% dialyzed fetal calf serum plus penicillin, streptomycin and 150 μg/ml L-proline. For methotrexate (MTX) selection, concentrated MTX stocks were prepared from MTX obtained from Lederle and added to the above DME selective media immediately before use.

1.1 Cloning

All DNA manipulations were done according to standard procedures. See, Maniatis et al., *Molecular Cloning,* CSH (1982). Restriction enzymes, T4 DNA ligase, *E. coli* DNA polymerase I Klenow fragment, and other biological reagents were purchased from Bethesda Research Laboratories or other indicated commercial suppliers and used according to the manufacturer's directions. Double-strand DNA fragments were separated on 1% agarose gels and isolated by electroelution.

1.2 Isolation of RNA, Northern blot analysis and hybrid-selected translation Total RNA was prepared from HSV-1 or HSV-2 infected Vero cells at 6 hrs after infection with multiplicity of 10 virus per cell. Cell monolayers were washed, incubated with extraction buffer and processed as described (Pachl et al., Cell (1983) 33:335–344). Poly $A^+$ RNA was prepared by passing 2 mg total RNA over a 3 ml column of oligo dT cellulose (obtained from Collaborative Research) in 500 mM NaCl, 10 mM Tris HCl pH 7.5, 1 mM EDTA, 0.1% SDS, then washing the column in 100 mM NaCl. 10 mM Tris HCl pH 7.5, 1 mM EDTA, 0.1% SDS and then eluting the poly A fraction with 10 mM Tris HCl pH 7.5. 1 mM EDTA, 0.1% SDS.

For Northern blot analysis, poly A+ RNA was denatured with glyoxal (McMaster et al., *Proc. Natl. Acad. Sci. USA* (1977) 74:4835–4838), fractionated by electrophoresis on 1% agarose gels, transferred to nitrocellulose paper (Thomas, ibid. (1980) 77:5201–5205) and hybridized with $^{32}$P-labeled probes.

The details of the methods used for hybrid-selected translations have been described previously (pachl et al., *Cell* (1983) 33:335–344). DNA filters were prepared using either 3 μg of a 3.5 kb Xho-Kpn fragment encoding gB or 2 μg of a 3.0 kb SstI-SstI fragment encoding HSV-1 gD. The filters were incubated with 40 μg of poly A+ RNA from HSV-1 infected cells. Bound RNA was eluted and translated in a reticulocyte cell-free system (Pachl et al., *J. Virol.* (1983) 45:133–139). Translation products were analyzed on 12.5% SDS polyacrylamide gels (Laemmli, *Nature* (1970) 227:689).

1.3 DNA transfections

Transformation of COS 7 cells (Gluzman, *Cell* (1981) 23:175–182) or dhfr deficient CHO cells (Urlaub and Chasin, (1980) supra) was carried out using the procedure of van der Eb and Graham (*Methods in Enz.* (1980) 65:826–839), as modified by parker and Stark (*J. of Virol.* (.1979) 31:360–369). except that carrier DNA was omitted. A calcium phosphate precipitate of plasmid DNA was prepared by mixing an equal volume of plasmid DNA, in 250 mM CaCl$_2$, with an equal volume of 2× concentrated HEPES-buffered saline (2×HBS) added dropwise (1×HBS is 0.14M NaCl, 5 mM KCl, 0.7 mM Na$_2$HPO$_4$, 2.8 mM glucose, 10 mM HEPES pH 7.0). After about 20 min incubation at room temperature, 1 ml of the calcium phosphate-DNA suspension (containing 15 μg DNA) was added to the media of cells, grown to 50% confluency on 10 cm plates. After 6–8 hrs the DNA-containing media was removed and the cells were incubated with 15% glycerol-1×HBS for 4 min. The cells were then grown in nonselective media (F12) for two days, after which the cells were split, i.e., subcultured, into selective media. Colonies of dhfr positive cells appeared after 10 days and were isolated after 14 days by removing the cells of a colony from a dish with a Pasteur pipette. The isolated cells were transferred to multiwell dishes for propagation.

1.4 In vivo labelling of cells and immunoprecipitation

To label with $^{35}$S-methionine, cells were grown to confluency in 3.5 cm dishes, washed once with pBS (0.14M NaCl, 2.7 mM KCl, 15.3 mM Na$_2$HPO$_4$) and then 0.5 ml of labeling media, DME (Dulbecco's Modified Eagle medium from Gibco, cat. no. 188G) without methionine plus 1% dialyzed fetal calf serum and 400 μCi/ml $^{35}$S-methionine (>1000 Ci/mmole) was added per dish. The cells were incubated for appropriate times at 37° C. At the end of the labeling period, the media was removed and the monolayer washed once with PBS. For a "cold" methionine chase, the labeling media was replaced with DME containing 2.5 mM methionine. For immune precipitation, cells were lysed in 0.1 ml of lysis buffer: 20 mM Tris-HCl pH 8, 100 mM NaCl, 1 mM EDTA, 0.5% Nonidet P40, 0.5% sodium deoxycholate, bovine serum albumin, 0.1% SDS, 1.0 mM phenylmethylsulfonyl fluoride, 10 mM benzamidine 1% aprotenin obtained from Sigma Chemical Company. The cell lysate was scraped into tubes, briefly vortexed, and then held at 4° C. for 5–10 min. Cell debris was removed by centrifugation and the clarified lysate stored at −70° C.

For immunoprecipitations, cell lystates, 0.1 ml, were precleared by incubation with normal serum for 30 min at 4° C. then 50 μl of a 20% solution of protein A Sepharose (PAS) (in lysis buffer) was added and incubation continued for 30 min at 4° C. with gentle rocking. The PAS was removed by centrifugation for 1 min at 14,000× g and 5 μl of HSV-1 polyclonal antibody (obtained from DAKO) or a gB-specific monoclonal antibody F3AB (obtained from Dr. John Oakes, University of South Alabama) was added. When the F3AB antibody was used, 0.1% SDS was omitted from the lysis buffer. After 30 min at 4° C., 75 μl of PAS was added and above. PAS-immune complexes were collected by centrifugation, washed 3× with lysis buffer lacking BSA and protease inhibitors and once with 0.12M Tris HCl pH 7.0. Immune precipitated proteins were released from PAS by boiling in SDS sample buffer, followed by analysis on 12% polyacrylamide gels. For immune precipitation of labeled proteins from cell media, the media was first clarified by centrifugation and then 1/10 volume of 10× lysis buffer was added and proteins were precipitated as described above.

1.5 Immunofluorescence

To analyze expression of gB or gD in COS cells or CHO clones, cells, grown in slide wells, were washed 3× with PBS, fixed with 100% methanol at −20° C. for 10 min followed by 3 more PBS washes and one wash with PBS plus 5% goat serum (GS). The fixed cells Were then incubated with the primary antibody (HSV-1 or HSV-2 polyclonal diluted 1/100 in PBS-5% GS) for 30 min at 37° C. The cells were then washed 3× in PBS-5% GS and then incubated at 37° C. for 30 min with the second antibody. FITC-conjugated goat anti-rabbit IgG (Cappel). diluted 1/10 in PBS-5% GS. After 4 washes in PBS-5% GS, the slides were mounted with coverslips using 50% glycerol—100 mM Tris HCl, pH 8 and observed in a Leitz microscope equipped with epifluorescent optics. Live cell immunofluorescence was carried out as described above except that the cells were initially washed once in PBS-5% GS directly followed by incubation with the first antibody. Before mounting with coverslips, the live cells were fixed with 5% formaldehyde in PBS. The fluorescein stained cells were photographed using a Kodak Ektachrome film (ASA 400).

1.6 ELISA Assay

The concentration of gB protein in CHO cell conditioned medium was measured by an indirect enzyme-linked immunosorbent assay (ELISA) using a preparation of purified recombinant gB as a standard. Aliquots of 50 μl of F3AB antibody diluted 1:1000 in PBS were adsorbed to the wells of a 96-well polyvinyl chloride plate (Dynatech Laboratories, Inc.) by incubation for 1 hr at room temperature. Excess antibody was removed by 3 washes with PBS-5% GS, 50 μl aliquots of media samples or the gB protein standard diluted in PBS+1% GS were added to the wells and incubated for 1 hr at room temperature. The plates were then washed 3 times with PBS+1% GS and followed by a third 1 hr incubation with 50 μl of rabbit anti-HSV-1 polyclonal antibody (obtained from DAKO) diluted 1:100 in the same buffer. Excess secondary antibody was removed by 3 washes with PBS+1% GS. Finally. 50 μl of goat anti-rabbit horseradish peroxidase-conjugated antibody (Boehringer Mannheim) diluted 1:500 in PBS+1% GS was added to each well for a 1 hr incubation. The wells were then washed once with PBS+1% GS, followed by 8 washes with PBS and then developed with 50 μl of 2,2'-azido-di[3-ethylbenz-thioazoline sulfonate] (Boehringer Mannheim) at a concentration of 1 mg/ml in 0.1M citric acid, pH 4.0, 0.003% $H_2O_2$. The color reaction was stopped after 5 minutes by the addition of 50 μl of 10% SDS and the absorbance was read at 414 nm in a microtiter plate reader.

The concentration of gD protein was measured in similar fashion except that purified recombinant gD was used as a standard, and 8D2, a gD-specific monoclonal antibody (Rector et al., *Infect. and Immun.* (1982) 38:168-174) replaced F3AB.

1.7 Yeast transformation

Yeast were transformed (Hinnen et al., *Proc. Natl. Acad. Sci.* 75:1929, 1978) and grown using a variety of media including selective medium (yeast nitrogen base without leucine); YEPD medium, containing 1% (w/v) yeast extract, 2% (w/v) peptone and 2% (w/v) glucose, and others as appropriate and/or detailed below. Plating medium contained 2% (w/v) agar and transformation medium 3% top agar.

2. Glycoprotein B1

2.1 Isolation, cloning and characterization of the gB1 gene

To isolate the gene for the glycoprotein gB1, DNA fragments spanning map coordinates 0.345 to 0.40 within the EcoRI F restriction fragment of the HSV-1 strain Patton (Skare and Summers, *Virology* (1977). 76:581-595) were subcloned in the plasmid pBR322. These fragments were prepared from the appropriate restriction digests of the EcoRI region in the plasmid pACYC184, separated by electrophoresis on a 1% agarose gel in TAE buffer (0.04M Tris-acetate, 0.002M EDTA) and electroeluted. The isolated fragments were ligated into pBR322 which had also been previously cut with the appropriate restriction enzyme and treated with alkaline phosphatase. A restriction map for the entire HSV-1 genome is shown in FIG. 1, and a more detailed map of the region which was subcloned is shown in FIG. 2. Referring to FIG. 1, the conventional map is shown in the first two lines (Roizman, 1979). The dotted line indicates the L-S junction. The restriction enzyme cleavage map for EcoRI for the prototype isomer arrangement is shown in the third line (Skare and Summers, 1977; Roizman, 1979) with the EcoRI fragment F denoted by the cross-hatched box. For HSV-2, the HindIII restriction map is shown in line 4 (Roizman, 1979) with the HindIII fragment H cross-hatched. One map unit corresponds to approximately 98.9 megadaltons or 148.9 kbp of DNA for HSV-1 and 105.6 megadaltons or 160.5 kbp of DNA for HSV-2.

Referring to FIG. 2, the restriction enzyme sites shown in the detailed map line (I) are E, EcoRI; B, BamHI; S, SalI; p, PstI, X, XhoI from DeLucca et al., 1983; N, NdeI; Xn, XmnI; V. EcoRV. The BstEII site mapped by DeLucca et al. at 0.355 is missing in this strain and there is a new PstI site at 0.357. Line II shows three plasmid subclones which encompass the gB1 coding region. They are pHS106, which extends from the BamHI site at 0.345 to the SalI site at 0.360; pHS107 which extends from the SalI site at 0.36 to the SalI site at 0.388; and pHS108 which is a BamHI fragment extending from 0.345 to 0.40 map units. Line III indicates three probes used for mRNA mapping of gB1; line IV indicates the fragment used for hybrid selection; and line V shows those probes used to locate the gB2 gene (see below). The additional restriction sites used to generate these fragments are Nc, NcoI; K, KpnI; and A, AluI.

To locate the gB1 coding region within the EcoRI F fragment, Northern blots of poly A+ mRNA isolated from HSV-1 infected Vero cells were probed with the DNA fragments indicated on the detailed map isolated from plasmids pHS106 and pHS107. When HSV-1 mRNA was probed with a 0.56 kb PstI-SalI fragment isolated from pHS106, a 3 kb mRNA was the major species detected. When the same blot was probed with a 0.49 kb NcoI fragment, which maps about 1 kb upstream from the PstI-SalI fragment, hybridization to a 3 kb mRNA, the presumptive gB1 mRNA, was also detected. This suggests that the gB1 coding sequences extend at least 1 kb to the left of the PstI-SalI fragment. The 3 kb mRNA does not extend beyond the first XhoI site downstream from the PstI-SalI fragment, since the 0.5 kb KhoI-XhoI fragment does not hybridize to this mRNA. The direction of transcription of the gB1 transcription unit is right to left (3'←5') as evidenced by hybridization of only the 5'→3' oriented strands of the PstI-SalI and NcoI-NcoI fragments (cloned in M13) to the 3 kb gB1 mRNA.

Hybrid selected translation was performed by hybridizing HSV-1 poly A+ mRNA with a 3.2 kb KpnI-XhoI fragment, which encompasses the region indicated as encoding gB1. When the bound mRNA was eluted and translated in vitro, a 100 kd protein, similar in size to gB1 from HSV-1 infected Vero cells, was detected. Confirmation of the identity of the 100 kd protein was achieved by immunoprecipitation with a gB1-specific monoclonal antibody. Several other proteins were also detected by hybrid selection using the KpnI-XhoI fragment, probably the result of non-specific hybridization of mRNAs due to the high G+C content of the DNA. A similar pattern of proteins was seen when the same RNA was selected with a 3.0 kb SstI-SstI DNA fragment encoding HSV-1 glycoprotein gD, except that the 100 kd gB protein was not detected. This result indicates that gB is specific to the XhoI-KpnI fragment.

Figure 3:
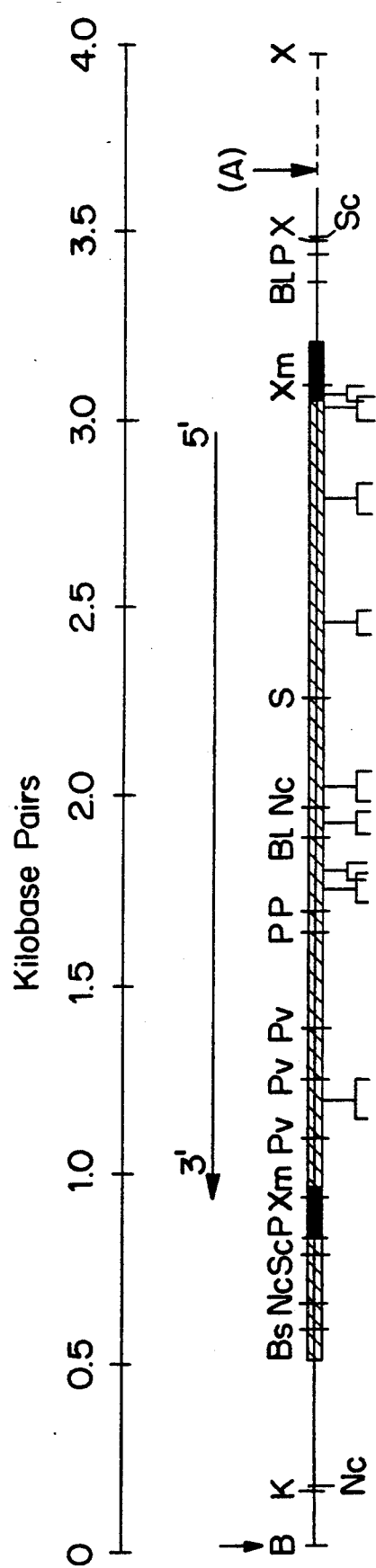
FIG. 3 is a restriction map of gB1 coding region.

FIG. 3 is a restriction map of a 3.95 kb DNA fragment, which extends from a BamHI restriction site at 0.345 to an XhoI site at 0.373 map units. The open reading frame for gB1 is indicated by the box and the direction of transcription is from right to left as shown. The actual coding region covers map units 0.348 to 0.367. The DNA sequence from the BamHI site to a non-unique AluI site at nucleotide number 3640 is shown with the AluI site indicated by the (A). The restriction sites shown include B, BamHI; B1, BalI; Bs, BstEII; K, KonI; Nc, NcoI; p, PstI; Pv, PvuII; S, SalI; Sc, SacI, X, XhoI; Xm, Xma3. Restriction sites are not shown for the right-hand end from the AluI site to the terminal XhoI site. Potential glycosylation sites and hydrophobic anchor and signal regions (solid box) in the product gB1 protein are noted.

The DNA sequence was determined from the BamHI site to a non-unique AluI site at nucleotide residue number 3640 using the M13 dideoxynucleotide synthesis method of Sanger. Both DNA strands across the coding region were sequenced. The entire DNA sequence was compiled from overlapping restriction fragments such that the sequence was read across all restriction fragment joints. FIG. 4 shows the DNA sequence for gB1 (line 3); the predicted amino acid sequence for gB1 is shown below the DNA sequence (line 4).

It should be noted that the amino acid sequence and DNA sequence for gB1 presented in FIG. 4 differs from that originally presented in Table 1 of the parent application, Ser. No. 597,784, filed Apr. 6, 1984, the disclosure of which is hereby incorporated by reference. The DNA sequence in said Table 1 contains an error in that an additional nucleotide (G) is listed at position 607; this nucleotide has been deleted in FIG. 4, which presents the corrected DNA sequence. The amino acid sequence in said Table 1 was deduced from the incorrect DNA sequence presented therein; the sequence as presented in said Table 1 is incorrect because of the shift in reading frame due to the additional nucleotide. FIG. 4 presents the amino acid sequence based upon the corrected DNA sequence; the amino acid sequence in FIG. 4 has been confirmed by amino acid sequencing of the N-terminal region of gB1. This change in the deduced amino acid sequence also results in correction concerning the deduced position of the hydrophobic and hydrophilic regions, and the glycosylation sites in the gB1 molecule. The deductions based upon the corrected sequence are presented below.

Primer extension, using a 22 bp oligonucleotide (residues 473-494) indicated that the 5'-end of gB1 mRNA was located at residue 188. The CAT and TATA transcriptional regulatory signals are presumptively at residues 55-62 and 125-131. Starting at the ATG at residues 438-440, there is an open reading frame of 2712 nucleotides which terminates at a TGA stop codon. Two presumptive polyadenylation signals are located in a 3'-non-coding region at residues 3166-3173 and 3409-3416.

The observed amino acid sequence is characteristic of a membrane protein. There is a very hydrophobic region near the carboxy terminus stretching from amino acid residue number 726 to 795, a 69-amino acid sequence which may span the membrane. At the N-terminus the first 30 amino acids are primarily hydrophobic. This hydrophobic amino acid domain precedes a region with a high concentration of charged or hydrophilic amino acids. The hydrophobic sequence at the N-terminus may serve as a secretory leader or signal sequence followed by processing signals for cleavage and removal of the secretory leader. The hydrophobic region near the C-terminus can serve as a transmembrane integration sequence for binding the protein to the cell membrane.

The sequence data is also suggestive that there are nine possible N-linked glycosylation sites as defined by the sequence asn-X-thr/ser (see also FIG. 3) within the hydrophilic, external domain. If the first 30 amino acids are removed by processing and each of the potential N-linked glycosylation sites are utilized with the addition of an average 2 kd of carbohydrate per site, the molecular weight of the mature protein would be approximately 123 Kd.

2.2 Expression of gB1 in mammalian cells

Employing the above DNA sequence or fragment thereof, expression was achieved as follows. The vector employed is a mammalian expression vector, referred to as pSV1/dhfr. This 5.63 kb plasmid contains 2.8 kb of *E. coli* plasmid pBR328 sequences, including the ampicillin-resistance β-lactamase gen and the origin of replication. The vector also contains a selectable mammalian cell marker, the mouse dihydrofolate reductase cDNA gene (dhfr) (Nunberg et al., *Cell* (1980) 19:355) linked to the SV40 early promoter, which directs the transcription of dhfr. Additional SV40 sequences, including t antigen splice donor and splice acceptor sites and the polyadenylation sites for early transcripts, are included downstream from the dhfr gene within a 1.65 kb BolII-EcoRI fragment.

Figure 5:
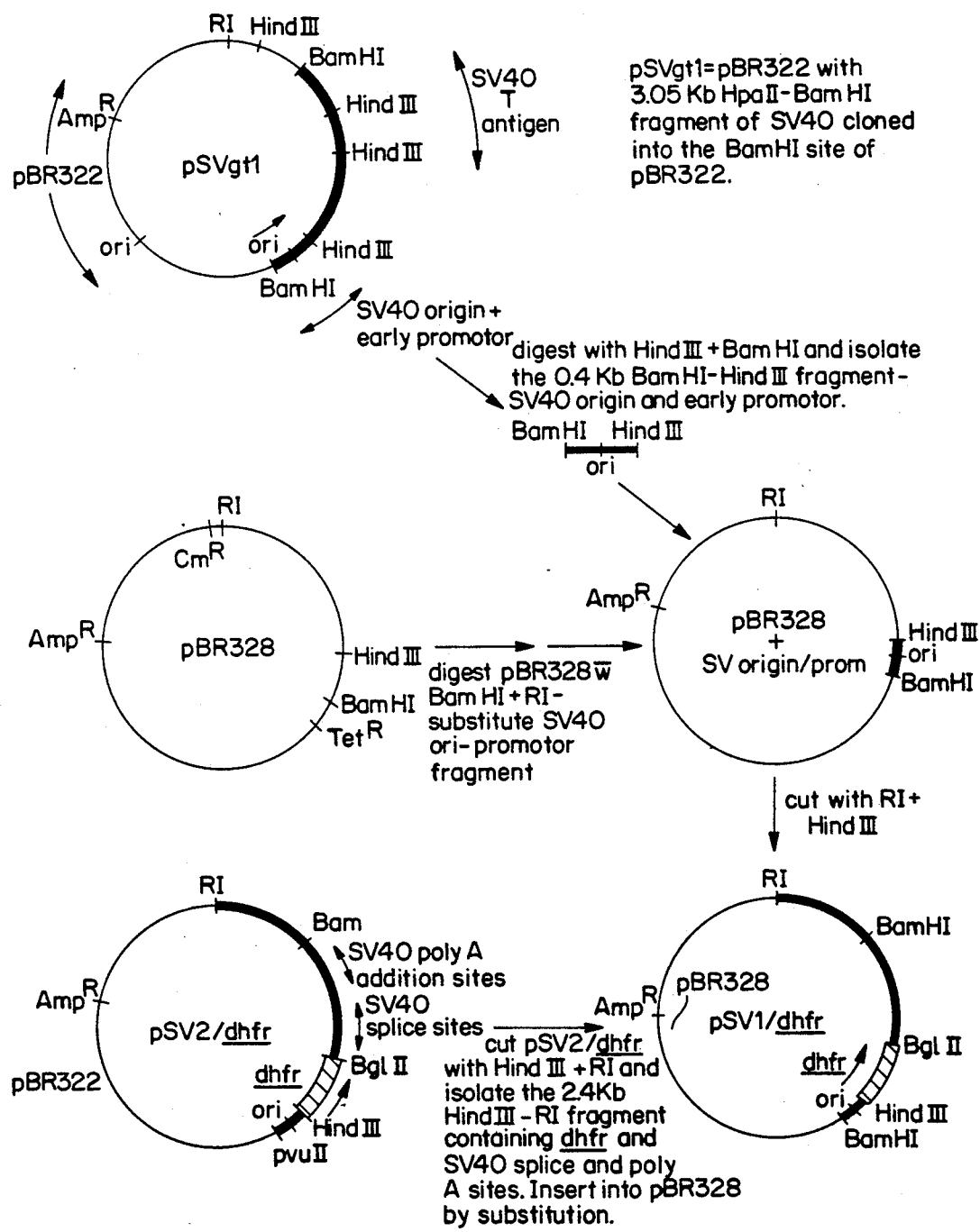
FIG. 5 is a flow diagram of the construction of pSV1/dhfr, a mammalian expression vector.

The plasmid pSV1/dhfr was constructed by first isolating the 0.4 kb BamHI-HindIII fragment encoding the SV40 origin and early promoter from plasmid pSVgt1. This SV40 fragment was then inserted into plasmid pBR328 by substituting this fragment for the small HindIII-BamHI fragment of pBR328. The dhfr cDNA gene and the SV40 splice sites and poly A sites of pSV1/dhfr were derived from plasmid pSV2/dhfr (Mulligan and Berg, *Mol. Cell Biol.* (1981) 1:854-864). The 2.4 kb HindIII-RI fragment encoding the dhfr-SV40 sequences was excised from pSV2/dhfr and inserted into the above pBR328 plasmid by substitution for the small HindIII-RI fragment of pBR328. The details of these constructions are given in FIG. 5.

Figure 6:
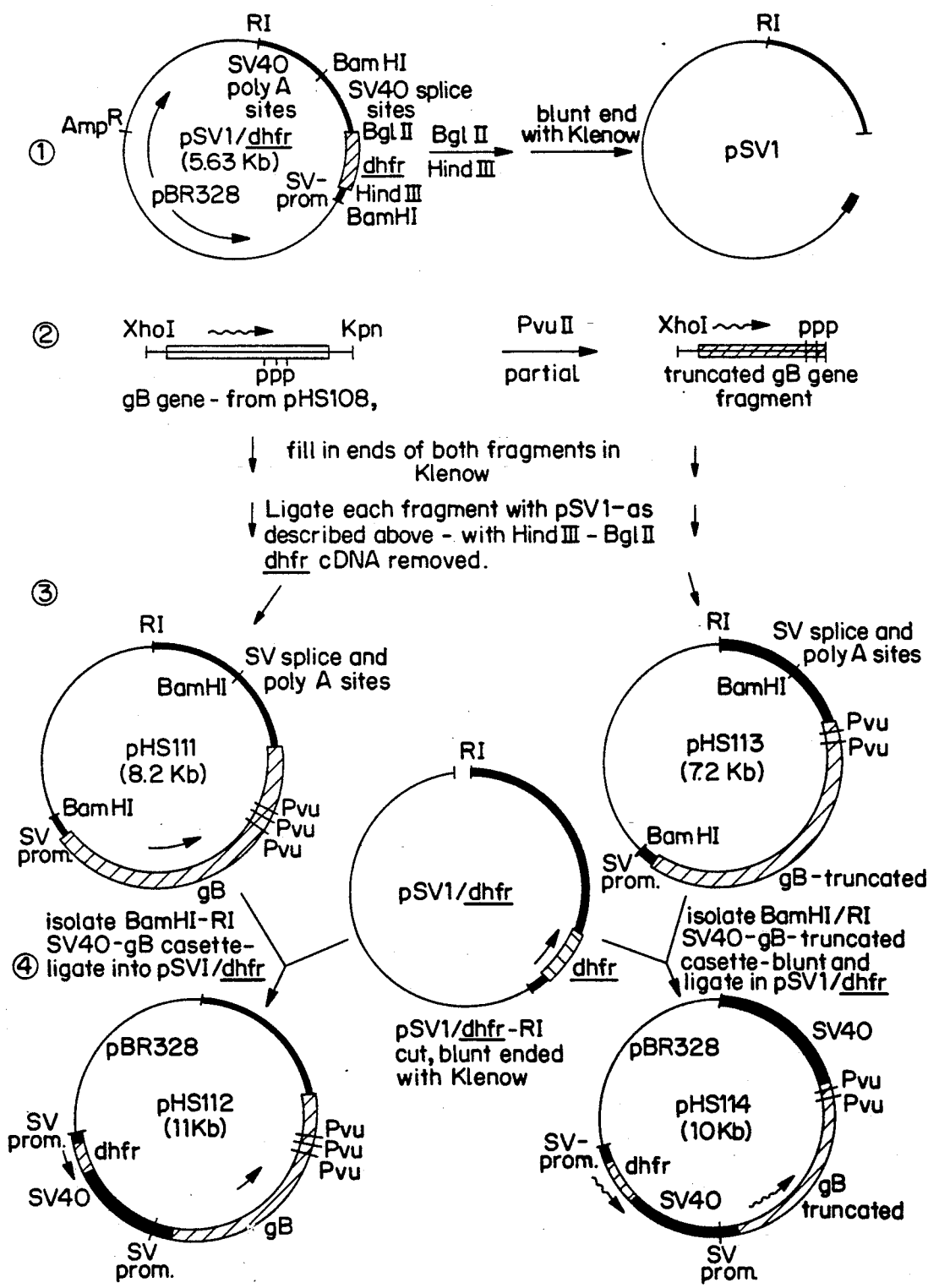
FIG. 6 is a flow diagram of the construction of plasmids pHS112 and pHS114, mammalian expression vectors for gB1.

To obtain expression of gB1, two pSV1/dhfr-gB plasmids, pHS112 and pHS114 were constructed (FIG. 6). pSV1/dhfr was restricted with BolI and HindIII excising the dhfr cDNA fragment. The resulting fragments are then blunt-ended by filling in the overhangs with the Klenow fragment of DNA polymerase I. A XhoI-KpnI HSV-I fragment containing the gB gene is isolated from pHS108. A portion is taken and partially digested with PvuII to generate a DNA sequence lacking the 3'-anchor region. The resulting truncated gB1 gene lacks 580 bp from the 3'-end of the gene. Both fragments are then blunt-ended with the Klenow fragment of pol I.

Each gB blunt-ended fragment is ligated into the BglII-HindIII restricted pSV1/dhfr vector to provide two sets each of constructs, with the gB1 gene in opposite orientations. The orientations having the Xho generated terminus proximal to the SV40 promoter, with the direction of transcription being from the SV40 promoter to the SV40 splice sites selected and designated pHS111 and pHS113 for the complete and truncated gB1 genes, respectively. The two plasmids are then completely digested with EcoRI and partially digested with BamHI to provide a cassette which includes the SV40 promoter, the gB gene and the SV40 splice and polyadenylation sites. These fragments are blunt-ended and ligated into EcoRI digested pSV1/dhfr vectors, so as to have the gB1 gene downstream from the dhfr gene and in the same orientation. The complete gB1 gene and trunctated gB1 plasmid constructs are designated pHS112 and pHS114, respectively.

The plasmids are then transfected into CHO cells deficient in dhfr using the calcium phosphate precipitation method as described in Materials and Methods. Transfected cells are selected by employing a selective medium lacking thymidine, purines and glycine. Cells were isolated by removal with a Pasteur pipette and propagated in multiwell plates. A number of clones were isolated which were shown to produce gB by immunofluorescence and radioimmunoprecipitation employing an HSV-1 polyclonal antibody or a monoclonal antibody specific for gB. Three cell clones, pHS112-1, pHS112-9 and pHS112-23, were isolated which synthesize an intracellular form of the complete gB protein. The gB made in these cells appears to be glycosylated, since higher molecular weight forms can be detected after a one hour pulse, followed by a 5 hr chase, as compared to nonchased cells and about 10% of the gB is secreted into the media. Five cell clones (pHS114-5, pHS114-6, pHS114-7, pHS114-11 and pHS114-12) expressing the truncated gB were also analyzed and shown to also secrete some gB into the media. One of these cell lines, pHS114-7, Was chosen for further amplification with MTX. Clones were initially selected at 0.01, 0.05, 0.10 and 0.3 μM MTX. Three clones levels of gB, as detected by immunofluorescence, were isolated from the 0.3 μM MTX selections. By radioimmune precipitation, these clones, pHS114-0.3 μM-6, 23 and 25, synthesize 2-3 times more gB during a 1 hr labeling with $^{35}$S-methionine than the unamplified clone, pHS114-7. pulse chase experiments indicate that at least 8% of the gB synthesized in these clones during a 1 hr pulse is secreted extracellularly by 5 hr.

Figure 16:
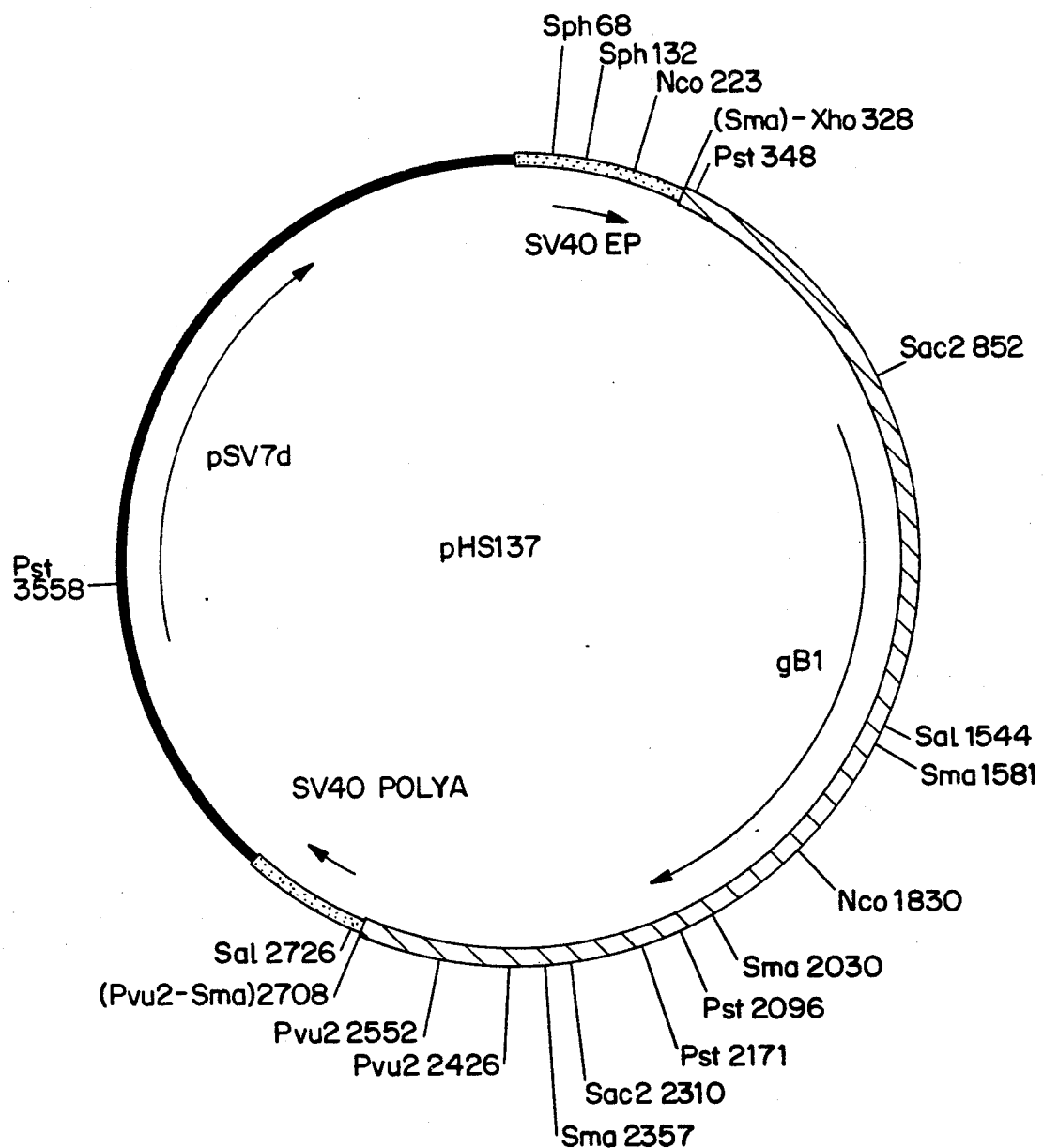
FIG. 16 is a map showing some significant features of the plasmid pHS137.

Expression was also achieved using the expression vector pHS137, a map of which is presented in FIG. 16. Plasmid pHS137 encodes a truncated gB1 protein which is 690 amino acids in length after cleavage of the signal sequence.

pHS137 was constructed by digestion of pHS108 (described in Section 2.1) with XhoI and BamHI, followed by isolation of a resulting 3.5 kb fragment. The ends of this fragment were repaired to blunt with Klenow.

The blunted XhoI-BamHI fragment was partially digested with PVUII, and DNA which migrated in gels as a 2098 bp band was iolated from the partial digest. The isolated XhoI-PVUII band was ligated into pSV7d which had been previously digested with SmaI, and the resulting DNA was used to transform *E. coli*. The resulting bacterial clones were screened for a plasmid with the proper orientation of the gB1 insert.

To obtain expression, pHS137 is cotransfected with the plasmid pADdhfr into dhfr deficient CHO cells. The resulting clones produce and secrete gB1. One such clone, pHS137-7-B-50 produces 6.91±1.53 μg/ml gB1 protein per 1-3×10$^7$ cells in 24 hours in a T75 culture flask containing 10 ml of complete medium.

2. 3 Expression of gB1 in yeast

Yeast expression was developed as follows. A cassette was prepared employing the glyceraldehyde-3-phosphate-dehydrogenase (GAPD4) promoter region and terminator region. A yeast gene library was prepared by inserting fragments obtained after partial digestion of total yeast DNA with restriction endonuclease Sau3A in lambda-phage Charon 28 (Blattner et al., *Science* (1977) 196:161-169). The phage library was screened with DNA complementary to the yeast GAPDH mRNA and the yeast GAPDH gene from one of these clones was subcloned as a 3.5 kb BamHI fragment in the BamHI site of pBR322 (pGAP-2). The GAPDH promoting-active fragments were isolated from these clones. A HhaI-HindIII fragment of about 350 bp containing the 3' portion of the promoter was obtained by: a) digestion of pGAP-2 with HinfI to generate an approximately 500 bp segment which includes the 3' part of the promoter and a region encoding the N-terminal amino acids of GAPDH; b) resection with Ba131 to yield a 400 bp fragment lacking the GAPDH coding region (3'-terminus 1 base upstream from the ATG initiator codon); c) addition of HindIII linkers; and d) cleavage with HhaI. A HindIII-HhaI fragment of about 700 bp containing the 5' portion of the promoter was ligated to the 350 bp HhaI-MindIII fragment and treated with HindlII. The resulting 1061 bp HindIII fragment was isolated by gel electrophoresis and cloned in pBR322 (pGAP347). The GAPDH promoter fragment in pGAP347 was isolated by cleavage with BamHI (within the 5' pBR322 flanking region) and partially with HindIII (at the 3' end of the promoter fragment) to provide a 1407 bp fragment containing a 1061 bp region of the GAPDH promoter region and 346 bp of pBR322. This procedure utilized digestion of 50 μg of the pGAP347 with 10 units each of BamHI and HindIII with the resulting fragment purified by preparative gel electrophoresis in 1% agarose.

A synthetic HindIII-XhoII adapter molecule containing the codon for the initiator met and a NcoI site for analysis was synthesized and had the following sequence:

AGCTTCCATGGA
AGGTACCTCTAG.

A third fragment was a XhoII-SacII fragment of 1187 bp containing the gB1 coding region.

A fourth fragment containing the GAPDH terminator fragment (approximately 900 bp) was isolated by SalI-BamHI digestion of a cloned fragment of the GAPDH gene with its 3' flanking region including the GAPDH termination region, so that a portion of the coding region is included with the termination region. The two fragments can be ligated together by means of a SacII-SalI adapter:

GGACAACTAG
CGCCTGTTGATCAGCT.

These five fragments together with the cloning vector were ligated as follows: First, the XhoII-SacII fragment (2 picomoles) was ligated to 100 picomoles of each of the two adapters (HindIII-XhoII, SacII-SalI) using T4 DNA ligase. The product was isolated by preparative gel electrophoresis in 1% agarose, providing a HindIII-SalI fragment. The HindIII-SalI fragment (0.25 picomoles) was ligated in a single step to the 1,407 bp BamHI-HindIII GAPCH promoter fragment (0.1 picomoles). the 900 bp SalI-BamHI terminator (0.1 picomoles) and 0.02 picomoles of BamHI-digested, phosphatased pBR322 in the presence of T4 DNA ligase.

The above reaction product was used to transform *E. coli* HB101. plasmids containing the cassette clones in pBR322 were isolated and the correct nucleotide sequence confirmed by DNA sequencing. This plasmid was then digested with BamHI and the BamHI cassette fragment containing the gB1 segment and GAPDH regulatory regions gel isolated and inserted into BamHI-digested, phosphatased pCl/1. Plasmid pCl/1 is a derivative of pJDB219 (Beggs, *Nature* (1978) 275:104) in which the region corresponding to bacterial plasmid pMB9 in pJDB219 is replaced by pBR322 in pCl/1. The pCl/1 plasmid containing the 1187 bp gB1 insert and GAPDH promoter and terminator regions was designated pHS127A. This plasmid was then used to transform the yeast strain *S. cerevisiae* AB103.1 (α, pep 4-3, leu 2-3, leu 2-112, ura 3-52, his 4-580). Transformants were initially grown in 1.0 ml of leu medium and then 50 ml of YEPD inoculated with 0.4 ml and grown further to an absorbance of 1-3 at 650 nm (12 hr). The yeast cells were pelleted by centrifugation at 2 krpm for 10 min at 4° C. and resuspended in 50 mM Tris-HCl, pH 8, 150 mM NaCl, 0.2% Triton X-100, 1 mM EDTA and freshly added 1.0 mM phenylmethylsulfonyl fluoride and 0.1 μg/ml pepstatin. The cells were repelleted and then resuspended in a volume equal to the packed cell volume in the same buffer. An equal volume of acid-washed glass beads (diameter 0.45-0.5 mm) was added and the yeast cells disrupted by vortexing at 4° C. for 10 min total, using 1 min intervals.

The tubes were centrifuged for 15 min at 14000× g at 4° C. and the supernatant isolated and analyzed on 10% SDS polyacrylamide gel and blotted onto nitrocellulose paper for Western analysis (Burnett, *Anal. Biochemistry*](1981) 112:195). A polyclonal antibody (DAKO) to HSV-1 was employed as the primary antibody. Expression of an HSV specific protein was observed at about 44 kd, the size expected for the gB fragment.

3. Glycoprotein B2

3.1 Isolation, cloning and characterization of the gB2 gene

The gene encoding HSV-2 gB had been shown to the colinear with the corresponding HSV-1 gB gene by analysis of HSV-1×HSV-2 intertypic recombinants and to lie approximately between prototypic map coordinates 0.30 and 0.42 (Ruyechan et al., *J. Virol.* (1979) 29:677-697). Thus, the HindIII H fragment of HSV-2 which spans map coordinates 0.28 to 0.40 (FIG. 7) includes the gB2 coding region. FIG. 7A shows a conventional prototype HSV-2 configuration in the first two lines. The restriction map for HindIII is shown in the third line. In addition to their colinear map location, serological and heteroduplex analyses indicate the close similarity of gB1 and gB2. Therefore, to locate the gB2 coding region more precisely, the fragments of the gB1 gene indicated in FIG. 7b, line I were used to probe Southern blots of restriction digests of the HSV-2 HindIII H fragment. The 0.55 kb PstI-SalI fragment that encodes amino acids 323-506 of gB1 hybridizes to a 2.6 kb XhoI fragment, a 2.0 kb SstI fragment, and additional specific restriction fragments. The adjacent 0.49 kb NcoI fragment of gB1 hybridizes to the flanking 3.2 kb XhoI band as well as a 4.2 kb SphI band. Two of these overlapping restriction fragments were subcloned into a pBR322 plasmid derivative to generate the plasmids pHS203 (containing the 5' end of the gene on a 2.6 kb XhoI fragment) and pHS207 (containing the 3' end of the gene on a 4.2 kb SphI fragment) with the map locations of the inserts shown in FIG. 7B, line III.

The exact location and the identity of the gB2 gene were verified by probing a Northern blot of poly A+ mRNA isolated from HSV-2-infected Vero cells with the restriction fragments of pHS203, shown in FIG. 7B line II. Both an 0.89 kb XhoI-SmaI and a 1.29 kb SmaI-NruI fragment hybridized to an abundant 3.0 kb message, an appropriate size and representational frequency for gB2 based on analogy to the analysis of gB1 transcripts. However, the same message did not hybridize to the rightmost 0.47 kb NruI-XhoI fragment. As expected a similar hybridization pattern was observed when poly A+ RNA prepared from HSV-1 infected Vero cells was probed with these same fragments, although the signal intensity was diminished due to the inefficiency of cross-hybridization. Since this analysis indicated both the limit of the right hand end of the gB2 gene as well as its size, it was apparent that the gB2 coding sequences must extend an additional 1 kb to the left of those sequences contained within the 1.98 kb NruI-SphI fragment of pHS203 into the overlapping pHS207 plasmid. Therefore, the gB2 gene was cloned as one continuous fragment of pHS203 to the 1.48 kb SohI-BamHI fragment of pHS207 and insertion into NruI and BamHI-digested pBR322 to generate pHS208.

The HSV-2 fragment encoding gB was sequenced on both strands in its entirety.

The nucleotide sequence for gB2 is shown in FIG. 4, line 2. The predicted amino acid sequence of gB2 is shown above the DNA sequence. For comparison, the DNA sequence and the amino acid sequence of gB1 from HSV-1 strain Patton is shown below. Spaces have been inserted into the sequence to permit maximal alignment of the two proteins. All numbers of FIG. 4 refer to the gB2 sequence. Characteristic TATA and CAT transcriptional regulatory sequences are most likely located 5' to the start of this sequence analysis analogous to the gB1 sequence. In the 3' noncoding region, a polyadenylation signal, AATAAAAA (proudfoot and Brownlee, *Nature* (1976) 263:211) at residues 2744 to 2751 is the probable termination site of the gB2 mRNA.

There is a potential transmembrane anchor region of 54 amino acids from $Ala_{745}$ to $Leu798$. Chou and Fasman analysis (*Adv. Protein Chem.* (1978) 47:45-148) indicates a mixed β-sheet and α-helix potential for the entire region. However, in order to avoid orientation of polar sidechains toward the lipophilic environment of the membrane bilayer, it is likely that this region adopts an α-helical conformation (Engelman and Steitz, *Cell* (1981) 23:411-422). An α-helix of this length (8.1 nm) would be more than sufficient to span a biological membrane 3 nm in thickness 2 times, placing the C-terminal domain of the protein on the exterior of the cell. Alternatively, the transmembrane domain may traverse the membrane 3 times and include the amphipatic domain beginning at $Asp_{723}$ that contains 4 additional charged residues. In this analysis, tight-packing of the 3 α-helices allows interchain hydrogen bonding between the charged residues, all of which are predicted to lie on the same face of the helix. Thus, the charged residues would be thermodynamically allowed with the membrane, as they would not interact with the hydrophobic lipid environment. This model would localize the C-terminus of the protein within the cytoplasm. While it is not presently possible to distinguish between the possibilities that the gB anchor spans the membrane two or three times, it is an important consideration in terms of positioning the C-terminus on the extracellular or cytoplasmic side of the membrane.

The C-terminal region of gB2 extends from the end of the membrane anchor region at $Leu_{798}$ to the end of the protein at $Leu_{904}$ and contains a high density of charged residues. No potential N-linked glycosylation sites are present in this portion of the type 2 protein.

The predicted gB2 protein is 904 amino acids in length and contains elements characteristic of a membrane glycoprotein. After cleavage of the predicted 22 amino acid signal sequence, the mature, non-glycosylated protein would have a molecular weight of 98,221. The amino terminal 22 residues contain a core of hydrophobic residues ($Leu_6$ to $Ala_{20}$) preceded by a charged basic residue (Arg at position 2) and an alanine-rich signal peptidase recognition sequence, $Ala_{20}$-$Ser_{21}$-$Ala_{22}$, conforming to rules identified for preferred signal peptidase cleavage sites and the general characteristics of eukaryotic signal peptides (Watson, *Nucl. Acid Res.* (1984) 12:5145-5164). Protein sequence analysis of the N-terminus of recombinant HSV-1 glycoprotein B identified the first amino acid of the mature type 1 protein as Ala followed by $Pro_{31}Ser_{32}Ser_{33}Pro_{34}$. Due to the conservation of the 6 amino acids centered around the signal cleavage recognition sequence, we assign $Ala_{23}$ of gB2 as the first amino acid of the mature glycoprotein.

The external hydrophilic region of the protein from $Ala_{23}$ to $Asp_{723}$ contains 8 possible sites for N-linked glycosylation identified by the sequence Asn-X-Thr/Ser where X=any of the 20 amino acids with the possible exception of aspartic acid. By analysis of the predicted secondary structure of gB1, pellett et al. found 6 of 9 possible glycosylation sites for gB1 on the surface of the protein at junctions of helical or β-sheet structures and therefore likely to be efficient substrates for glycosylation. The remarkable amino acid homology between the Type 1 and 2 proteins suggests that the utilization of potential glycosylation sites is similar.

A comparison of the primary sequences of HSV-1 and HSV-2 glycoprotein B is shown in FIG. 4. Amino acid differences between the Type 2 and Type 1 proteins are highlighted by boxes. Overall the two proteins share a nucleotide and an amino acid homology of 86%. However. the differences appear to be significant, since only 12.5% of the amino acid substitutions between gB1 and gB2 are conservative changes. These differences in primary sequence are clustered in certain regions of the protein resulting in long domains which are identical as well as small regions of marked divergence.

The region of greatest divergence between gB1 and gB2 is the signal sequence. For gB2, the predicted signal sequence is only 22 amino acids in length, as compared to 30 for gB1 strain Patton, and shares only 55% amino acid homology with the Type 1 protein. It is of interest to note that while the length of the entire coding sequence for gB1 and gB2 is the same (904 amino acids) the mature gB2 would be 7 amino acids longer than gB1 due to its shorter signal peptide.

3.2 Expression of gB2 in mammalian cells

Expression of HSV-2 glycoprotein gB has been achieved in COS cells (transient expression) and in CHO cells (stable cell line secreting gB2) transformed with pHS210 alone or cotransformed with pHS210 and a second plasmid containing dhfr.

Figure 8:
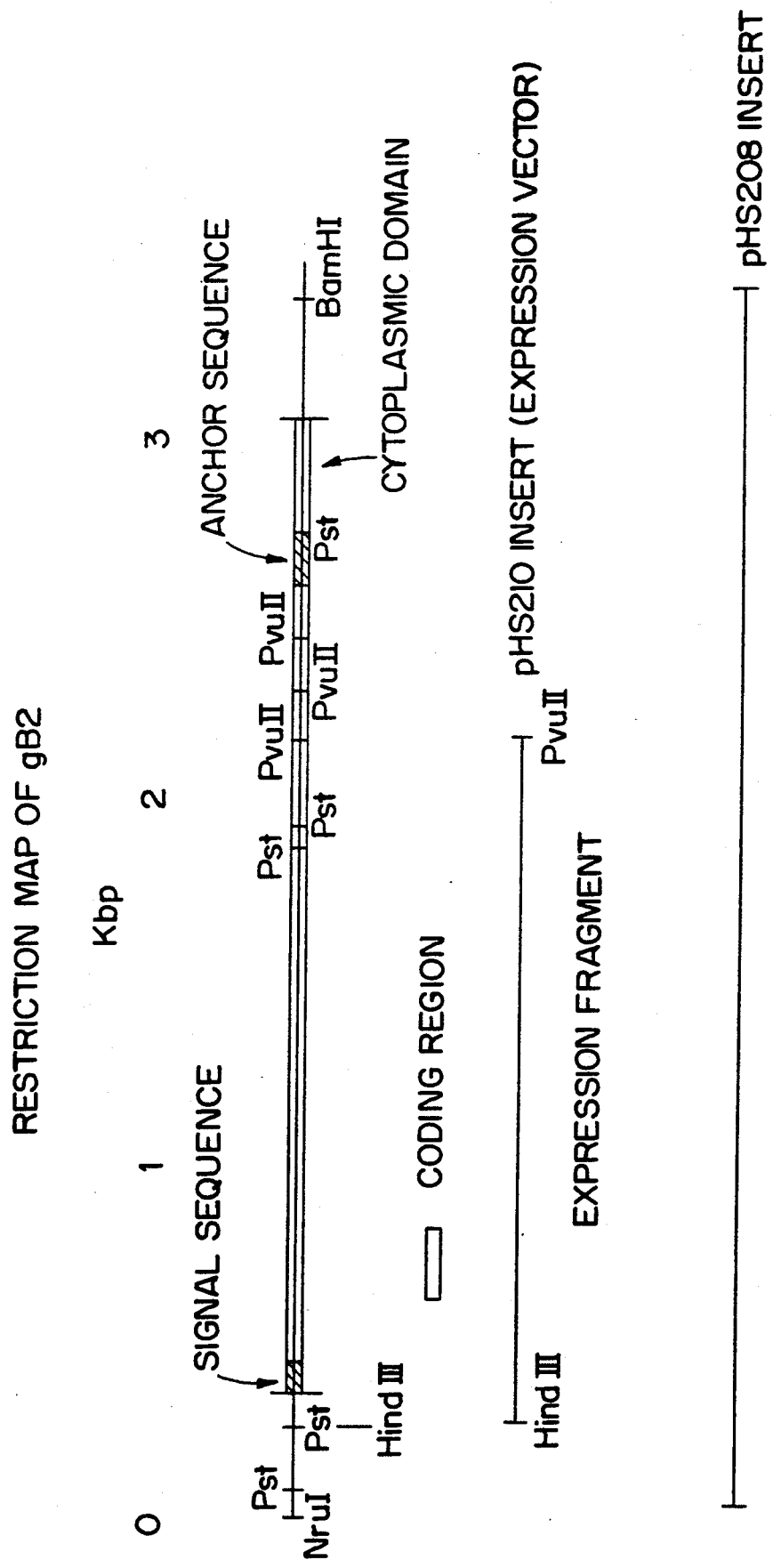
FIG. 8 is a restriction map of gB2.

Plasmid pHS210 was constructed as follows: The entire gene was subcloned as a 3.8 kb NruI-BamHI fragment in pBR322 to generate pHS208. See FIG. 8. The PstI site at the 5' end of the gene, 100 bp to the right (downstream) of the NruI site, was changed to a HindIII site by in vitro mutagenesis in M13. A HindIII to PvuII fragment of 1.9 kb was then inserted into pSV1, which was obtained by digestion of pSV1/dhfr with HindIII and BolII. See FIGS. 5 and 8. For this cloning step, pHS208 was cut with PvuII and the end repaired to blunt. The molecule was then cut with HindIII and the 1.9 kb HindIII-(PvuII) fragment isolated by gel electrophoresis. Likewise pSV1/dhfr was cut with BglII, repaired to blunt, cut with HindIII and the 4.85 kb HindIII-(BolII) vector fragment isolated by gel electrophoresis. These two fragments (1.9 kb and 4.85 kb) were ligated together to generate pHS210—the expression plasmid (FIG. 8).

Plasmid pHS210 was used directly to transform COS cells. Expression was detected by immunofluorescence using a gB specific monoclonal antibody, F3AB, and also using a commercially available polyclonal anti HSV-2 antibody (DAKO) as the primary antibody screen. Secretion of gB2 into the medium was detected by a gB2-specific ELISA. For this purpose, plates were coated with the monoclonal antibody. Samples of cell culture medium were added to coated plates, then bound gB2 was detected with the rabbit anti HSV-2 polyclonal antibody (DAKO) followed by horseradish conjugated goat antirabbit IgG.

For CHO cell transformation plasmid pHS210 was used along with a second plasmid containing dhfr as a selective marker (FIG. 8) in a cotransfection protocol. Following transfection and propagation in selective media, approximately 100 dhfr+ clones were isolated and screened for synthesis and secretion of gB2 using an ELISA assay in which ELISA plates were coated with F3AB specific monoclonal antibody. Clone pHS210 #3-1, which had the highest levels of gB secretion, was chosen for further characterization of the gB2 polypeptide. The gB2 protein was detected by labeling with [$^{35}$S]-methionine followed by radio immunoprecipitation. After a 1 hr pulse, diffuse doublet bands corresponding to polypeptides of 79 kd and 84 kd were detected intracellularly. These proteins are larger than the 68,991 dalton size predicted for the 637 residue truncated gene product, and they presumably correspond to partially glycosylated precursors. After a 5 hr chase, no gB2 was detected intracellularly, and an 89 kd polypeptide was detected in the medium. The size of the mature, fully glycosylated gB2 secreted into the media of clone pHS210 #3-1 is somewhat smaller than the 100 kd gB1 secreted by pHS114-6 due to the removal from pHS210 of the coding sequence for 94 amino acids included in the gB1 plasmid.

4. Glycoprotein D1

Figure 9:
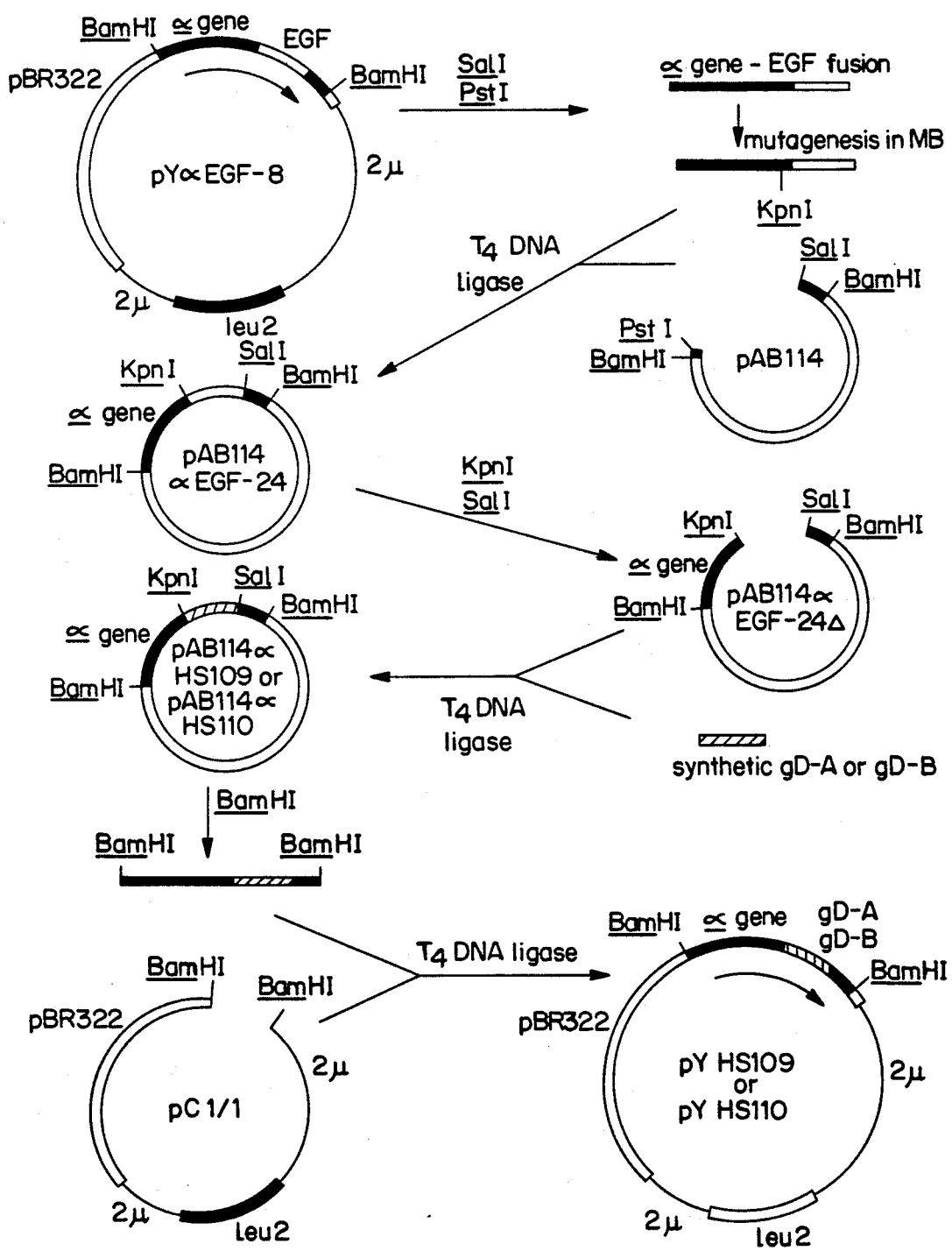
FIG. 9 is a flow chart showing construction of gD1 yeast expression vectors and construction of plasmids pYHS109 and pYHS110 which carry synthetic sequences for gD-A and gD-B.

4.1. Construction of yeast expression vectors containing synthetic DNA fragments coding for polypeptides A and B of the gD1 gene: pYHS109 and pYHS110 (FIG. 9).

Nucleotide sequences designated gD-A and gD-B based on portions of the amino acid sequence for glycoprotein D of HSV-1 reported by Watson et al. (1982) Science 218:381-384, and employing preferred yeast codons, were devised. The gD-A sequence, which encodes amino acids 253-283 (corresponding to amino acids 258-288, as incorrectly numbered by Watson et al., supra.) of the mature protein, was as follows:

```
                                    Processing Site
                                         ↓
Val Pro Leu Asp Lys Arg Leu Pro Pro Glu Leu Ser Glu Thr Pro Asn Ala Thr Gln
5'-CCTTGGATAAAAGATTGCCACCAGAATTGTCTGAAACCCCAAACGCTACCCAA
   CATGGGAACCTATTTTCTAACGGTGGTCTTAACAGACTTTGGGGTTTGCGATGGGTT
```

-continued

```
         Pro Glu Leu Ala Pro Glu Asp Pro Glu Asp Ser Ala Leu Leu Glu Asp Pro OP OC
         CCAGAATTGGCTCCAGAAGACCCAGAAGACTCTGCTTTGTTGGAAGACCCATGATAAG-3'
         GGTCTTAACCGAGGTCTTCTGGGTCTTCTGAGACGAAACAACCTTCTGGGTACTATTCAGCT
```

The gD-8 sequence, which encodes amino acids 8–23 (corresponding to amino acids 13–28, as incorrectly numbered by Watson et al., supra.) of the mature protein, was as follows:

```
                Processing Site
                      ↓
         Val Pro Leu Asp Lys Arg Ser Leu Lys Met Ala Asp Pro Asn Arg Phe Arg Gly Lys
         5'-CCTTGGATAAAAGATCTTTGAAGATGGCTGACCCAAACAGATTCAGAGGTAAG
            CATGGGAACCTATTTTCTAGAAACTTCTACCGACTGGGTTTGTCTAAGTCTCCATTC Asp Leu Pro OP OC
         GACTTGCCATGATAAG-3'
         CTGAACGGTACTATTCAGCT
```

The sequences each include a KonI cohesive end at the 5'-end and a SalI cohesive end at the 3'-end. Coding for the mature secreted peptide begins after the LysArg processing site. The 5'-end of each sequence is a modification of the 3'-end of the naturally occurring α-factor secretory leader and processing signal sequence, where the modification consists of a deletion of three glu-ala pairs and a replacement of a leucine by a proline to create a KpnI site in the nucleotide sequence. The 3'-end of each sequence includes two translational stop codons, OP and OC.

Synthetic DNA fragments having the sequences just described were prepared by synthesizing overlapping ssDNA segments as described by Urdea et al. (1984) Proc. Natl. Acad. Sci. USA 80:7461–7465 using the phosphoramidite method of Beaucage and Carruthers (1981) Tetrahedron Lett. 27:1859–1862, and annealing and ligating under the following conditions.

The ssDNA fragments were joined as follows: 50 to 100 pmoles of each segment (except the two segments at the 5'-terminii) were 5'-phosphorylated with 5.6 units of T4 polynucleotide kinase (New England Nuclear) in 10 mM dithiothreitol (DTT), 1 mM ATP, 10 mM $MgCl_2$ 100 ng/ml spermidine, 50 mM Tris-HCl, pH 7.8 (total volume: 20 µl) for 30 min at 37° C. Additional T4 kinase (5.6 units) was then added and the reaction continued for 30 min at 37° C. The fragments (except for the 5' terminii) were combined, diluted to 40 µl with water followed by addition of 60 µl of 1M sodium acetate, 12 µl of 250 mM EDTA, and 5 µg of 1 mg/ml poly-dA. After heating for 5 min at 65° C., the 5' terminal pieces were added, followed by 420 µl of ethanol (100%). The solution was chilled for 20 min at −80° C., centrifuged, and the pellet was washed twice with ethanol (100%) and dried. The pellet was redissolved in water (18 µl), heated to 100° C. for 2 minutes and then cooled slowly over 1.5 hours to 25° C. in a water bath.

The annealed fragment pool was ligated in a reaction mixture containing T4 DNA ligase (New England Biolabs, 1200 units) 1 mM ATP, 10 mM DTT, 10 mM $MgCl_2$, 100 ng/ml spermidine, and 50 mM Tris-HCl, pH 7.8 (30 µl). After 1 hour at 14° C., the reaction mixture was partially purified by preparative polyacrylamide gel (7%, native) electrophoresis. The DNA was removed from the appropriate gel slice by electroelution and ethanol coprecipitation with poly-dA (5 µg).

After assembly, the synthetic gD-A and gD-B fragments were substituted into a KpnI/SalI-digested bacterial cloning plasmid pAB114αEGF-24, which plasmid was prepared by cloning a mutagenized fragment of pYEGF-8 into pAB114 (see FIG. 1). The plasmids resulting from the insertion were designated pAB1-14αHS109 (gD-A) and pAB114αHS110 (gD-B).

The preparation of pAB114 was as follows: Plasmid pAB101 was obtained from the screening of a random yeast genomic library cloned in YEp24 (Fasiolo et al., 1981, J. Biol. Chem. 256:2324) using a synthetic 20-mer oligonucleotide probe (5'-TTAGTACATTGGTTGGCCGG-3')

homologous to the published α-factor coding region (Kurjan and Herskowitz. Abstracts 1981, Cold Springs Harbor meeting on the Molecular Biology of Yeasts, page 242). Plasmid pAB1 1 was obtained by deleting the HindIII to SalI region of pBR322. An EcoRI fragment of into the unique EcoRI site in pAB1 1 to produce pAB112. Plasmid pAB112 was digested to completion with HindIII, and then religated at low (4 µg/ml) DNA concentration to produce plasmid pAB113 in which three 63 bp HindIII fragments were deleted from the α-factor structural gene, leaving only a single copy of mature α-factor coding region. A BamHI site was added to plasmid pAB11 by cleavage with EcoRI, filling in of the overhanging ends by the Klenow fragment of DNA polymerase, ligation of BamHI linkers and religation to obtain a plasmid designated pAB12. Plasmid pAB113 was digested with EcoRI, the overhanging ends filled in, and ligated to BamHI linkers. After digestion with BamHI, the resulting 1500 bp which carries the single copy of the α-factor gene fragment was gel-purified and ligated to pAB12 which had been digested with BamHI and treated with alkaline phosphatase to produce pAB114, which contains a 1500 bp BamHI fragment carrying the α-factor gene.

The preparation of pYEGF-8 was as follows: A synthetic sequence for human epidermal growth factor (EGF) was prepared and ligated to pAB112 (described above) which had been previously completely digested with HindIII and SalI to produce pAB201. The HindIII site lies within the 3'-end of the α-factor gene, and the EGF sequence was inserted using appropriate linkers. The resulting plasmid was designated pAB201.

Plasmid pAB201 (5 µg) was digested to completion with EcoRI and the resulting fragments were filled in with DNA polymerase I Klenow fragment and ligated to an excess of BamHI linkers. The resulting 1.75 kbp fragment was isolated by preparative gel electrophoresis, and approximately 100 ng of this fragment was ligated to 10 ng of yeast plasmid pCl/1 (described below) which had been previously digested to completion with restriction enzyme BamHI and treated with alkaline phosphatase. The ligation mixture of the 1.75 kbp fragment carrying the partial α-factor gene fused to the EGF gene and pCl/1 was used to transform *E. coli* HB101 cells, and transformants were selected based on ampicillin resistance. DNA from one ampicillin resistant clone (designated pYEGF-8) was used to transform yeast AB103 (genotype: MATα. pep 4-3, leu 2-3, leu 2-112, ura 3-52, his 4-580, cir°) cells, and transformants selected based on their leu+ phenotype.

Plasmid pCl/1 is a derivative of pJDB219 (Beggs (1978) Nature 275:104) where the region derived from bacterial plasmid pMB9 has been replaced by pBR322. The pCl/1 plasmid carries genes for both ampicillin resistance and leucine prototrophy.

Plasmid pAB114αEGF-24 was generated by an in vitro mutagenesis procedure which deleted the sequences coding for the glu-ala processing region in the α-factor leader. Plasmid pAB114αEGF-24 was obtained as follows: a PstI-SalI fragment of pYEGF-8 containing the α-factor leader hEGF fusion was cloned in phage M13 and isolated in single-stranded form. A synthetic 36-mer oligonucleotide primer (5'-GGGGTACCTTTGGATAAAAGAAACTC-CGACTCCGAA-3')

was used as a primer for the synthesis of the second strand using the Klenow fragment of DNA polymerase I. After fill-in and ligation at 14° C. for 18 hours, the mixture was treated with $S_1$ nuclease and used to transfect *E. coli* JM101 cells. Phage containing DNA sequences in which the glu-ala region was removed were located using $^{32}$p-labeled primer as a probe. DNA from positive plaques was isolated, digested with PstI and SalI, and the resulting fragment inserted into pAB114 (described above) which has been previously digested to completion with SalI, partially with PstI and treated with alkaline phosphatase. The resulting plasmid was designated pAB114αEGF-24.

Referring again to FIG. 9, the BamHI-BamHI fragment of pAB114αHS109 or pAB114αHS110 (1588 base pairs for gD-A and 1546 base pairs for gD-B) was excised and ligated into the unique BamHI site of pCl/1. The resulting expression vectors were designated pYHS109 for gD-A and pYHS110 for gD-B.

4.2 Expression of gD-A and gD-B polypeptides in yeast

Plasmids pYHS109 and pYHS110 were both used to transform yeast strain AB103.1 (a, pep 4-3, leu 2-3, leu 2-112, ura 3-52, his 4-580, cir°) to leu prototrophy following the procedure of Hinnen et al., *Proc. Natl. Acad. Sci. USA* (1978) 75:1929-1933. The transformants were grown in 1 L cultures at 30° C. in buffered leucine-deficient media to saturation, corresponding to an absorbance of 5 at 650 nm. Yeast cell cultures were maintained at saturation for an additional 12 to 24 hrs with shaking at 30° C. The cultures were then harvested, the intact yeast cells pelleted by centrifugation at 3000 RPM, and the resulting supernatant media filtered through a 0.22 μ Millipore filter. This fraction was then passed through a C18 reverse phase column, constructed from 8 Seppak units purchased from Waters. The bound material was eluted with 30 ml of 80% (v/v) acetonitrile, 0.1% (v/v) trifluoroacetic acid in water, evaporated to dryness with a Buchii RotoVap and redissolved in 1.6 ml of distilled water. This material was separated on an HPLC C18 column monitored at 210 nm. The peak corresponding to each respective peptide was collected and its identity confirmed by antigenicity. Each peptide reacted specifically in an ELISA assay using rabbit polyclonal antisera which has been raised against a chemically synthesized gD-B peptide or partial gD-A peptide (residues 256 through 271 of the sequence shown for gD-A in page 9) purchased from Vega Biochemicals. Expression levels, as determined by spectrophotometric measurements of HPLC purified peptides, were on the order of 7.6 mg of gD-A per liter of yeast culture ($OD_{650}=5$) and 0.6 mg of gD-B per liter of yeast culture ($OD_{650}=5$). These results demonstrate the feasibility of expressing a relatively short portion or fragment of a protein and its secretion from yeast cells using an α-factor expression vector.

Figure 10:
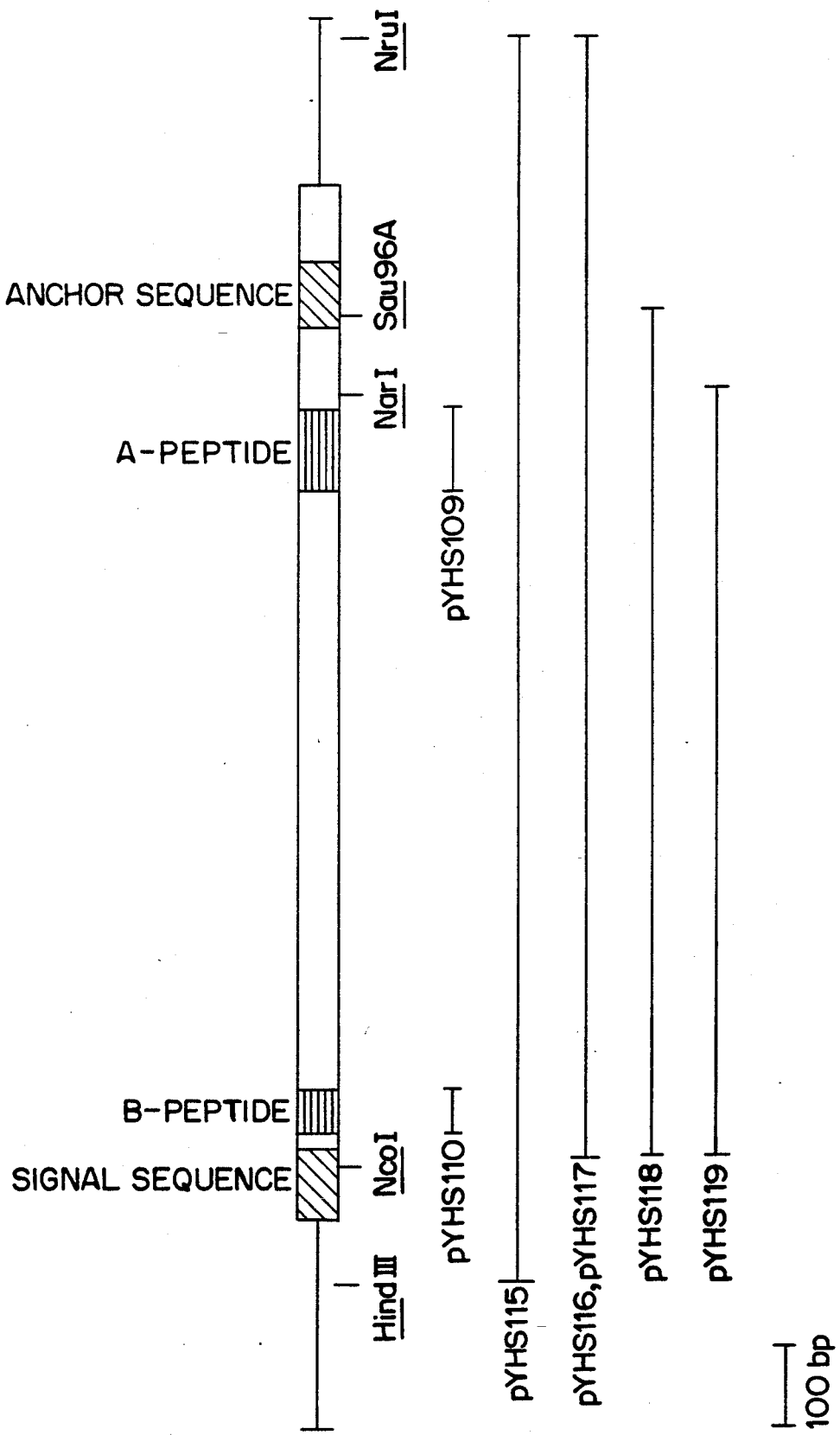
FIG. 10 is a partial restriction map of the gD region which notes the location of all the gD sequences inserted into yeast expression vectors.

4.3 Construction of yeast vectors for high level intracellular expression using fragments of the naturally occurring gD1 gene Nucleotide fragments from the naturally occurring gD gene expressing gD of HSV-1 (gD1) were also expressed intracellularly in yeast under control of the GAPDH promoter and terminator. A library of EcoRI fragments of HSV-1, strain Patton, cloned into the EcoRI site of pBR322, was made by Dr. Richard Hyman, Hershey Medical Center, Hershey, Pa. The gD is entirely contained within a 2.9 kb SacI fragment within the EcoRI fragment of one clone (clone H) isolated from the HSV-1 library. Clone H was obtained from Dr. Hyman; the 2.9 kb fragment was purified by gel electrophoresis and was used for the construction of several expression vectors which differ in the size of the gD fragment cloned and/or the synthetic linkers used in the 5' or 3' ends of the gD fragments. FIG. 10 illustrates the protein coding region (boxed region) and the fragments used for the construction of yeast expression vectors pYHS115, pYHS116, pYHS117, pYHS118 and pYHS119. A description of the construction of each plasmid follows.

4.3.1 Construction of pYHS115

Plasmid pYHS115 contains the gD gene in a GAPDH expression cassette cloned into the BamHI site of pCl/1 (described hereinabove).

The GAPDH expression cassette was constructed as follows: Three fragments were prepared as described in detail below):

(a) A BamHI-HindIII fragment (1407 bp) containing 346 bp of pBR322 and 1061 bp of the GAPDH promoter;
(b) A HindIII-SalI fragment (1430 bp) containing the gD gene, and
(c) A SalI-BamHI fragment (900 bp) containing the GAPDH terminator.

Figure 11:
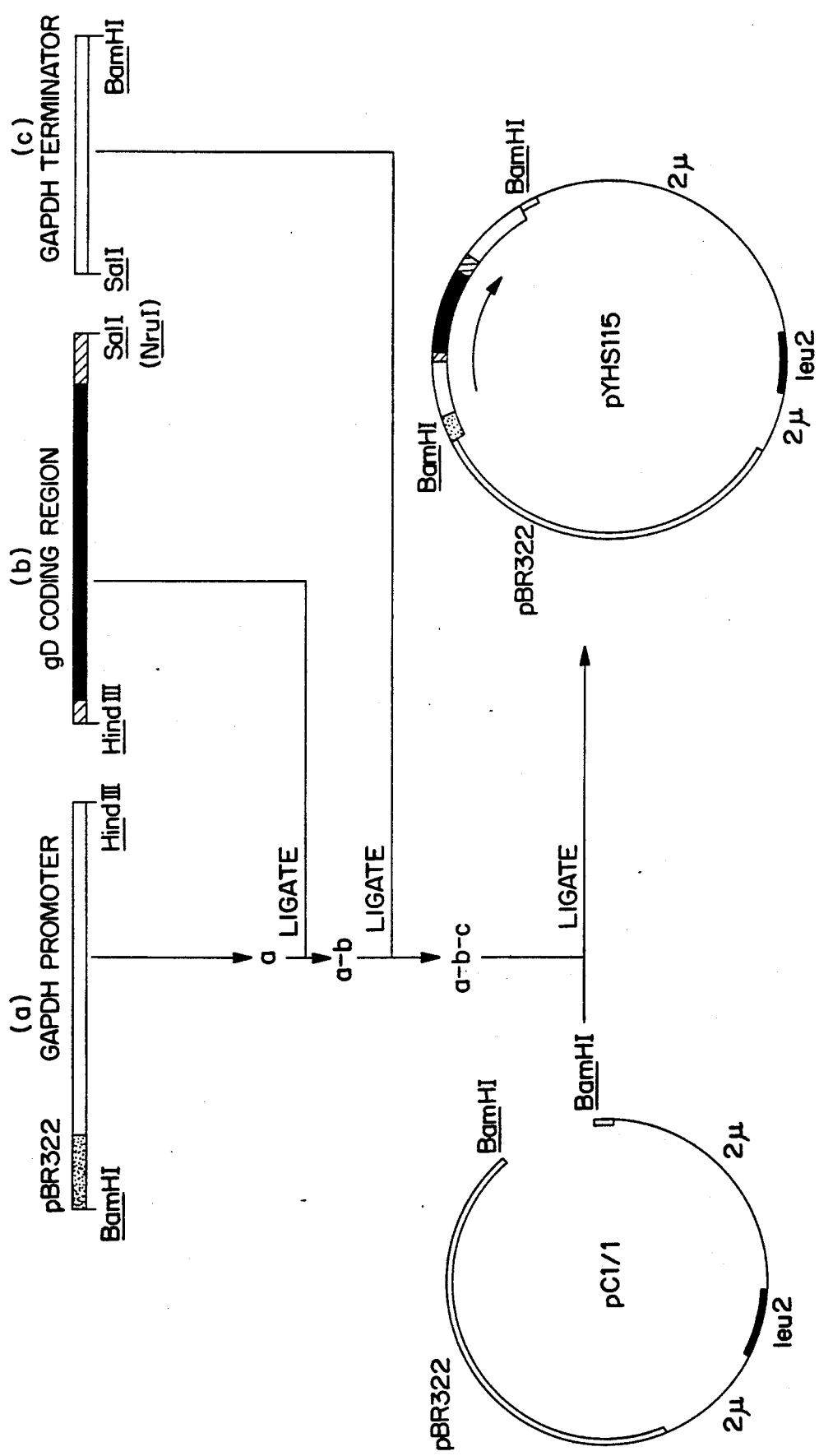
FIG. 11 is a flow chart of the construction of pYHS115 which carries a portion of the naturally occurring gene gD of HSV-1 strain Patton under the transcriptional control of the GAPDH promoter and terminator.

These fragments were ligated together and the mixture was digested with BamHI. The 3.7 kb resulting cassette was isolated by gel electrophoresis and ligated to BamHI cut, alkaline phosphatase-treated pCl/1 (FIG. 11).

Fragment (a) was prepared by completely digesting pGAP347 (described below) With BamHI followed by partial digestion with HindIII. The resulting 1407 bp fragment containing 346 bp of pBR322 and 1061 bp of the GAPDH promoter was isolated by gel electrophoresis.

Construction of pGAP347 was as follows. PolyA+ RNA was isolated from *S. cerevisiae* yeast strain A364A. Double-stranded cDNA was synthesized using AMV reverse transcriptase and E coli DNA polymerase I. Poly-dC-tails were added to the double-stranded cDNA molecule using deoxynucleotide terminal transferase. Poly-dC-tailed cDNA was annealed to poly-dG-tailed pBR322 and used to transform E. coli HB101. 1000 transformants were screened by colony hybridization to labeled PolyA+ RNA, and a subset further examined by restriction endonuclease mapping, and DNA sequencing. Three clones containing GAPDH sequences were isolated from the the pool. One clone (pcGAP-9) contained an insert of about 1200 base pairs and was used for further work.

A yeast gene library was prepared by inserting fragments obtained after partial digestions of total yeast DNA with restriction endonuclease Sau3A in lambda-phage Charon 28, according to Blattner et al., Science (1977) 196:161-169. Several fragments containing yeast GAPDH coding sequences were isolated by screening the phage library with labeled DNA from pcGAP-9. The yeast GAPDH gene of one of these clones was subcloned in pBR322 as a 2.1 kb HindIII fragment (pGAP-1). The GAPDH promoter region was isolated from these clones. A HhaI-HindIII fragment of about 350 bp containing the 3' portion of the promoter was obtained by: a) digestion of pGAP-1 with HinfI to generate an approximately 500 bp segment which includes the 3' part of the promoter and a region encoding the N-terminal amino acids of GAPDH; b) resection with Bal31 to yield a 400 bp fragment lacking the GAPDH coding region (3'-terminus one base upstream from the ATG initiator codon); c) addition of HindIII linkers; and d) cleavage with HhaI. A second HindIII-HhaI fragment of about 700 bp containing the 5' portion of the promoter was isolated from pGAP-1, ligated to the 350 bp HhaI-HindIII fragment and treated with HindIII. The resulting 1061 bp HindIII fragment was isolated by gel electrophoresis and cloned in HindIII digested, alkaline phosphatase-treated pBR322 to produce pGAP347.

Fragment (b) was obtained as follows: Clone H, isolated from the HSV-1 Patton library, was digested with SacI. A 2.9 kb SacI fragment was purified by gel electrophoresis and subsequently digested with HindIII and NruI. The 1430 bp HindIII-NruI fragment containing the gD gene (FIG. 3) was purified by gel electrophoresis, ligated to NruI-SalI adaptors of the following sequence:

```
5'-TGATAAG-3'
   ACTATTCAGCT
``` and digested with SalI.

Fragment (c) was obtained as follows: A 900 bp fragment containing the GAPDH terminator was obtained by BamHI and SalI digestion of pUH28 (described under "Construction of pYHS117") and purification by gel electrophoresis.

4.3.2 Construction of pYHS116 pYHS116 contains a gD gene fragment which has a 600 bp deletion at the 5' end of the coding region that comprises most of the signal sequence coding region. To construct pYHS116, two fragments were obtained:
(a) A BamHI-HindIII fragment (1407bp) containing 346 bp of pBR322 and 1061 bp of the GAPDH promoter. This fragment was obtained as described under "Construction of pYHS115."

(b) A NcoI-BamHI fragment (2150 bp) containing the partial gD gene followed by the GAPDH terminator. This fragment was obtained by BamHI/NcoI digestion of pYHS115 (described previously) and purification by gel electrophoresis. A HindIII-NcoI chemically synthesized adaptor of the following sequence:

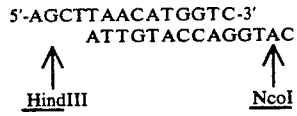

was ligated to the fragment. This adaptor provides for the first two codons (met and val) fused in the correct reading frame to the partial gD.

Fragments (a) and (b) were ligated together and subsequently digested with BamHI. The resulting 3.5 kb cassette was isolated by gel electrophoresis and ligated to BamHI cut, alkaline phosphatase-treated pCl/1.

4.3.3 Construction of pYHS117.

Plasmid pYHS117 contains the same partial gD gene clone in pYHS116, fused in reading frame to 7 extra codons at the 5'-end, which code for the first 7 amino acids of the GAPDH structural gene. To construct pYHS117 two fragments were obtained.
(a) An NcoI-SalI digested vector (6.8 kb) comprising pBR322 sequences, the GAPDH promoter fused to the first 7 codons of the structural gene and the GAPDH terminator. This vector was prepared by NcoI digestion of pUH28 (described below), followed by a partial digestion with SalI and purification by gel electrophoresis.
(b) An NcoI-SalI fragment (1430 bp) containing a partial gD gene. This fragment was obtained by NcoI-SalI digestion of pYHS115 (described previously) and purification by gel electrophoresis.

These two fragments were ligated together to yield a pBR322 derived vector which contains a partial gD gene fused in reading frame to the 7 first codons of GAPDH gene, flanked by the GAPDH promoter in its 5' end and by the GAPDH terminator in its 3' end. The gD expression cassette was obtained by digesting this plasmid with BamHI and purifying a 3.4 kb fragment by gel electrophoresis. This fragment was ligated to BamHI digested, alkaline phosphatase-treated pCl/1 to produce pYHS117.

Plasmid pUH28 contains the coding and 3' noncoding regions of the hepatitis B surface antigen (HBsAg) gene fused in incorrect reading frame to the first 7 codons of the GAPDH structural gene. This fusion is flanked in its 5' end by the GAPDH promoter and in its 3' end by part of the GAPDH coding region followed by the GAPDH terminator. This plasmid was constructed so as to have an NcoI site at the 3' end of the first 7 codons of the GAPDH gene with the following sequence:

```
                met
5'-AAACAAAATGGTTAGAGTTGCTAATTCC-3'
   TTTGTTTTACCAATCTCAACGATTAAGGGTTAC
3'GAPDH        5'GAPDH            NcoI site
promoter       coding region
```

When this NcoI end is ligated to the partial gD fragment (b, described above) the correct reading frame for the gD protein is regenerated. The SalI site used in the preparation of fragment a (described above) is at the 5' region of the GAPDH terminator. Therefore, a deletion of the sAg coding plus noncoding regions and GAPDH coding region was obtained by digesting pUH28 with NcoI and partially with SalI.

The construction of pUH28 involves cloning of fragment that contains the HBsAg coding and 607 bp of 3' noncoding regions prepared from pHBS5-3 Hae2-1 (described below) into the GAPDH containing vector pGAP$_2$ (described below). To prepare the fragment, pHBS5-3 Hae2-1 was linearized by PstI digestion, partially digested with NcoI and a Pst-NcoI fragment of 1.9 kb containing pBR322 sequences. HBsAg coding and 3' sequences was purified by gel electrophoresis. This fragment was subsequently digested with EcoRI and a 1.2 kb NcoI-EcoRI fragment containing the HBsAg coding and 3' noncoding regions was purified by gel electrophoresis. Plasmid pGAP$_2$ was linearized with XbaI and treated with Bal31 to remove approximately 100 bp. The plasmid was subsequently digested with NcoI and a vector fragment of about 9 kb was purified by gel electrophoresis. The NcoI ends of the vector and the 1.2 kb NcoI-EcoRI fragment encoding HBsAg were ligated. The recessed end was filled in with Klenow and the resulting blunt end was ligated to the blunt produce pUH28.

pHBS5-3 Hae2-1 is a plasmid that contains the HBsAg coding regions and 607 bp of 3' flanking sequences. This plasmid is a derivative of pHBS5-3 which contains the same insert but only 128 bp of 3' untranslated region instead of 607 bp. Plasmid pHBS5-3 has been previously described in copending U.S. application Ser. No. 609,540, filed May 11, 1984 (pp. 13-14), which disclosure is incorporated herein by reference. pHBS5-3 Hae2-1 was constructed as follows. The HBV genome (3.2 kb) was excised from pHB-3200 (Valenzuela et al., *Nature* (1979) 280:815-819) by restriction digestion with EcoRI. The 3.2 kb fragment was purified by gel electrophoresis and was recircularized by ligation of the EcoRI sticky ends. This closed HBV genome was digested with HaeII, which cuts in the 3' noncoding regions. Recessed ends were filled in with Klenow and HindIII linkers were ligated. The DNA was cut with HindIII and subsequently with XbaI, which has a single site in the HBS coding region. A 1.2 kb XbaI-HindIII fragment containing 586 base pairs of the coding sequence of HBV and 607 base pairs of the 3' noncoding region was isolated by gel electrophoresis. This fragment was cloned into pHBS5-3 previously cut with XbaI and HindIII and treated with alkaline phosphatase, to yield pHBS5-3 Hae2-1.

pGAP-2 is a pBR322 derived vector which contains a BamHI insert that has the GAPDH coding sequence. 5' and 3' flanking regions. There are two XbaI sites in this plasmid: one in the coding region and one in the 3' flanking sequences. pGAP-2' is a derivative of pGAP-2 in which the XbaI site present in the 3' flanking regions has been eliminated. For this purpose, 50 μg of pGAP-2 were partially digested with XbaI, treated with Bal31 to remove 25 base pairs per end, and ligated. The plasmids were used to transform *E. coli* HB101 and the transformants were selected for loss of XbaI site in the 3' flanking region.

4.3.4. Construction of pYHS118

This vector contains a partial gD gene with deletions in two regions: a 600 bp deletion in the 5'-end coding regions which comprises most of the signal sequence coding region and a 1300 bp deletion in the 3'-end coding region which includes most of the anchor sequence coding region. It also contains 7 extra codons from the GAPDH gene coding regions fused in the reading frame at the 5' end of the gD gene, similar to pYHS117. Plasmid pYHS118 was constructed as follows: pYHS115 was digested with NcoI and SalI, the resulting 1430 bp fragment containing the partial gD was purified by gel electrophoresis and submitted to digestion with NarI (FIG. 10). The two resulting fragments (fragment a: 873 bp containing 5' end and fragment b: 411 bp containing 3' end) were independently isolated by gel electrophoresis. Fragment b was subsequently digested with Sau96A to yield three fragments which were separated by gel electrophoresis. The 87 bp NarSau96A fragment was recovered from the gel and was ligated to Sau96A-SalI synthetic adaptors of the following sequence:

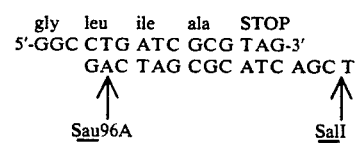

```
      gly  leu  ile  ala  STOP
5'-GGC CTG ATC GCG TAG-3'
   GAC TAG CGC ATC AGC T
    ↑                ↑
  Sau96A            SalI
```

The NarI-(Sau96A)SalI fragment (102 bp) was digested with SalI, purified by gel electrophoresis and ligated with fragment a (previously described). The resulting NcoI-SalI fragment (975 bp) was ligated to NcoI-SalI, digested and gel purified pUH28 as described under "Construction of pYHS117." The resulting pBR322 derived vector was digested with BamHI and a 3.1 kb fragment containing the gD expression cassette was purified by gel electrophoresis. This cassette was ligated to BamHI digested, alkaline phosphatase treated PCl/1 to produce pYHS118.

4.3.5 Construction of pYHS119.

This vector contains a partial gD gene with deletions in two regions: a 600 bp deletion in the 5' end coding regions which comprises most of the signal sequence coding regions and a 2400 bp deletion in the 3' end coding regions which includes all the anchor sequence coding regions and about 700 bp upstream of the anchor sequence. It also contains 7 extra codons from the GAPDH gene coding region fused in reading frame at the 5' end of the gD gene, as pYHS117 and pYHS118. Plasmid pYHS119 was constructed as follows: pYHS115 was digested with NcoI and SalI, the resulting 1430 bp fragment containing the partial gD was purified by gel electrophoresis and subsequently digested with NarI. The 873 bp NcoI-NarI fragment was isolated by gel electrophoresis. A synthetic adaptor of the following sequence:

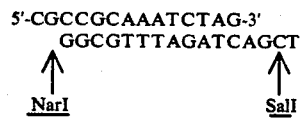

```
  5'-CGCCGCAAATCTAG-3'
      GGCGTTTAGATCAGCT
       ↑            ↑
      NarI         SalI
``` which provides complementary nucleotides to the NarI 5' overhang, 3 codons in reading frame, a stop codon and a 5' overhang of SalI, was ligated to the 873 bp NcoI-NarI fragment then digested with SalI. The resulting NcoI-SalI fragment was ligated to pUH28 which had been previously completely digested with NcoI and partially digested with SalI and purified by gel electrophoresis as described under "Construction of pYHS117." The resulting pBR322 derived vector was digested with BamHI and a 2.2 kb fragment containing the gD expression cassette was purified by gel electrophoresis. This cassette was ligated to BamHI digested, alkaline phosphatase-treated pCl/1 to produce pYHS119.

4.4 Synthesis of gD1 from yeast vectors containing partial or complete gD1 gene Plasmids pYHS115, 116, 117, 118 and 119 were used to transform yeast strain AB103.1 (a, pep 4-3, leu 2-3, leu 2-113, ura 3-52, his 4-580, cir°) following the procedure of Hinnen et al., supra. The transformations were grown to an $OD_{650}=3$ at 30° C. in YEPD media. The cultures were then harvested by pelleting the yeast cells at 3000 RPM. Cells were spheroplasted with zymolyase and subsequently osmotically lysed in a hypotonic solution. Membranes were spun down in an Eppendorf centrifuge, and the pellet was solubilized in 0.1% SDS with protease inhibitors for 16 hours at 4° C. The suspension was centrifuged and total protein, as well as gD specific protein, was determined in both soluble and insoluble fractions. Expression of the gD gene in each of the above described constructions was detected by Western Blot hybridization (Towbin et al., *Proc. Natl. Acad. Sci. USA* (1979) 76:4350). For this purpose protein samples were submitted to SDS-polyacrylamide gel electrophoresis (Laemmli, *Nature* (1970 227:680) and electroblotted onto nitrocellulose filters (Towbin et al., supra.). The filter was preincubated with goat serum and subsequently treated with a rabbit polyclonal antibody raised against HSV-1 (Dako). The filter was then incubated with a second goat anti-rabbit antibody conjugated with horseradish peroxidase (Boehringer-Mannheim) and finally it was incubated with horseradish peroxide color development reagent (Bio-Rad) and washed. The results indicate that immunoreactive material is being synthesized in yeast AB103.1 strain transformed with gD expression vectors, with the exception of transformants containing pYHS115. In all other cases, gD protein corresponds to 0.1 to 0.5% of total yeast cell protein.

Figure 12A:
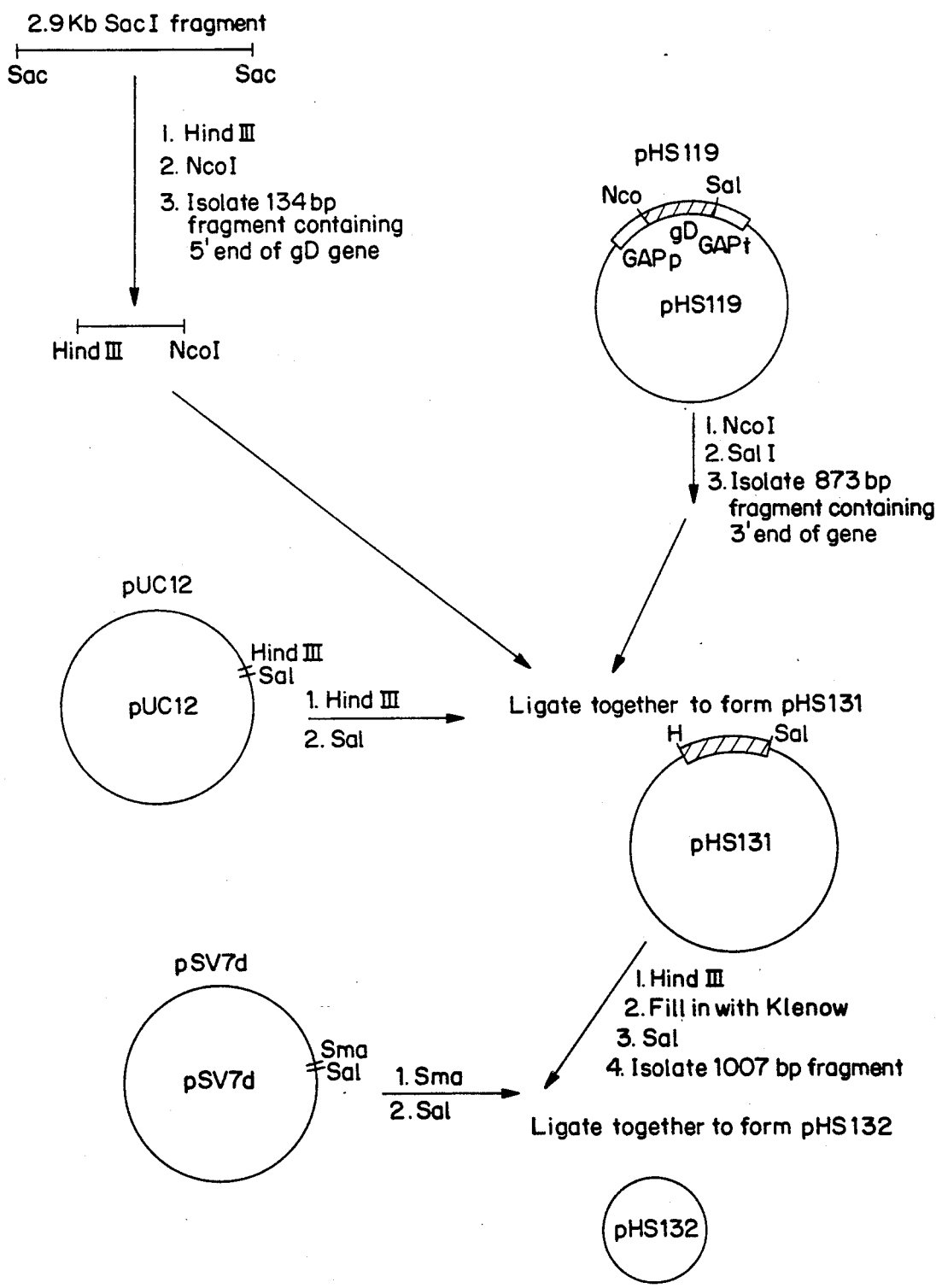
FIG. 12 is a flow chart for the construction of pHS132, a mammalian expression vector for gD1.
Figure 12B:
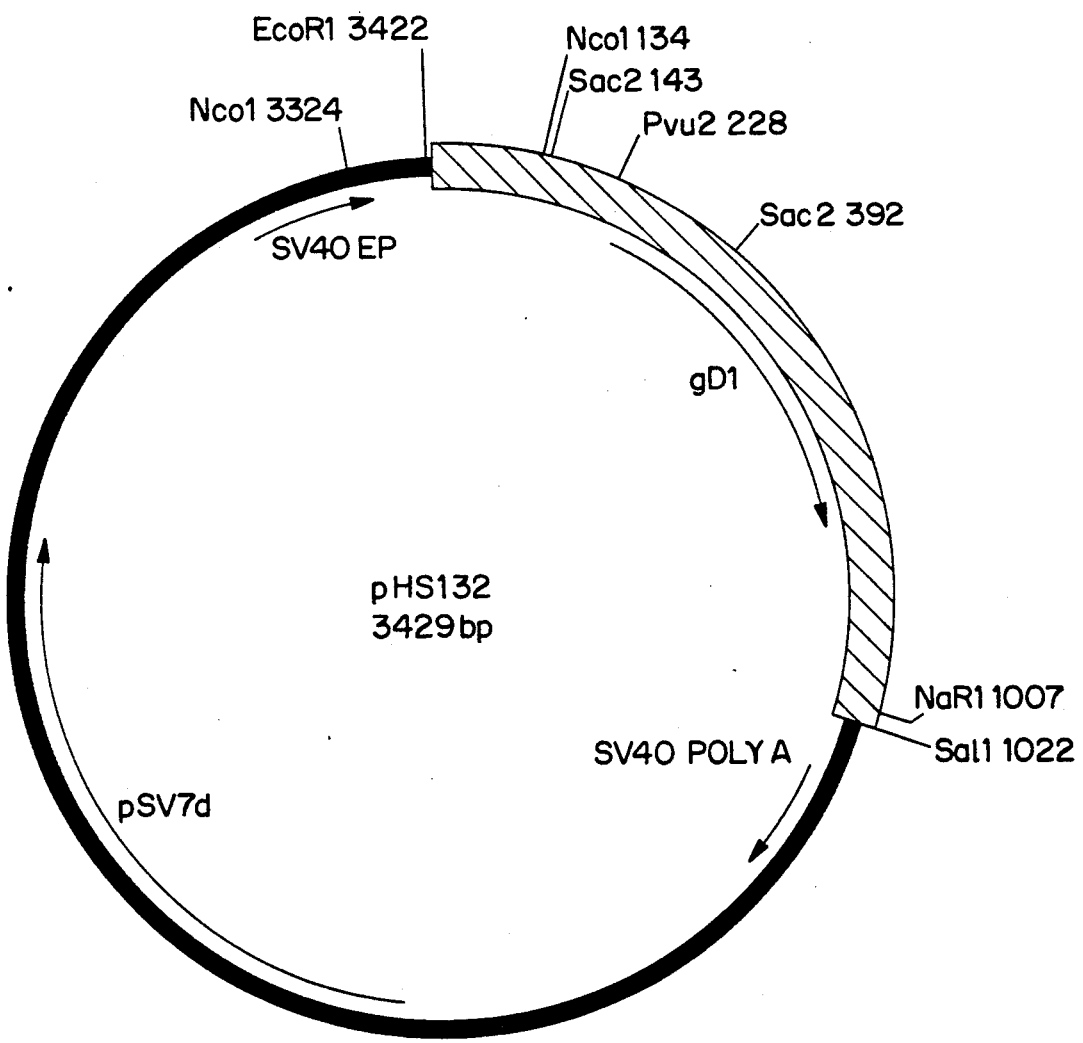

4.5 Construction of mammalian expression vectors for gD1: pHS132 (FIG. 12).

A library of EcoRI fragments of HSV-1, strain Patton, cloned into the EcoRI site of pBR322 was made by Dr. Richard Hyman, Hershey Medical Center, Hershey, Pa. The gD1 gene is entirely contained within a 2.9 kb SacI fragment within the EcoRI fragment of clone H from this library. Clone H, containing a 15 kb EcoRI insert, was obtained from Dr. Hyman. The 2.9 kb fragment was purified by gel electrophoresis and then digested to completion with HindIII and NcoI. The 5' end of the gD gene, consisting of 74 bp of 5' untranslated sequences plus 60 bp coding for the amino terminal 20 amino acids. was gel isolated as a 134 bp fragment. The 3' end of the gD gene was obtained by digestion of pHYS119 (see Section 4.3.5) with NcoI and SalI and isolation of the 873 bp fragment. These two fragments (5' and 3' ends) were ligated together with the plasmid pUC12 which had previously been digested with HindIII and SalI. The pUC12 vector is commercially available from Pharmacia and P-L Biochemicals, the resulting plasmid was designated pHS131. The plasmid pHS131 was digested with HindIII, the 5'-4 base pair overhang was filled in with Klenow polymerase and then digested with SalI. The 1007 bp fragment containing the gD gene was gel isolated and ligated into the plasmid pSV7d which had previously been cut with SmaI plus SalI. The plasmid pSV7d is described below. The resulting expression vector is designated pHS132. Its derivation is outlined in FIG. 12.

The plasmid encodes 315 amino acids of gD1 protein including a 25 amino acid signal sequence out of a total of 399 amino acids for the complete protein. The protein has been truncated at the carboxyl terminus and lacks 84 amino acids including the hydrophobic membrane anchor domain and the cytoplasmic domain such that the resulting protein is secreted into the medium.

The plasmid pSV7d was constructed as follows: the 400 bp BamHI/HindIII fragment containing the SV40 origin of replication and early promoter was excised from SVgtI (Mulligan, R., et al., *J. Mol. Cell Biol.* (1981) 1:854-864) and purified. The 240 bp SV40 BclI/BamHI fragment containing the SV40 poly A addition site was excised from pSV2/dhfr (Subramani et al., *J. Mol. Cell Biol.* (1981) 1:854-864) and purified. The fragments were fused through the following linker:

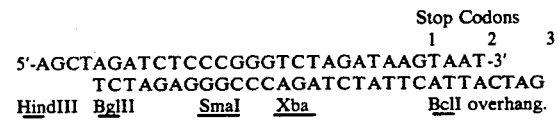

This linker contains five restriction sites, as well as stop codons in all three reading frames. The resulting 670 bp fragment (containing the SV40 origin of replication, the SV40 early promoter, the polylinker with stop codons and the SV40 polyadenylation site) was cloned into the BamHI site of PML, a pBR322 derivative with about a 1.5 kb deletion (Lusky and Botchan, *Cell* (1984) 36:391). to yield PSV6. The EcoRI and EcoRV sites in the PML sequences of PSV6 were eliminated by digestion with EcoRI and EcoRV, treated with Bal31 nuclease to remove about 200 bp on each end, and finally religated to yield PSV7a. The Bal31 resection also eliminated one BamHI restriction site flanking the SV40 region, approximately 200 bp away from the EcoRV site. To eliminate the second BamHI site flanking the SV40 region, pSV7a was digested with NruI, which cuts in the pML sequence upstream from the origin of replication. This was recircularized by blunt end ligation to yield pSV7 b.

pSV7c and pSV7d represent successive polylinker replacements. Firstly, pSV7 b was digested with StuI and XbaI. Then, the following linker was ligated into the vector to yield pSV7c:

Thereafter, pSV7c was digested with BglII and XbaI, and then ligated with the following linker to yield pSV7d:

```
  BglII   EcoRI      SmaI   XbaI    BamHI    SalI
5'—GATCTCGAATTCCCCGGGTCTAGAGGATCCGTCGAC
      AGCTTAAGGGGCCCAGATCTCCTAGGCACGTGATC
```

4.6 Expression of gD1 in mammalian cells

Expression of gD1 from plasmid pHS132 has been demonstrated in many experiments. First, specific immunofluorescence was observed in COS 7 cells following transfection using the methods described previously and using a commercially available rabbit sera against HSV-1 (DAKO) for detection. Second, stable CHO cell lines secreting gD1 were established. The expression levels were analyzed by ELISA and verified by radioimmunoprecipitation of pulse labeled and chased cell lysates and media. Third, gD1 was purified from the media of roller bottle cultures of the CHO cell line D64 by sequential steps of ammonium sulfate precipitation, immunoaffinity chromatography and ultrafiltration. For the affinity chromatography the gD monoclonal antibody 8D2 described in Rector et al. (1982) supra, linked to cyanogen bromide activated Sepharose 4B was employed.

5. Glycoprotein D2

5.1 Construction of mammalian expression vectors for gD2

The HindIII L fragment of HSV-2 strain 333 was cloned in pBR322 by Dr. Richard Hyman as noted in the reference Kudler et al., Virology (1983) 124:86-99. The gene for the glycoprotein gD2 had been mapped to the short unique region of the virus between 0.90-0.945 map units by Ruyechan et al., *J. Virol.* (1970) 29:677-697, a region covered by the HindIII L fragment as shown in the genomic map of Roizman, B., *Ann. Rev. Genet* (1979). 13:25-57. The DNA sequence of the gD2 gene has been published by Watson, Gene (1983) 26:307-312.

Figure 13B:
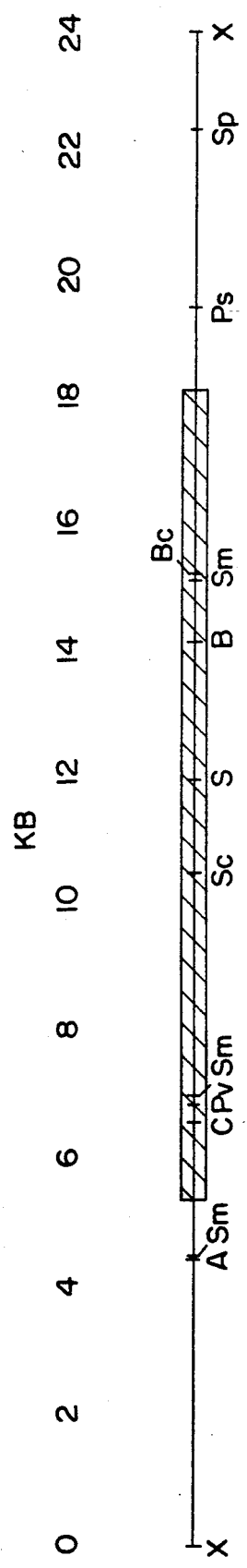
FIG. 13A and FIG. 13B are a physical map of HSV-2 indicating the coding region for gD2.
Figure 13A:
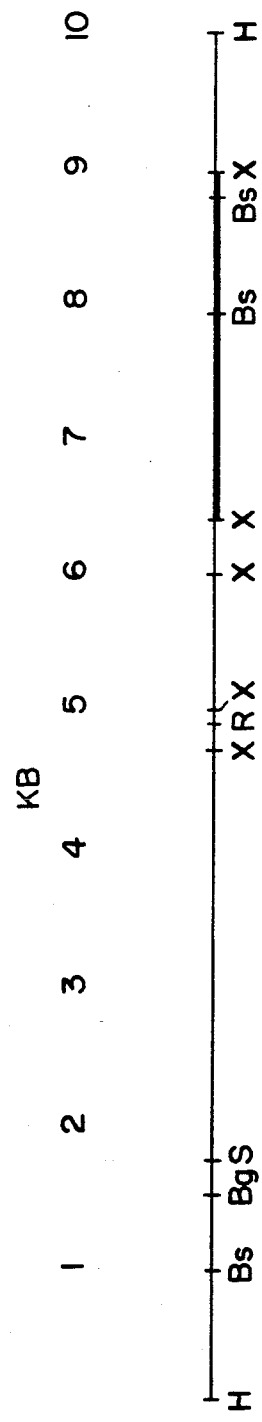
Figure 14:
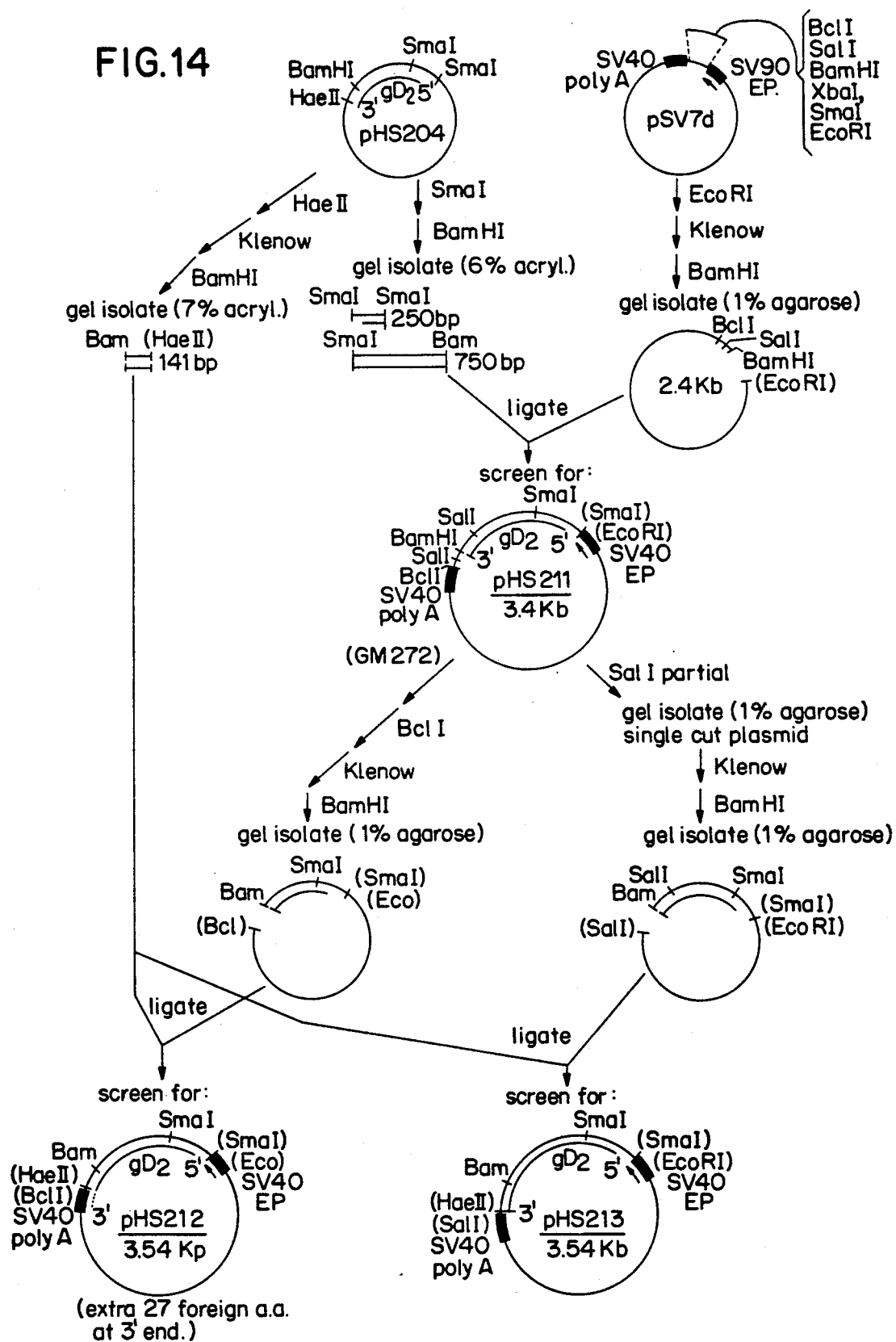
FIG. 14 is a flow chart of the construction of mammalian vectors for gD2.

The HindIII L fragment cloned in pBR322 was obtained from Dr. Richard Hyman and the restriction map shown in FIG. 13A determined. The gene for gD2 was found to lie on a 2.4 kb XhoI fragment by probing Southern blots of restriction digests of the HindIII L fragment with the 2.9 kb SacI fragment encoding gD1. A map of the XhoI fragment and the position of the gD2 gene is shown in FIG. 13B. The 2.4 kb XhoI fragment was cloned in a pBR322 derivative vector containing an XhoI site to generate plasmid pHS204. Three different gD2 expression vectors, plasmids pHS211, pHS212, and pHS213 were constructed as follows and as diagrammed in FIG. 14. The plasmid pHS211 encodes the first 305 amino acids of gD2 including the signal sequence. For its construction pHS204 was cut with SmaI and BamHI and two restriction fragments were gel isolated: a 250 bp SmaI fragment containing the 5' end of the gene including 82 bp of 5' untranslated sequence and the 3' adjacent 746 bp SmaI-BamHI fragment containing an interior portion of the gene. The mammalian cell expression vector pSV7d (described in Section 4.5) was cut with EcoRI, the 5' 4 bp overhang repaired to blunt with Klenow polymerase and then cut with BamHI. The two fragments from pHS204 were ligated into the digested pSV7d and bacterial transformants were screened for the appropriate orientation of the SmaI fragment to generate the vector pHS211.

The plasmid pHS212 which encodes 352 amino acids of gD2 or 47 additional residues beyond those present in pHS211 was constructed by the digestion of pHS204 with HaeII and repairing the ends to blunt with Klenow polymerase followed by digesting with BamHI. A 141 bp (HaeII) (the parenthesis intends the terminus has been filled in) to BamHI fragment was gel isolated. The plasmid pHS211 was transferred into the *E. coli* strain GM272 (dam⁻) and plasmid DNA prepared, which was then restricted with BclI followed by blunt end repair with Klenow polymerase then digestion with BamHI. The large vector fragment (about 3.4 Kb) was gel isolated and ligated together with the 141 bp (HaeII)-BamHI fragment to generate the plasmid pHS212. The fusion of gD2 sequences to plasmid vector sequences at the 3' end of the gene results in the addition of 27 codons of nonsense DNA to the 3' end of the gD2 gene. To eliminate these nonsense sequences the plasmid pHS213 was constructed by partial digestion of pHS211 with SalI and gel isolation of the single cut plasmid which was then repaired to blunt with Klenow polymerase and digested with BamHI. The (HaeII) to BamHI fragment of 141 bp from pHS204 was ligated into the linearized, pHS211 to generate the plasmid pHS213.

5.2 Expression of gD2 in mammalian cells

The expression of gD2 in mammalian cells was first assayed by transfection of COS 7 cells with pHS211, pHS212 and pHS213 for transient expression. Expression of gD2 was detected both by immunofluorescence and by capture ELISA analysis of COS 7 conditioned media using a rabbit anti-HSV-2 antibody for the immunofluorescence and a gD type common antibody, 8D2 (Rector et al., (1982) supra.), for the capture antibody in the ELISA.

Permanent CHO cell lines were then established by transfection with the plasmids pHS211 or pHS213 with Ad dhfr and selection for dhfr acquisition and screening by ELISA for gD2 expression.

Description of Ad-dhfr

The plasmid bearing the dhfr gene was constructed by fusing the major late promoter from adenovirus-2 (Ad-MLP, map units 16-17.3) to the mouse dhfr cDNA at the 5' end. DNA coding for the intron for SV40 small t Antigen and the SV40 early region polyadenylation site was obtained from pSV2-neo, described in Southern and Berg, *J. Mol. Appl. Genet.* (1982) 1:327-341, and fused to the 3' end of the dhfr cDNA. These three segments were subcloned into pBR322 to obtain the plasmid Ad-dhfr. This plasmid is functionally similar to the dhfr plasmid described in Kaufman and Sharp, *Molec. and Cell Biol.*, (1982) 2:1304-1319.

6. Vaccine Studies

6.1 Protection of guinea pigs against initial and recurrent genital herpes: immunization prior to infection with HSV-2

The recombinant gB1 protein was produced as described in Section 2.2 above. The gB protein was purified by sequential steps of lentil lectin chromatography, immunoaffinity chromatography, and concentration by ultrafiltration resulting in a preparation which was 70% homogeneous as determined by SDS polyacrylamide gel electrophoresis.

The conclusion are essentially the same as noted for primary disease.

TABLE 1

Effect of HSV glycoprotein vaccines on primary HSV-2 genital infection in guinea pigs.

| Group | Treatment[a] | Dose μg | Adjuvant[b] | Route[c] | Animals with Skin Lesions | Severity of Skin Disease[d] | Duration of Urinary Retention[e] | % Mortality[f] |
|---|---|---|---|---|---|---|---|---|
| 1 | None | — | — | — | 19/19 | 14.8 ± 1.0 | 5.4 ± 0.4 | 32 |
| 2 | CHO Extract | 8 | Alum | SQ | 11/11 | 11.9 ± 1.4 | 5.3 ± 0.3 | 27 |
| 3 | gP2 | 50 | CFA | FP | 0/6 | 0 | 0 | 0 |
| 4 | gP2 | 50 | Alum | FP | 4/9 | 0.7 ± 0.5 | 0.6 ± 0.6 | 0 |
| 5 | gP2 | 50 | Alum | SQ | 5/8 | 2.3 ± 0.9 | 3.0 ± 1.0 | 22 |
| 6 | gB | 40 | Alum | SQ | 7/8 | 2.8 ± 1.1 | 3.9 ± 0.7 | 0 |
| 7 | gD | 40 | Alum | SQ | 7/8 | 2.1 ± 1.0 | 2.5 ± 0.8 | 0 |
| 8 | gB + gD | 40 + 40 | Alum | SQ | 8/8 | 1.7 ± 0.7 | 1.5 ± 0.6 | 0 |

[a]Vaccines administered 9.6 and 3 was prior to intravaginal HSV-2 inoculation with 5.3 log$_{10}$ pfs HSV-2 (MS Strain) except group 3 which was immunized 9 and 4 weeks prior to viral challenge.
[b]Alum = Aluminum phosphate (10%); CFA = complete freund's adjuvant.
[c]SQ = Subcutaneously in hindlimb; FP hindlimb footpad.
[d]Mean area under the skin lesion score-day curve ± error.
[e]Mean days ± standard error.
[f]Deaths within 14 days of HSV-2 inoculation.

The recombinant gD1 protein was prepared as described in Sections 4.5 and 4.6.

Total HSV-2 glycoproteins were prepared HSV-2 strain 333 infected Vero cells by lentil lectin Sepharose chromatoqraphy using the method of Respess et al. J. Virol. Methods (1984) 8:27. These mixtures contained approximately 15% gB and 4.5% gD, as well as high concentrations of gC, lower amounts of gE and gG plus a mixture of unidentified HSV and Vero cell proteins.

This study was designed to test the effect of a variation in route of immunization, adjuvant (complete Freund's adjuvant versus alum) and the efficacy of recombinant mammalian gD plus recombinant mammalian gB. Eighty-one female Hartley guinea pigs were immunized as noted in the following table.

| Group | Treatment | Dose | Adjuvant | Route | N |
|---|---|---|---|---|---|
| 2 | CHO cell extract | 8 μg | Alum | SQ* | 12 |
| 3 | HSV-2 total glycoprotein (pG2) | 50 μg | Freund's | Foot-pad | 9 |
| 4 | pG2 | 50 μg | Alum | Foot-pad | 9 |
| 5 | pG2 | 50 μg | Alum | SQ | 8 |
| 6 | HSV-1 gB | 40 μg | Alum | SQ | 8 |
| 7 | HSV-1 gD | 40 μg | Alum | SQ | 9 |
| 8 | HSV-1 gB + gD | 40 μg + 40 μg | Alum | SQ | 8 |
| 1 | Untreated | — | — | — | 18 |

*Subcutaneously

Group 2 was immunized twice on days −63 and −28. All other groups were immunized thrice on days −58, −42 and −21. On day 1 all pigs were intravaginally inoculated with 5×10$^5$ Pfu HSV-2 strain MS. Groups 6–8 are recombinant mammalian produced glycoproteins. The course of the initial genital HSV-2 infection was evaluated as before with the results shown in Table 1 below. The experiment shows that the choice of both route and adjuvant modifies the outcome of the primary disease; alum is a less effective adjuvant than complete Freund's adjuvant for these antigens and the subcutaneous route is less effective than the footpad. More importantly for the present application, the mixture of recombinant gB1 plus gD1 affords better protection than the mixture of glycoproteins from HSV-2 infected Vero cells (compare groups 5 and 8). The pattern of recurrent disease for these same animals is shown in Table 2 and

TABLE 2

Effect of HSV glycoprotein vaccination on the pattern of recurrent genital HSV-2 infection in guinea pigs[a]

| Group | Treatment | N | Days Lesions Observed[b] (Mean ± SE) | Recurrent Episodes[c] (Mean ± SE) | Days/Episodes |
|---|---|---|---|---|---|
| 1 & 2 | Control | 9 | 20.6 ± 2.4 | 10.9 ± 1.2 | 1.9 |
| 3 | gP2/CFA/Footpad | 6 | 3.2 ± 1.3 | 2.3 ± 1.0 | 1.4 |
| 4 | gP2/Alum/Footpad | 8 | 3.0 ± 0.8 | 2.4 ± 0.6 | 1.3 |
| 5 | gP2/Alum/SQ | 5 | 11.8 ± 2.0 | 7.0 ± 0.9 | 1.7 |
| 6 | gB/Alum/SQ | 6 | 13.8 ± 2.4 | 7.5 ± 1.4 | 1.8 |
| 7 | gD/Alum/SQ | 9 | 11.2 ± 2.1 | 7.4 ± 1.2 | 1.5 |
| 8 | gB + gD/Alum/SQ | 8 | 9.9 ± 1.8 | 5.9 ± 0.9 | 1.7 |

[a]Animals examined for recurrent lesions day 14–92 after intravaginal HSV-2 challenge.
[b]All groups except gP2/Alum/SQ significantly different from control (p < 0.05).
[c]All groups except gD significantly different from control (p < 0.05).

6.2. Therapeutic Studies: Effect of Recombinant HSV glycoprotein vaccines administered after primary infection on subsequent recurrent herpetic diseases in guinea pigs Female Hartley guinea pigs were intravaginally inoculated with 5×10$^5$ pfu HSV-2 MS strain on day 1. Animals were treated with acyclovir (5 mg/ml) from days 1–10 by addition to the drinking water. Acyclovir reduces the severity of primary infection and thus the mortality, incidence of secondary bacterial infection and incidence of genital scarring. The use of acyclovir during primary infection has been shown to have no impact on the course of the disease after the cessation of treatment for the guinea pig (Bernstein et al., Virology, (1986) 67:1601). After recovery from primary infection, the animals were immunized with HSV-2 total glycoprotein preparation (gP2). with a mixture of recombinant gB1 and gD1 (HSV-1 gB+gD) or received no treatment. Treatment groups are shown below:

| Group | Treatment | Dose | Adjuvant | Route | N |
|---|---|---|---|---|---|
| I | None | None | None | None | 11 |
| II | HSV-1 gB + gD | 25 μg + 25 μg | Freund's | Footpad | 11 |
| III | gP2 | 50 μg | Freund's | Footpad | 11 |
| IV | Control, | None | Freund's | Footpad | 9 |

-continued

| Group | Treatment | Dose | Adjuvant | Route | N |
|---|---|---|---|---|---|
| | Adjuvant only | | | | |

Animals were immunized on day 21 and again on day 42 by injection of the vaccines into the hind footpads. Both recombinant proteins gB1 and gD1 were produced in mammalian cells as previously described. Results are reported in Table 3 and FIG. 15.

The results show that the pattern of recurrent herpetic disease was the same for Groups I and IV, hence these groups were pooled for analysis (control, n=20).

TABLE 3

| Group | N | Days Lesions Observed (Mean ± SE) | Recurrent Episodes (Mean ± SE) | Percent Severe Recurrences[c] | Days/ Episodes |
|---|---|---|---|---|---|
| Control | 20 | 15.9 ± 1.5 | 9.0 ± 0.7 | 19.4 ± 2.9 | 1.77 |
| gB + gD | 11 | 9.0 ± 1.6[b] | 6.6 ± 1.0[a] | 7.1 ± 2.2[b] | 1.36 |
| gP2 | 11 | 11.0 ± k0.9[b] | 7.3 ± 0.7[a] | 12.1 ± 3.1[b] | 1.51 |

[a]Glycoproteins (50 μg) administered with complete Freund's adjuvant in the hind footpad 21 and again 42 days after intravaginal HSV-2 challenge; recurrences scored day 21 through 92.
[b]Significantly different from control (p < 0.05).
[d]Percent recurrences with two or more herpetic lesions.

Figure 15:
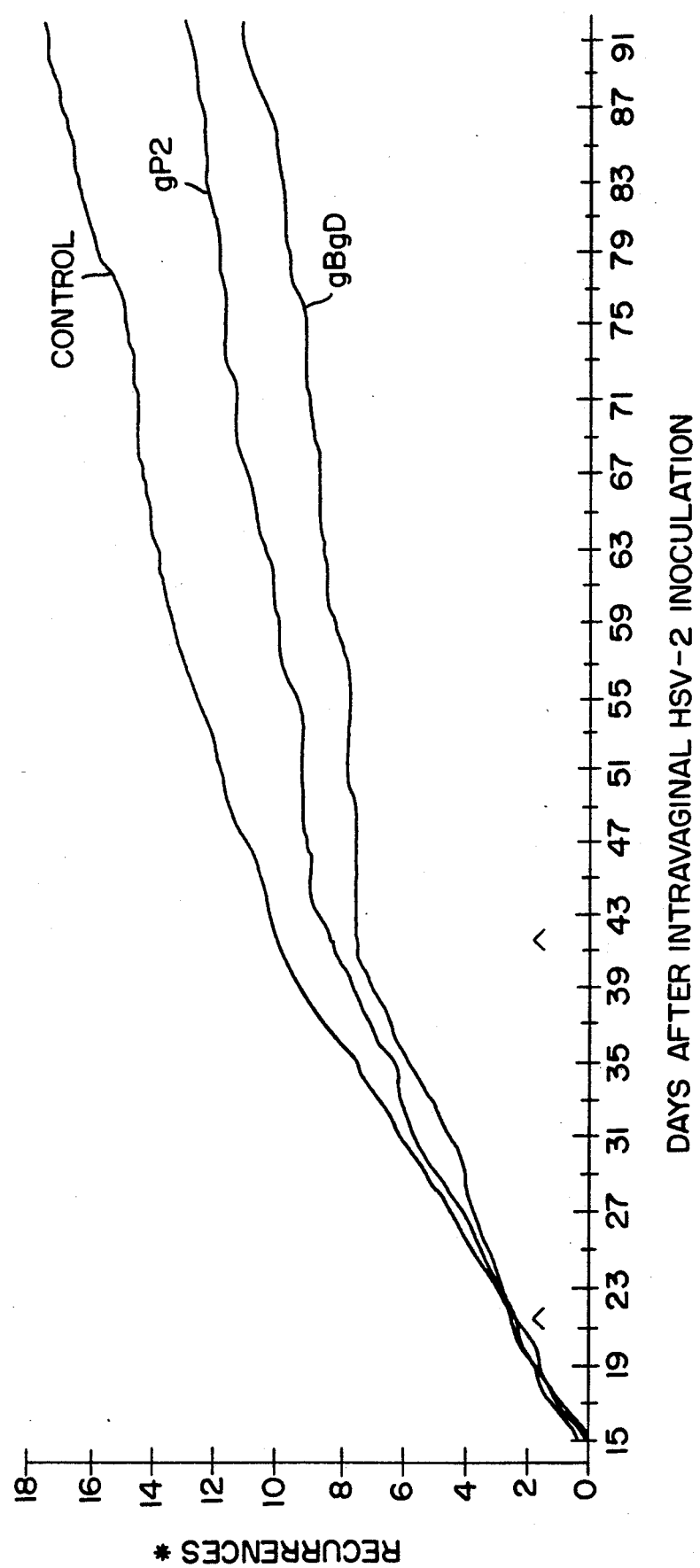
FIG. 15 shows the effect of vaccination with recombinant gB-gD after primary infection on recurrent herpetic disease.

Results shown in Table 3 and FIG. 15 indicate that vaccination with the recombinant glycoproteins has a significant impact on the frequence of recurrent disease. In addition, the gB+gD combination is better than the mixture of natural glycoproteins.

The rate of recurrent disease as measured by the number of lesion days occurring within a specified time is an assessment that considers both the frequency and the duration of recurrent episodes. FIG. 17A shows the rate of recurrent herpetic infections, expressed as the mean number of days per week that herpetic lesions were noted. The immunized group includes both gBgD and gP-2 vaccinated animals. As shown in FIG. 17A, the rate of recurrent disease (lesion days per week) declined in all groups as the period of evaluation became more remote to the initial infection, but the rate of decline was greater in the vaccinated animals. The difference in the rates of recurrent herpetic infections between control animals and immunized animals is shown in FIG. 17B. As seen in FIG. 17B, the effect of glycoprotein immunization on the rate of recurrent disease appeared to have been established following the first immunization dose rather than after the second dose, as might have been deduced from FIG. 15.

6.3. Therapeutic Studies: Effect of recombinant HSV glycoprotein vaccines administered after primary infection on the host immune response The effect of post-infection glycoprotein administration on the host immune response was determined by measuring anti-HSV antibodies produced by the infected animals prior to infection, and after immunization with HSV glycoprotein vaccines.

The animals were inoculated with HSV-2 ms strain, treated with acyclovir, and treated with HSV glycoprotein vaccines as described in Section 6.2. Sera from the animals was collected on days 41 and 95. Anti-HSV antibodies in the sera was measured by ELISA, essentially as described in Pachl, C., et al, J of Virology (1987) 61:315-325, which is the procedure described in Section 1.6. The capture antigens included HSV-1 glycoprotein mixture (gP-1), HSV-1 glycoprotein D (gD-1) or HSV-2 glycoprotein D (gD-2).

The effects of HSV glycoprotein vaccine administration on anti-HSV antibody titers is shown in Table 4, where the data is expressed as the geometric mean. Antibody was not detected in sera collected prior to HSV inoculation. As seen in Table 4, in the untreated control animals anti-HSV antibody titers were greater on day 41 than on day 95. In contrast, glycoprotein treated animals generally exhibited rising titers through day 95, and vaccination with HSV glycopoteins resulted in significant increases in anti-HSV antibody titers (p<0.05) compared to the untreated controls. Moreover, whereas treatment with the gP-2 mixture produced a 1.4 to 7 fold increase in antibody titers, treatment with recombinant HSV-1 gBgD vaccine resulted in a 9 to 31 fold elevation in titers compared to control values. Thus, the administration of HSV glycoproteins to animals, and particularly recombinant HSV glycoproteins gBgD, augments the host immune response and, as shown above in Section 6.2, reduces the frequency and severity of recurrent HSV disease.

TABLE 4

Effects of HSV Glycoprotein Vaccine Administration after Recovery from Initial Genital Herpes on Anti-HSV Antibody Titers in Guinea Pigs

| Treatment | Anti-HSV Antibody | | | | | |
|---|---|---|---|---|---|---|
| | gP-1 Antibody | | gD-1 Antibody | | gD-2 Antibody | |
| | Day 41 | Day 95 | Day 41 | Day 95 | Day 41 | Day 95 |
| Untreated | 548 | 474 | 32.5 | 14 | 65 | 48 |
| Adjuvant only | 818 | 754 | 22 | 34 | 25 | 68 |
| gP-2 | 2796 | 3343 | 177 | 152 | 91 | 297 |
| gBgD | 9891 | 14881 | 2444 | 4864 | 606 | 2391 |

6.4. Therapeutic Studies: Effect of adjuvants on the immune response induced by HSV glycoprotein vaccines containing gD1

Several adjuvants were examined to determine their effect on the efficacy of immunotherapeutic treatment with HSV glycoprotein vaccines. The adjuvants tested were complete Freund's adjuvant (CFA), alum, N-acetyl-muramyl-L-threonyl-D-isoglutamine (thr-MDP). N-acetyl-nor-muramyl-L-alanyl-D-isoglutamine referred to as nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine referred to as MTP-PE). In addition, an adjuvant (RIBl) containing three components extracted from bacteria, monophosphoryl lipid A, trehalose dimycolate and cell wall skeleton (MPL+TDM+CWS) in a 2% squalene/Tween 80 emulsion was also tested.

The adjuvant effects were determined by measuring the amount of anti-gD1 antibodies resulting from administration of gD1 containing vaccines which were also comprised of the various adjuvants. The vaccines containing gD1 alone serve as a model for gBgD containing vaccines, since the adjuvant effect is not expected to be specific to the type of HSV glycoprotein in the vaccines.

In the following studies gD1 was synthesized in pHS132 and isolated as described in Section 4.6. Female guinea pigs were given three footpad immunizations consisting of 35 μg gD1 and various adjuvant formulations at three week intervals. One week after the second immunization, and one, five, nine and thirteen weeks after the third immunization the animals were bled and anti-gD titers were determined by ELISA. as described in Section 1.6.

The results presented below are indicative that the most promising of the adjuvants tested are MTP-PE and RIBI formulations, since they consistently produce high anti-gD1 titers in experimental animals. These levels were equivalent to those seen with CFA, although the titers were not maintained for as long a period of time as with CFA.

6.4.1. Comparison between CFA, alum, and thr-MDP

The animals were immunized with vaccines containing gD1 and either CFA, alum, thr-MDP, or thr-MDP plus alum. The effect of the adjuvants on anti-gD titers is shown in Table 5, where the data is expressed as the geometric mean. As seen in Table 5, the most effective adjuvant was CFA. The highest antibody titers of the longest duration were seen in the group immunized with the CFA vaccine. The effect of the other adjuvants is expressed as the percent of the titer obtained with CFA. The mean titers of those animals immunized with the thr-MDP adjuvant ranged from approximately 50 to 70% of the titers obtained with CFA. The lowest anti-gD1 titers were obtained using as adjuvant a 10% alum suspension, and the combination of the thr-MDP plus alum was less efficacious than thr-MDP alone.

medium (sterile, isotonic Dulbecco buffer PH 7.2, without $Ca^{++}$ and $Mg^{++}$ salts). As seen in Table 6, immunization with vaccine containing CFA still yielded the highest anti-gD1 mean titer. The titers obtained with nor-MDP ranged from 44 to 74% of the mean titers obtained with the group immunized with CFA. The mean titers obtained with MTP-PE and exogenous gD1 were somewhat lower than that obtained with nor-MDP, with a range from 32 to 72% of those obtained with CFA. The very low titers obtained with MTP-PE and liposome encapsulated gD1 may be due to the very low levels of gD1 in the encapsulated form. The dose of encapsulated gD1 was only about 7% of the exogenous dose. This low dosage was due to the very low efficiency of incorporation of gD1 into liposomes, which may have been caused by the size of the antigen. Alternative formulations of liposomes could lead to more efficient incorporation of the antigen.

TABLE 6

HSV Adjuvant Study Mean ELISA Titers

| Experiment B Adjuvant | Number | Bleed 1 | % of CFA | Bleed 2 | % of CFA | Bleed 3 | % of CFA |
|---|---|---|---|---|---|---|---|
| CFA/IFA | 7(6) | 8009 ± 1130 | 100 | 13962 ± 2304 | 100 | 8298 ± 896 | 100 |
| nor-MDP squalene/arlacel | 7(6) | 3519 ± 905 | 44 | 10387 ± 2946 | 74 | 5759 ± 920 | 69 |
| MTP-PE-Liposome | 7(6) | 4051 ± 891 | 51 | 9989 ± 1161 | 72 | 2653 ± 457 | 43 |
| MTP-PE-gD-Liposome | 7(6) | 415 ± 218 | 5 | 1656 ± 175 | 12 | n.d. | n.d. |

6.4.3. Comparison of CFA and RIBI

The animals were immunized with gD1 vaccines containing either CFA or RIBI. As seen in Table 7, the anti-gD1 mean titers of animals immunized with RIBI containing vaccine ranged from 60 to 104% of the titers of animals immunized with CFA containing vaccines. The highest anti-gD1 titers obtained with RIBI were at bleed 2, where the titers surpassed those obtained with CFA.

TABLE 7

HSV Adjuvant Study Mean ELISA Titers

| Experiment C Adjuvant | Number | Bleed 1 | % of CFA | Bleed 2 | % of CFA | Bleed 3 | % of CFA |
|---|---|---|---|---|---|---|---|
| CFA/IFA | 5(4) | 7127 ± 5405 | 100 | 8315 ± 2604 | 100 | 6175 ± 1007 | 100 |
| RIBI | 7(6) | 5550 ± 2365 | 78 | 8638 ± 2566 | 104 | 3748 ± 1897 | 61 |

TABLE 5

HSV Adjuvant Study Mean ELISA Titers

| Experiment A Adjuvant | Number | Bleed 1 | % of CFA | Bleed 2 | % of CFA | Bleed 3 | % of CFA |
|---|---|---|---|---|---|---|---|
| CFA/IFA | 6(5) | 13709 ± 2161 | 100 | 15066 ± 2878 | 100 | 16835 ± 5527 | 100 |
| Alum | 4 | 1199 ± 467 | 9 | 1353 ± 318 | 9 | 1118 ± 211 | 7 |
| thr-MDP | 6 | 9334 ± 2505 | 68 | 9641 ± 1696 | 64 | 7271 ± 1524 | 43 |
| thr-MDP + ALUM | 6 | 2280 ± 501 | 17 | 5527 ± 1399 | 37 | 8333 ± 1707 | 50 |

6.4.2. Comparison of CFA, nor-MDP, and MTP-PE

The animals were immunized with vaccines containing gD1 and either CFA, nor-MDP, and MTP-PE. The MTP-PE was encapsulated in liposomes, and this latter adjuvant was administered both with exogenous gD1, and with gD1 incorporated into the liposomes. Liposomes were prepared by vortexing synthetic phosphatidylcholine, phosphatidylserine and MTP-PE (or MTP-PE & gD1) at a ratio of 175:75:1 in suspension

6.4.4. Comparison of RIBI, nor-MDP in low oil formulation, two component RIBI, and two component RIBI plus nor-MDP The high oil formulation of nor-MDP could be problematic due to side effects associated with immunization, such as redness and irritation at the site of injections. These side effects could be overcome with lower oil formulation, and in addition, are more easily prepared and injected.

Low oil formulations of nor-MDP contained 4% Squalene and 0.0008% Tween 80 as compared to the usual formulation of nor-MDP, which was 40% Squalene and 10% Aracel A.

Moreover, the cell wall skeleton component (CWS) in RIBI is a complex of undefined character; therefore, it was desirable to substitute nor-MDP for this component in RIBI (nor-RIBI) and to evaluate nor-RIBI with RIBI, and with two component RIBI which lacked CWS (RIBI-2).

The effect of these adjuvants on the anti-gD1 titer is shown in Table 8. As seen in the Table, CWS is an important component of RIBI, since omitting it caused significant decreases in the anti-gD1 titer at all time points, and almost a 98% decrease in the titer at the early time point. However, the CWS component was effecitvely replaced by nor-MDP, since nor-RIBI was more efficacious as an adjuvant than was RIBI. The low oil formulation of nor-MDP was about 69% effective as RIBI at the earliest time point, but its effectiveness appeared to decrease with time, and at the last time point, its effectiveness was about the same as RIBI-2.

may be a preferred adjuvant for the formulation of gBgD containing vaccines.

6.5. Therapeutic Studies: The effect of adjuvant, site of administration, and timing of administration on vaccine efficacy in preventing subsequent recurrent herpetic disease in guinea pigs The gBgD vaccine consisted of 25 μg each of recombinant gB1 and gD1 purified to approximately 70–80% homogeneity as judged by SDS-PAGE. The recombinant gB1 protein was a 50:50 mixture of gB1 prepared from cell line pHS113-9-10-21 and pHS137-7-B-50; these cell lines are CHO cell lines which harbor the vectors pHS113 and pHS137, respectively. The descriptions for the preparation of pHS113 and pHS137 are in Section 2.2. The gB protein was purified as described in Pachl et al. J of Virology. 61:315–325 (1987), which is essentially as described in Section 6.1. The gD1 was prepared as described in Section 4.6, except that during purification by affinity chromatography the anti-gD1 monoclonal antibody C4D2 replaced 8D2.

The present example compares the efficacy of three

TABLE 8

| Experiment D Adjuvant | Number | Bleed 1 | % MPL + TDM + CWS | Bleed 2 | % MPL + TDM + CWS | Bleed 3 | % MPL + TDM + CWS |
|---|---|---|---|---|---|---|---|
| RIBI | 5(4) | 4239 ± 1152 | 100 | 3205 ± 1460 | 100 | 1702 ± 405 | 100 |
| nor-RIBI | 5 | 9859 ± 802 | 232 | 3292 ± 501 | 103 | 2351 ± 570 | 138 |
| nor-MDP, low oil | 5(2) | 2935 ± 1417 | 69 | 1822 ± 220 | 57 | 720 ± 130 | 42 |
| RIBI-2 | 4 | 72 ± 2 | 2 | 858 ± 619 | 27 | 743 ± 145 | 44 |

6.4.5. Comparison of RIBI, MTP-RIBI, and different formulations containing MTP-PE The animals were immunized with gD1 containing vaccines formulated with either RIBI, a derivative or RIBI in which the CWS component was substituted with MTP-PE (MTP-RIBI), MTP-PE in a high oil delivery system (Squalene/Arlacel). MTP-PE in a low oil delivery system. The low oil formulation of MTP-PE contained 4% Squalene and 0.0008% Tween 80. The gD1 antibody titers obtained with these adjuvant formulations are shown in Table 9.

As seen in Table 9, the MTP-PE formulation was effective as an adjuvant, even when used as the only constituent in the low oil-detergent formulation. It was also an effective substitute for the CWS component in RIBI, moreover, compared to RIBI its effectiveness increased with time. At the third bleed, the titers obtained with MTP-RIBI were twice that obtained with RIBI.

adjuvants, nor-MDP, RIBI, and CFA. RIB1 consisted of a mixture of 50 μg of detoxified monophorphoryl lipid A, 50 μg trehalose dimycolate, and 5 μg CSW per dose, presented in 2% squalene-Tween 80, all provided by Ribi Immunochem. The adjuvant nor-MDP was used at 50 μg/dose emulsified with 50% squalene/arlacel and the antigen.

The present study also compares two routes of administration, i.e.. administration into footpads with administration which is intramuscular or subcutaneous. Finally, it compares various times of administration on the prevention of subsequent recurrent herpetic disease in guinea pigs. The experimental design is shown in Table 10.

TABLE 10

| | | Chrion 7 Experimental Design | | | |
|---|---|---|---|---|---|
| | | | Treatment | | |
| Group | N | Immunogen | Adjuvant | Route | Day[c] |
| 1 | 11 | none | | | |

TABLE 9

| Experiment E Adjuvant | Number | Bleed 1 | % MPL + TDM + CWS | Bleed 2 | % MPL + TDM + CWS | Bleed 3 | % MPL + TDM + CWS |
|---|---|---|---|---|---|---|---|
| RIBI | 5(4) | 15912 ± 3191 | 100 | 8000 ± 1271 | 100 | 1318 ± 310 | 100 |
| MTP + RIBI | 5 | 9218 ± 9411 | 58 | 9836 ± 1262 | 123 | 2678 ± 533 | 203 |
| MTP-PE squalene/arlacel | 4 | 14803 ± 3751 | 93 | 14731 ± 3860 | 184 | 1181 ± 433 | 90 |
| MTP-PE, low oil | 5 | 10694 ± 2135 | 67 | 17072 ± 3457 | 213 | 2455 ± 535 | 186 |

The MTP-PE adjuvant is simpler than RIBI, since MTP-PE contains only one component and RIBI contains three components. Moreover, MTP-PE is potentially safer than RIBI, since it is a defined chemical which is synthetic, and RIBI contains components which are isolated from bacteria. Therefore, MTP-PE

| 2 | 13 | none[a] | | | |
| 3 | 10 | gBgD | CFA | FP | 15,35 |
| 4 | 12 | gBgD | CFA | FP | 21,42 |
| 5 | 10 | gBgD[a] | CFA | FP | 21,42 |
| 6 | 11 | gBgD | none | IM/SC | 21,42 |
| 7 | 13 | gBgD | Ribi | IM/SC | 21,42 |

TABLE 10-continued

| | | Chrion 7 Experimental Design | | | |
|---|---|---|---|---|---|
| | | | Treatment | | |
| Group | N | Immunogen | Adjuvant | Route | Day[c] |
| 8 | 10 | gBgD | nor-MDP | IM/SC | 21,42 |
| 9[b] | — | — | — | — | — |
| 10 | 10 | gBgD | none | FP | 21,42 |
| 11 | 11 | gBgD | Ribi | FP | 21,42 |
| 12 | 11 | gBgD | nor-MDP | FP | 21,42 |
| 13 | 6 | gBgD | CFA | FP | 8,28 |

[a]Daily vaginal swabs done d22-d100 to titer virus and assess asymptomatic shedding.
[b]Group 9 was eliminated.
[c]Day of administration of vaccine post-infection with initial virus exposure on day 1.

Female Hartley guinea pigs weighing 350–400 g were intravaginally inoculated with $5.7/\log_{10}$ pfu of HSV-2 strain MS on day 1. Animals were confirmed to be infected by recovery of HSV from vaginal swab samples collected 24 hr after intravaginal inoculation. The clinical course of initial infection was monitored and quantitated by a gential skin lesion score as described in Stanberry et al. *J Infec Dis* (1987) 155:914. After recovery from initial infection animals were randomized for the treatment groups shown in Table 10. Animals were examined daily for evidence of recurrent disease from days 11 to 100 after the resolution of the acute disease. Lesion days are defined as days on which recurrent lesions are observed, severe recurrences are days when more than one vesicle is noted, and episodes are the occurrence of a new lesion following a lesion free day.

The results obtained from analyses of the animals on days 22–76 are presented in Table 11. The data in Table 11 suggests that for IM injection, nor-MDP is more effective than RIB1 as an adjuvant; this is reflected in a lower total number of lesion days, a smaller percent of severe recurrences, and a diminishment in the total number of herpetic episodes. Moreover, the vaccine containing nor-MDP and administered IM appeared to be as effective as the vaccine containing CFA and administered in the footpads.

TABLE 11

Chiron 7
Effect of HSV-1 gBgD Vaccine Administered
After Intravaginal HSV-2 Inoculation
on Pattern of Recurrent Genital Herpes
Preliminary Analysis - Days 22-76

| Group # | Treatment | N | Total Lesion Days* | Percent Sever Recurrences* | Total Episodes* |
|---|---|---|---|---|---|
| 1 | Untreated | 11 | 16.7 ± 2.1 | 29.0 ± 5.7 | 8.9 ± 0.8 |
| 13 | gBgD-Day 8-CFA-FP | 5 | 9.0 ± 2.2 | 14.2 ± 3.9 | 5.8 ± 0.9 |
| 3 | gBgD-Day 15-CFA-FP | 9 | 10.0 ± 3.0 | 19.5 ± 7.4 | 6.2 ± 1.4 |
| 4 | gBgD-Day 21-CFA-FP | 11 | 11.6 ± 2.0 | 24.2 ± 3.2 | 7.3 ± 1.1 |
| 6 | gBgD-Day 21-No-Adj-IM | 10 | 14.2 ± 2.0 | 25.1 ± 5.3 | 8.0 ± 0.9 |
| 7 | gBgD-Day 21-RIBI-IM | 12 | 14.4 ± 2.2 | 29.8 ± 5.0 | 7.9 ± 0.9 |
| 8 | gBgD-Day 21-nor-MDP-IM | 8 | 10.0 ± 1.8 | 20.5 ± 4.3 | 6.4 ± 1.1 |
| 10 | gBgD-Day 21-No Adj-FP | 10 | 14.5 ± 2.1 | 20.3 ± 3.1 | 8.9 ± 1.2 |
| 11 | gBgD-Day 21-RIBI-FP | 11 | 10.7 ± 1.9 | 25.0 ± 4.2 | 6.9 ± 1.0 |
| 12 | gBgD-Day 21-nor-MDP | 9 | 14.8 ± 1.9 | 25.4 ± 5.0 | 8.2 ± 0.7 |

*Mean ± SE

The local reactions resulting from injection of the vaccines containing the various adjuvants was also monitored, and the results are shown in Table 12. The incidence of local erythema and induration at the site of injection was the same for vaccines containing nor-MDP as for vaccines containing RIBI. Moreover, based upon the local reactogenicity, both adjuvants appear to be acceptable for use in vaccines.

TABLE 12

Chiron 7 Reactions Summary

| Group | N | ΔT°a | Erythema | Induration | Vaccine | Adjuvant | Route |
|---|---|---|---|---|---|---|---|
| Vaccination #1 | | | | | | | |
| 1[d] | 11 | ND[b] | —[c] | — | O | O | O |
| 4[d] | 12 | .08 ± .40 | — | — | gBgD | CFA | FP |
| 6 | 12 | .52 ± .27 | 4 | 0 | gBgD | O | IM |
| 7 | 13 | .20 ± .30 | 11 | 7 | gBgD | RIBI | IM |
| 8 | 10 | .00 ± .27 | 5 | 10 | gBgD | nor-MDP | IM |
| Vaccination #2 | | | | | | | |
| 1 | 11 | .01 ± .46 | — | — | O | O | O |
| 4 | 12 | .98 ± .27 | — | — | gBgD | CFA | FP |
| 6 | 12 | .52 ± .27 | 4 | 0 | gBgD | O | IM |
| 7 | 13 | .27 ± .51 | 8 | 8 | gBgD | RIBI | IM |
| 8 | 8 | .01 ± .48 | 7 | 8 | gBgD | nor-MDP | IM |

[a]Temperature day 1 following vaccine - day 0 for vaccine (mean ± SD) (i.e., D22-21 or D 43-42)
[b]ND - not done
[c]Not applicable
[d]All animals had R let naired prior to vaccination except these The results in Table 11 also show that the relative efficacy of treatment increases as the interval between the initiation of immunotherapy and the onset of acute disease decreases. In animals which had received gBgD vaccine containing CFA beginning 8, 15, or 21 days after the initial infection, those animals which had received the vaccine the shortest time after intravaginal inoculation suffered the smallest number of lesion days, had the lowest percent of severe recurrences, and the fewest total episodes compared to the untreated control. The values obtained for the animals vaccinated 15 days after infection was higher than those obtained for the 8 day vaccination group, and the 21 day group was higher than the 15 day group. This effect is also shown in FIG. 18, which presents a graph of the number of recurrences on the days after intravaginal inoculation for animals which were initially vaccinated 8, 15, or 21 days after the HSV-2 inoculation.

Figure 18:
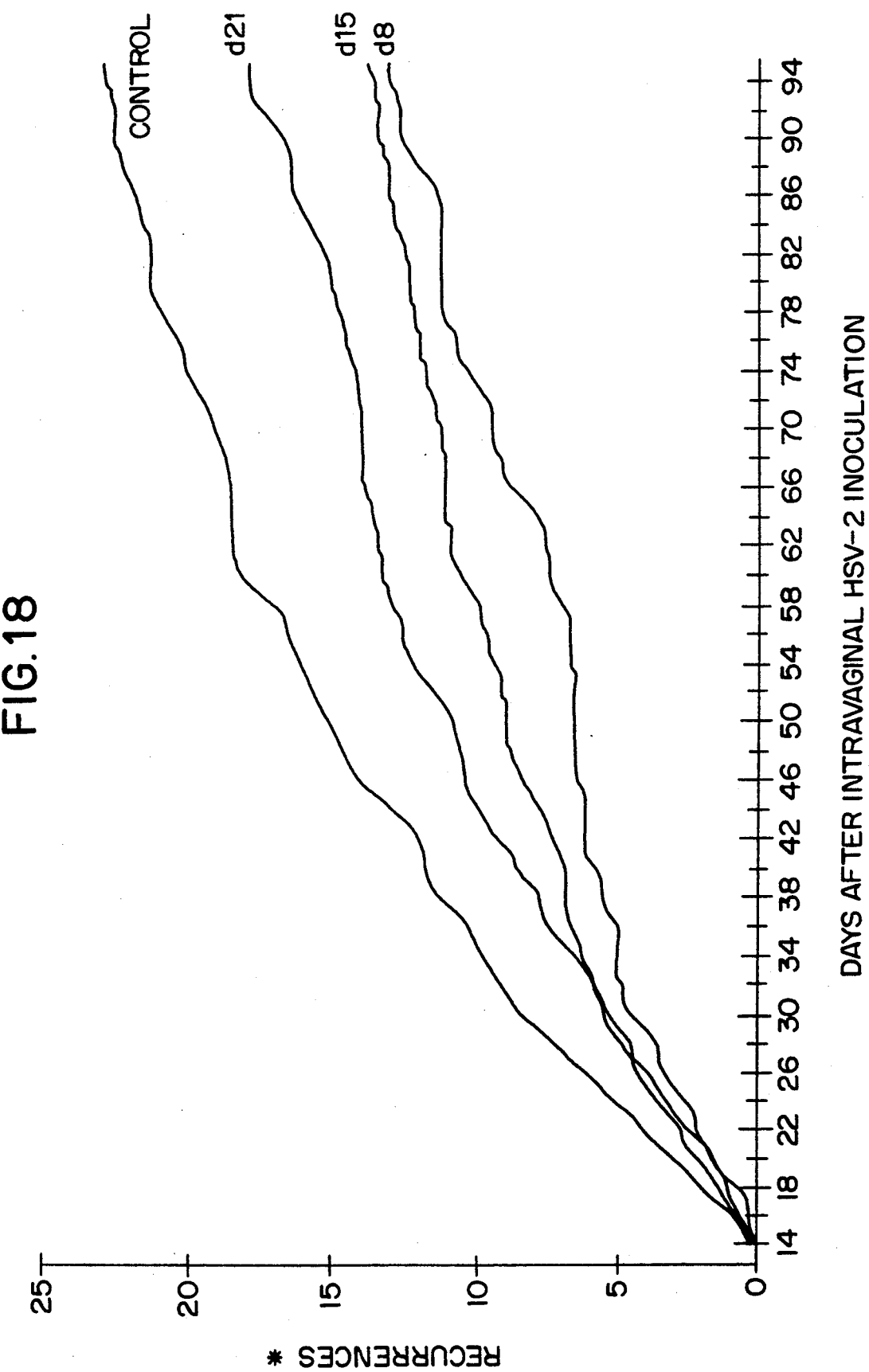
FIG. 18 is a graph showing the effect of the time of administration of gBgD vaccine on the recurrence of herpetic disease.

The data in FIG. 18 was used to calculate the percent reduction in the rates of recurrent disease (See Section 6.2 for an explanation of the significance of the rate of recurrent disease). This data is presented in Table 13, where it may be seen that at earliest time periods, i.e., 14–50 days, the greatest percent reduction in the rate of recurrent disease was obtained by giving the initial vaccination at 8 days. However, from 51–92 days, the most effective protection was obtained by giving the initial vaccination 15 days after the intravaginal inoculation with HSV. The least protection occurred when the initial vaccination was given 21 days after the initial exposure to HSV-2.

TABLE 13

Chiron 7
(Weekly Rate) Rates of Recurrence After Glycoprotein Treatment

| Day 8 | 14–29 | 30–50 | 51–71 | 72–92 |
|---|---|---|---|---|
| UNRx | 3.30 | 2.48 | 1.42 | 1.15 |
| gBgD | 1.75 | 0.80 | 1.0 | 0.94 |
| % Control | 53.0% | 32.3% | 70.4 | 81.7 |
| % Reduction | 47.0% | 67.7% | 29.6% | 18.3% |

TABLE 13-continued

| Chiron 7 (Weekly Rate) Rates of Recurrence After Glycoprotein Treatment | | | | |
| --- | --- | --- | --- | --- |
| Day 15 | 16–36 | 37–57 | 58–78 | 79–85 |
| UNRx | 3.27 | 2.09 | 1.42 | 0.97 |
| gBgD | 2.03 | 1.04 | 0.81 | 0.64 |
| % Control | 62.0% | 49.8% | 57.0% | 66.0% |
| % Reduction | 38.0% | 50.2% | 43.0% | 34.0% |
| Day 21 | 22–42 | 43–63 | 64–84 | 85–92 |
| UNRx | 2.82 | 2.18 | 1.03 | 0.85 |
| gBgD | 2.09 | 1.46 | 0.76 | 1.33 |
| % Control | 74.1% | 67.0% | 73.8% | 156.5% |
| % Reduction | 25.9% | 33.0% | 26.2% | 56.5% |

According to the present invention, novel vaccines are provided effective against Herpes Simplex Virus Types 1 and 2 administered either pre-viral infection or post-viral infection.

Although the foregoing invention has been described in some detail by way of illustration and example for purpose of clarity and understanding, it will be obvious that certain changes and modifications may be practiced within the scope of the appended claims.

What is claimed is:

1. A vaccine formulation consisting essentially of herpes simplex virus (HSV) polypeptides wherein the HSV polypeptides are:
   (a) immunogenic;
   (b) glycosylated; and
   (c) consist of:
      (i) a HSV glycoprotein B polypeptide or immunogenic fragments thereof; and
      (ii) a HSV glycoprotein D polypeptide or immunogenic fragments thereof.

2. A vaccine according to claim 1, wherein the glycoprotein B is a Type 1 glycoprotein B and the glycoprotein D is a Type 1 glycoprotein D.

3. A vaccine according to claim 1, wherein the glycoprotein B is a Type 1 glycoprotein B and the glycoprotein D is a Type 2 glycoprotein D.

4. A vaccine according to claim 1, wherein the glycoprotein B is a Type 2 glycoprotein B and the glycoprotein D is a Type 1 glycoprotein D.

5. A vaccine according to claim 1, wherein the glycoprotein B is a Type 2 glycoprotein B and the glycoprotein D is a Type 2 glycoprotein D.

6. A vaccine according to claim 1, wherein the glycoprotein B is a Type 1 and a Type 2 glycoprotein B and the glycoprotein D is a Type 1 and a Type 2 glycoprotein D.

7. A vaccine according to claim 1, wherein the polypeptides include an anchor sequence.

8. A vaccine according to claim 1, wherein the polypeptides are substantially free of an anchor sequence.

9. A vaccine according to claim 1, wherein the polypeptides are each of molecular weight about 1500 to 5000 daltons.

10. A vaccine according to claim 1, wherein said vaccine includes a pharmacologically acceptable carrier.

11. A vaccine according to claim 1, wherein said vaccine includes an adjuvant.

12. A method for immunizing a mammal against herpes simplex virus infection comprising vaccinating the mammal with the vaccine of claim 1, wherein the mammal is vaccinated subsequent to a primary infection with herpes simplex virus.

13. A method of reducing the rate of recurrent herpetic disease in a mammal that has been subjected to primary infection with herpes simplex virus comprising administering the vaccine of claim 1 to the mammal.

14. A vaccine according to claim 1, wherein the HSV glycoprotein B polypeptide is substantially free of an anchor sequence.

15. A vaccine according to claim 11, wherein the adjuvant is alum.

16. A vaccine according to claim 11, wherein the adjuvant is N-acetyl-nor-muramyl-L-alanyl-D-isoglutamine.

17. A vaccine according to claim 11, wherein the adjuvant is formulated in a low oil formulation.

18. A vaccine according to claim 11, wherein the adjuvant is 4% Squalene and 0.0008% Tween 80.

19. A vaccine according to claim 11, wherein the adjuvant is N-acetylmuramyl-L-analyl-D-isoglutaminyl-L-alanine-2-(1'-2'-dipalmitoyl-sn-glycero-3-hydroxyphosphoryloxy)-ethylamine.

20. A vaccine according to claim 19, wherein the adjuvant is formulated in a low oil formulation.

21. A vaccine according to claim 20, wherein the adjuvant is formulated in 4% Squalene and 0.0008% Tween 80.

22. A vaccine according to claim 11, wherein at least one of the immunologically active polypeptides and the adjuvant are encapsulated in a liposome.

23. A vaccine according to claim 22, wherein the adjuvant is N-acetylmuramyl-L-analyl-D-isoglutaminyl-L-alanine-2-(1'-2'-dipalmitoyl-sn-glycero-3-hydroxyphosphoryloxy)-ethylamine.

* * * * *

UNITED STATES PATENT AND TRADEMARK OFFICE
CERTIFICATE OF CORRECTION

PATENT NO. : 5,171,568
DATED : December 15, 1992
INVENTOR(S) : Rae L. Burke, San Francisco; Carol Pachl, Oakland; Pablo D.T. Valenzuela, San Francisco, all of California It is certified that error appears in the above-identified patent and that said Letters Patent is hereby corrected as shown below:

Title Page

[63]  Delete: "Continuation of Ser. No. 079,605, Jul. 29, 1987, abandoned, which is a continuation-in-part of Ser. No. 921,213, Oct. 20, 1986, abandoned, which is a continuation-in-part of Ser. No. 597,784, Apr. 8, 1984, abandoned, and a continuation-in-part of Ser. No. 631,669, Jul. 17, 1984, Pat. No. 4,618,578."

[63]  Correct: --Continuation of Ser. No. 079,605, Jul. 29, 1987, abandoned, which is a continuation-in-part of Ser. No. 921,213, Oct. 20, 1986, abandoned, which is a continuation-in-part of Ser. No. 597,784, Apr. 6, 1984, abandoned, and a continuation-in-part of Ser. No. 631,669, Jul. 17, 1984, Pat. No. 4,618,578.--

Signed and Sealed this

Fourth Day of January, 1994

Attest:

BRUCE LEHMAN

*Attesting Officer*   *Commissioner of Patents and Trademarks*